(12) United States Patent
Albæk et al.

(10) Patent No.: US 10,385,342 B2
(45) Date of Patent: Aug. 20, 2019

(54) METHODS OF TREATMENT USING ANTISENSE OLIGOMERS AND CONJUGATES TARGETING PCSK9

(71) Applicant: ROCHE INNOVATION CENTER COPENHAGEN A/S, Hørsholm (DK)

(72) Inventors: Nanna Albæk, Hørsholm (DK); Maj Hedtjärn, Hørsholm (DK); Marie Wickstrom Lindholm, Hørsholm (DK); Niels Fisker Nielsen, Hørsholm (DK); Andreas Petri, Hørsholm (DK); Jacob Ravn, Hørsholm (DK)

(73) Assignee: ROCHE INNOVATION CENTER COPENHAGEN A/S, Hørsholm (DK)

( * ) Notice: Subject to any disclaimer, the term of this patent is extended or adjusted under 35 U.S.C. 154(b) by 0 days.

(21) Appl. No.: 15/971,970

(22) Filed: May 4, 2018

(65) Prior Publication Data

US 2018/0312847 A1    Nov. 1, 2018

Related U.S. Application Data

(63) Continuation of application No. 15/836,144, filed on Dec. 8, 2017, which is a continuation of application No. 14/897,223, filed as application No. PCT/EP2014/063757 on Jun. 27, 2014, now Pat. No. 9,879,265.

(30) Foreign Application Priority Data

| | | |
|---|---|---|
| Jun. 27, 2013 | (EP) | 13174092 |
| Nov. 14, 2013 | (EP) | 13192930 |
| Nov. 14, 2013 | (EP) | 13192938 |
| Nov. 14, 2013 | (WO) | PCT/EP2013/073858 |
| Jan. 30, 2014 | (EP) | 14153253 |
| May 14, 2014 | (EP) | 14168331 |

(51) Int. Cl.
| | |
|---|---|
| *A61K 48/00* | (2006.01) |
| *C07H 21/02* | (2006.01) |
| *C07H 21/04* | (2006.01) |
| *C12N 15/113* | (2010.01) |
| *A61K 47/54* | (2017.01) |
| *A61K 31/712* | (2006.01) |

(52) U.S. Cl.
CPC ........ *C12N 15/1137* (2013.01); *A61K 47/545* (2017.08); *A61K 47/549* (2017.08); *A61K 47/554* (2017.08); *C12N 15/113* (2013.01); *A61K 31/712* (2013.01); *C12N 2310/11* (2013.01); *C12N 2310/3231* (2013.01); *C12N 2310/341* (2013.01); *C12N 2310/351* (2013.01); *C12N 2310/3515* (2013.01); *C12N 2320/32* (2013.01); *C12N 2330/30* (2013.01)

(58) Field of Classification Search
CPC .... C12N 15/113; C12N 15/111; A61K 31/713
See application file for complete search history.

(56) References Cited

U.S. PATENT DOCUMENTS

| | | |
|---|---|---|
| 4,914,210 A | 4/1990 | Levenson et al. |
| 4,962,029 A | 10/1990 | Levenson et al. |
| 5,919,795 A | 7/1999 | Chang et al. |
| 6,030,785 A | 2/2000 | Katze et al. |
| 6,121,283 A | 9/2000 | Chang et al. |
| 6,284,458 B1 | 9/2001 | Anderson et al. |
| 6,423,489 B1 | 7/2002 | Anderson et al. |
| 6,433,159 B1 | 8/2002 | Anderson |
| 7,029,895 B2 | 4/2006 | Glucksmann et al. |
| 7,087,229 B2 | 8/2006 | Zhao et al. |
| 7,605,251 B2 | 10/2009 | Tan et al. |
| 7,683,036 B2 | 3/2010 | Esau et al. |
| 7,687,617 B2 | 3/2010 | Thrue et al. |
| 7,737,264 B2 | 6/2010 | Thrue et al. |
| 7,888,324 B2 | 2/2011 | Crooke et al. |
| 8,143,230 B2 | 3/2012 | Bhanot et al. |
| 8,563,528 B2 | 10/2013 | Straarup et al. |
| 9,879,265 B2 | 1/2018 | Albak et al. |
| 2003/0125241 A1 | 7/2003 | Wissenbach et al. |
| 2003/0199467 A1 | 10/2003 | Roberts et al. |
| 2004/0009553 A1 | 1/2004 | Glucksmann et al. |
| 2005/0069522 A1 | 3/2005 | Colonno et al. |
| 2005/0261218 A1 | 11/2005 | Esau et al. |
| 2006/0035212 A1 | 2/2006 | Balakireva |
| 2006/0035858 A1 | 2/2006 | Geary et al. |

(Continued)

FOREIGN PATENT DOCUMENTS

| | | |
|---|---|---|
| EP | 0 699 751 A1 | 3/1996 |
| EP | 1 099 442 A2 | 5/2001 |

(Continued)

OTHER PUBLICATIONS

Beaucage, L. and Iyer, R., "Advances in the Synthesis of Oligonucleotides by the Phosphoramidite Approach," *Tetrahedron* 48:2223-2311, Pergamon Press, United Kingdom (1992).

Beaucage, L. and Iyer, R., "The Synthesis of Modified Oligonucleotides by the Phosphoramidite Approach and Their Applications," *Tetrahedron* 49:6123-6194, Pergamon Press, United Kingdom (1993).

Braasch, D., et al., "Antisense inhibition of gene expression in cells by oligonucleotides incorporating locked nucleic acids: effect of mRNA target sequence and chimera design," *Nucleic Acids Res.* 30:5160-5167, Oxford University Press, United Kingdom (2002).

Christensen, U. and Pedersen, E., "Intercalating nucleic acids containing insertions of 1-O-(1-pyrenylmethyl)glycerol: stabilisation of dsDNA and discrimination of DNA over RNA," *Nucleic Acids Res.* 30:4918-4925, Oxford University Press, United Kingdom (2002).

(Continued)

*Primary Examiner* — Amy H Bowman
(74) *Attorney, Agent, or Firm* — Sterne, Kessler, Goldstein & Fox, P.L.L.C.

(57) ABSTRACT

The present invention relates to oligomeric compounds and conjugates thereof that target Proprotein Convertase Subtilisin/Kexin type 9 (PCSK9) PCSK9 mRNA in a cell, leading to reduced expression of PCSK9. Reduction of PCSK9 expression is beneficial for a range of medical disorders, such as hypercholesterolemia and related disorders.

63 Claims, 19 Drawing Sheets

Specification includes a Sequence Listing.

(56) References Cited

U.S. PATENT DOCUMENTS

| | | |
|---|---|---|
| 2006/0040989 A1 | 2/2006 | Meerpoel et al. |
| 2006/0185027 A1 | 8/2006 | Bartel et al. |
| 2007/0173473 A1 | 7/2007 | McSwiggen et al. |
| 2008/0015162 A1 | 1/2008 | Bhanot et al. |
| 2009/0318536 A1 | 12/2009 | Freier et al. |
| 2010/0144834 A1 | 6/2010 | Freier et al. |
| 2010/0216864 A1 | 8/2010 | Straarup et al. |
| 2011/0224280 A1 | 9/2011 | Nielsen et al. |
| 2012/0302589 A1* | 11/2012 | Manku .............. A61K 31/202 514/275 |

FOREIGN PATENT DOCUMENTS

| | | |
|---|---|---|
| EP | 0 662 157 B1 | 6/2001 |
| EP | 1 222 309 B1 | 7/2005 |
| EP | 1 984 381 B1 | 9/2010 |
| JP | 2000-501414 A | 2/2000 |
| JP | 2011-511004 A | 4/2011 |
| JP | 2011-518784 A | 6/2011 |
| WO | WO 95/30746 A1 | 11/1995 |
| WO | WO 97/020563 A1 | 6/1997 |
| WO | WO 99/14226 A2 | 3/1999 |
| WO | WO 00/56746 A2 | 9/2000 |
| WO | WO 00/56748 A1 | 9/2000 |
| WO | WO 00/66604 A2 | 11/2000 |
| WO | WO 01/23613 A1 | 4/2001 |
| WO | WO 01/25248 A2 | 4/2001 |
| WO | WO 01/48190 A2 | 7/2001 |
| WO | WO 01/57081 A2 | 8/2001 |
| WO | WO 02/28875 A2 | 4/2002 |
| WO | WO 02/094250 A2 | 11/2002 |
| WO | WO 03/006475 A2 | 1/2003 |
| WO | WO 03/011887 A2 | 2/2003 |
| WO | WO 03/085110 A2 | 10/2003 |
| WO | WO 03/095467 A1 | 11/2003 |
| WO | WO 2004/044141 A2 | 5/2004 |
| WO | WO 2004/044181 A2 | 5/2004 |
| WO | WO 2004/046160 A2 | 6/2004 |
| WO | WO 2004/069991 A2 | 8/2004 |
| WO | WO 04/097047 A1 | 11/2004 |
| WO | WO 2005/013901 A2 | 2/2005 |
| WO | WO 2005/023825 A2 | 3/2005 |
| WO | WO 2005/054494 A2 | 6/2005 |
| WO | WO 2005/058824 A2 | 6/2005 |
| WO | WO 2005/061710 A1 | 7/2005 |
| WO | WO 2005/073378 A1 | 8/2005 |
| WO | WO 2005/086775 A2 | 9/2005 |
| WO | WO 2005/098029 A2 | 10/2005 |
| WO | WO 2005/107816 A2 | 11/2005 |
| WO | WO 2006/010423 A2 | 2/2006 |
| WO | WO 2006/020676 A2 | 2/2006 |
| WO | WO 2006/020768 A2 | 2/2006 |
| WO | WO 2006/036916 A2 | 4/2006 |
| WO | WO 2006/053430 A1 | 5/2006 |
| WO | WO 2006/093526 A2 | 9/2006 |
| WO | WO 2006/112872 A2 | 10/2006 |
| WO | WO 2006/113910 A2 | 10/2006 |
| WO | WO 2007/031081 A2 | 3/2007 |
| WO | WO 2007/031091 A2 | 3/2007 |
| WO | WO 2007/090071 A2 | 8/2007 |
| WO | WO 2007/112753 A2 | 10/2007 |
| WO | WO 2007/112754 A2 | 10/2007 |
| WO | WO 2007/131237 A2 | 11/2007 |
| WO | WO 2007/134181 A2 | 11/2007 |
| WO | WO 2007/143315 A2 | 12/2007 |
| WO | WO 2007/146511 A1 | 12/2007 |
| WO | WO 2008/011431 A2 | 1/2008 |
| WO | WO 2008/034122 A2 | 3/2008 |
| WO | WO 2008/034123 A2 | 3/2008 |
| WO | WO 2008/043753 A2 | 4/2008 |
| WO | WO 2008/061537 A2 | 5/2008 |
| WO | WO 2008/066776 A2 | 6/2008 |
| WO | WO 2008/089767 A1 | 7/2008 |
| WO | WO 2008/109472 A2 | 9/2008 |
| WO | WO 2008/124384 A2 | 10/2008 |
| WO | WO 2008/150729 A2 | 12/2008 |
| WO | WO 2008/154401 A2 | 12/2008 |
| WO | WO 2009/020771 A2 | 2/2009 |
| WO | WO 2009/025669 A2 | 2/2009 |
| WO | WO 2009/067647 A1 | 5/2009 |
| WO | WO 2009/073809 A2 | 6/2009 |
| WO | WO 2009/090182 A1 | 7/2009 |
| WO | WO 2009/126933 A2 | 10/2009 |
| WO | WO 2009/127680 A1 | 10/2009 |
| WO | WO 2009/134487 A2 | 11/2009 |
| WO | WO 2009/148605 A2 | 12/2009 |
| WO | WO 2011/009697 A1 | 1/2011 |
| WO | WO 2011/126937 A2 | 10/2011 |
| WO | WO 2012/058693 A2 | 5/2012 |
| WO | WO 2012/083046 A2 | 6/2012 |
| WO | WO 2014/118267 A2 | 7/2014 |
| WO | WO 2014/179620 A1 | 11/2014 |

OTHER PUBLICATIONS

Costet, P., et al., "Hepatic PCSK9 Expression Is Regulated by Nutritional Status via Insulin and Sterol Regulatory Element-binding Protein 1c," *J. Biol. Chem.* 281:6211-6218, The American Society for Biochemistry and Molecular Biology, Inc., United States (2006).

Crooke, R., "Chapter 3: In Vitro Cellular Uptake, Distribution, and Metabolism of Oligonucleotides," *Antisense Research and Application* 131:103-140, Springer-Verlag, Germany (1998).

Dass, C., "Vehicles for oligonucleotide delivery to tumours," *J. Pharm. Pharmacol.* 54:3-27, Pharmaceutical Press, United Kingdom (2002).

Davidson, N. and Shelness, G., "Apolipoprotein B: mRNA Editing, Lipoprotein Assembly, and Presecretory Degradation," *Annu. Rev. Nutr.* 20:169-193, Annual Reviews, United States (2000).

Davis, S., et al., "Improved targeting of miRNA with antisense oligonucleotides," *Nucleic Acids Res.* 34:2294-2304, Oxford University Press, United Kingdom (2006).

Deere, J., et al., "Antisense Phosphorodiamidate Morpholino Oligomer Length and Target Position Effects on Gene-Specific Inhibition in *Eschericia coli*," *Antimicrobal Agents and Chemotherapy* 49:249-255, American Society for Microbiology, United States (2005).

Elbashir, S., et al., "Analysis of gene function in somatic mammalian cells using small interfering RNAs," *Methods* 26:199-213, Academic Press, United States (2002).

Elmén, J., et al., "Locked nucleic acid containing antisense oligonucleotides enhance inhibition of HIV-1 genome dimerization and inhibit virus replication," *FEBS Letters* 578:285-290, Elsevier B.V., The Netherlands (2004).

Feld, J., et al., "Ribavirin Improves Early Response to Peginterferon Through Improved Interferon Signaling," *Gastroenterology* 139:154-162, W.B. Saunders, United States (2010).

Freier, S. and Altmann, K.-H., "The ups and downs of nucleic acid duplex stability: structure-stability studies on chemically-modified DNA: RNA duplexes," *Nucleic Acids Res.* 25:4429-4443, Oxford University Press, United Kingdom (1997).

Frieden, M., et al., "Expanding the design horizon of antisense oligonucleotides with alpha-L-LNA," *Nucleic Acids Res.* 31:6365-6372, Oxford University Press, United Kingdom (2003).

Gentleman, R., et al., "Bioconductor: open software development for computational biology and bioinformatics," *Genome Biol.* 5:R80, BioMed Central Ltd., United Kingdom (2004).

Giles, R., et al., "Selecting optimal oligonucleotide composition for maximal antisense effect following streptolysin O-mediated delivery into human leukaemia cells," *Nucleic Acid Res.* 26:1567-1575, Oxford University Press, United Kingdom (1998).

Graham, M., et al., "Antisense inhibition of proprotein convertase subtilisin/kexin type 9 reduces serum LDL in hyperlipidemic mice," *J. Lipid Res.* 48:763-767, American Society for Biochemistry and Molecular Biology, Inc., United States (2007).

Greene, T. and Wuts, P., Protective Groups in Organic Synthesis, [Table of Contents], 3rd ed., John Wiley & Sons, Chichester, England (1999).

(56) References Cited

OTHER PUBLICATIONS

Hanecak, R., et al., "Antisense Oligonucleotide Inhibition of Hepatitis C Virus Gene Expression in Transformed Hepatocytes," *J. Virol.* 70:5203-5212, American Society for Microbiology, United States (1996).

Heid, C., et al., "Real Time Quantitative PCR," *Genome Res.* 6:986-994, Cold Spring Harbor Laboratory Press, United States (1996).

Hu, Q., "Subcellular trafficking of antisense oligonucleotides and down-regulation of bcl-2 gene expression in human melanoma cells using a fusogenic liposome delivery system," *Nucleic Acid Res.* 30:3632-3641, Oxford University Press, United Kingdom (2002).

Huang, H., et al., "Hepatitis C virus production by human hepatocytes dependent on assembly and secretion of very low-density lipoproteins," *Proc. Natl. Acad. Sci. U.S.A.* 104:5848-5853, National Academy of Sciences, United States (2007).

Huber, W., et al., "Variance stabilization applied to microarray data calibration and to the quantification of differential expression," *Bioinformatics* 18:S96-S104, Oxford University Press, United Kingdom (2002).

Hutton, J., "Renaturation kinetics and thermal stability of DNA in aqueous solutions of formamide and urea," *Nucleic Acids Res.* 4:3537-3555, Oxford University Press, United Kingdom (1977).

Hutvágner, G., et al., "A Cellular Function for the RNA-Interference Enzyme Dicer in the Maturation of the let-7 Small Temporal RNA," *Science* 293:834-838, American Assn. for the Advancement of Science, United States (2001).

Hutvágner, G., et al., "Sequence-Specific Inhibition of Small RNA Function," *PLoS Biology* 2:0465-0475, Public Library of Science, United States (2004).

Ittig, D., et al., "Nuclear antisense effects in cyclophilin A pre-mRNA splicing by oligonucleotides: a comparison of tricyclo-DNA with LNA," *Nucleic Acids Res.* 32:346-353, Oxford University Press (2004).

Jepsen, J., et al., "Locked Nucleic Acid: A Potent Nucleic Acid Analog in Therapeutics and Biotechnology," *Oligonucleotides* 14:130-146, Mary Ann Liebert, Inc., United States (2004).

Johansson, H., et al., "Target-specific arrest of mRNA translation by antisense 2'-O-alkyloligonucleotides," *Nucleic Acids Res.* 22: 4591-4598, Oxford University Press, United Kingdom (1994).

Johnson, S., et al., "RAS Is Regulated by the let-7 MicroRNA Family," *Cell* 120:635-647, Cell Press, United States (2005).

Kauppinen, S., et al., "Locked nucleic acid (LNA): High affinity targeting of RNA for diagnostics and therapeutics," *Drug Discovery Today: Technologies* 2:287-290, Elsevier, Ltd., The Netherlands (2005).

Ketting, R., et al., "Dicer functions in RNA interference and in synthesis of small RNA involved in developmental timing in C.elegans," *Genes Dev.* 15:2654-2659, Cold Spring Harbor Laboratory Press, United States (2001).

Kloosterman, W., et al., "Substrate requirements for let-7 function in the developing zebrafish embryo," *Nucleic Acids Res.* 32:6284-6291, Oxford University Press, United Kingdom (2004).

Krukemeyer, M., et al., "Description of B lymphocytes and plasma cells, complement, and chemokines/receptors in acute liver allograft rejection," *Transplantation* 78:65-70, Lippincott Williams & Wilkins, United States (2004).

Krützfeldt, J., et al.,"Specificity duplex degradation and subcellular localization of antagomirs," *Nucleic Acids Res.* 35:2885-2892, Oxford University Press, United Kingdom (2007).

Kurreck, J., et al., "Design of antisense oligonucleotides stabilized by locked nucleic acids," *Nucleic Acids Res.* 30:1911-1918, Oxford University Press, United Kingdom (2002).

Lalanne, F., et al., "Wild-type PCSK9 inhibits LDL clearance but does not affect apoB-containing lipoprotein production in mouse and cultured cells," *J. Lipid Res.* 46:1312-1319, American Society for Biochemistry and Molecular Biology, United States (2005).

Lambert, G., et al., "PCSK9: a promising therapeutic target for dyslipidemias?," *Trends Endocrinol. Metab.* 17:79-81, Elsevier Ltd., The Netherlands (2006).

Lanford, R., et al., "Antiviral Effect and Virus-Host Interactions in Response to Alpha Interferon, Gamma Interferon, Poly(I)-poly(C), Tumor Necrosis Factor Alpha, and Ribavirin in Hepatitis C Virus Subgenomic Replicons," *J. Virol.* 77:1092-1104, American Society for Microbiology, United States (2003).

Lanford, R., et al., "Lack of response to exogenous interferon-alpha in the liver of chimpanzees chronically infected with hepatitis C virus," *Hepatology* 46:999-1008, Wiley, United States (2007).

Lima, W., et al., "Combinatorial Screening and Rational Optimization for Biological with Hybridization to Folded Hepatitis C Virus RNA of Oligonucleotides Antisense Activity," *J. Biol. Chem.* 272:626-638, A237 (1997).

Lisziewicz, J., et al., "Long-term treatment of human immunodeficiency virus-infected cells with antisense oligonucleotide phosphorothioates," *Proc. Natl. Acad. Sci.* 90:3860-3864, National Academy of Sciences, United States (1993).

Manoharan, M., et al., "Novel Functionalization of the Sugar Moiety of Nucleic Acids for Multiple Labeling in the Minor Groove," *Tetrahedron Letters* 34:7171-7174, Pergamon Press, PLC., United Kingdom (1991).

Martinez, J., et al., "Single-Stranded Antisense siRNAs Guide Target RNA Cleavage in RNAi," *Cell* 110:563-574, Cell Press, United States (2002).

Matz, M., et al., "Early post-transplant urinary IP-10 expression after kidney transplantation is predictive of short- and long-term graft function," *Kidney Int.* 69:1683-1690, Nature Publishing Group (2006).

McManus, M., and Sharp, P., "Gene Silencing in Mammals by Small Interfering RNAs," *Nat. Rev. Genet.* 3:737-747, Nature PublishingGroup, United Kingdom (2002).

Möröy, T., et al., "Structure and expression of hcr, a locus rearranged with c-myc in a woodchuck hepatocellular carcinoma," *Oncogene* 4:59-65, Nature Publishing Group, United Kingdom (1989).

Neuman, B., et al., "Antisense Morpholino-Oligomers Directed against the 5' End of the Genome Inhibit Coronavirus Proliferation and Growth," *J. Virol.* 78:5891-5899, American Society for Microbiology, United States (2004).

Nulf, C. and Corey, D., "Intracellular inhibition of hepatitis C virus (HCV) internal ribosomal entry site (IRES)-dependent translation by peptide nucleic acids (PNAs) and locked nucleic acids (LNAs)," *Nucleic Acids Res.* 32:3792-3798, Oxford University Press, United Kingdom (2004).

Ørom U. et al., "LNA-modified oligonucleotides mediate specific inhibition of microRNA function," *Gene* 372:137-141, Elsevier, Inc., The Netherlands (2006).

Park, S., et al., "Post-transcriptional Regulation of Low Density Lipoprotein Receptor Protein by Proprotein Convertase Subtilisin/Kexin Type 9a in Mouse Liver," *J. Biol. Chem.* 279:50630-50638, The American Society for Biochemistry and Molecular Biology, Inc., United States (2004).

Paushkin, S., et al., "The SMN complex, an assemblyosome of ribonucleoproteins," *Curr. Opin. Cell Biol.* 14:305-312, Elsevier Science Ltd., United Kingdom (2002).

Pedersen, D., et al., "Preparation of LNA Phosphoramidites," *Synthesis* 6:802-808, Thieme/Academic Press, Germany (2002).

Pedersen, D., and Koch, T., "Analogues of LNA (Locked Nucleic Acid). Synthesis of the 2'Thio-LNA Thymine and 5-Methyl Cytosine Phosphoramidites," *Synthesis* 4:578-582, Thieme/Academic Press, Germany (2003).

Petri, A., et al., "MicroRNA Silencing in Primates: Towards Development of Novel Therapeutics," *Can. Res.* 69:393-395, American Association for Cancer Research, United States (2009).

Prakash, T., et al., "Antisense Oligonucleotides Containing Conformationally Constrained 2',4'-(N-Methoxy)aminomethylene and 2',4'-Aminooxymethylene and 2'-O,4'-C-Aminomethylene Bridged Nucleoside Analogues Show Improved Potency in Animal Models," *J. Med. Chem.* 53:1636-1650, American Chemical Society, United States (2010).

Randall, G., et al., "Cellular cofactors affecting hepatitis C virus infection and replication," *Proc. Natl. Acad. Sci. USA* 104:12884-12889, National Academy of Sciences, United States (2007).

(56) References Cited

OTHER PUBLICATIONS

Rashid, S., et al., "Decreased plasma cholesterol and hypersensitivity to statins in mice lacking Pcsk9," *Proc. Natl. Acad. Sci. U.S.A.* 102:5374-5379, National Academy of Sciences, United States (2005).
Rosenbohm, C., et al., "Synthesis of 2'-amino-LNA: a new strategy," *Org. Biomol. Chem.* 1:655-663, Royal Society of Chemistry, United Kingdom (2003).
Saeed, A., et al.,"TM4: A Free, Open-Source System for Microarray Data Management and Analysis," *BioTechniques* 34:374-378, Informa Healthcare USA, Inc., United Kingdom (2003).
Samuel, D., "Hepatitis C, Interferon, and Risk of Rejection After Liver Transplantation," *Liver Transpl.* 10:868-887, Wiley InterScience, United States (2004).
Santaris Pharma, Nature Genetics Ad, Jun. 2006 [powerpoint slide], 1 page.
Sazani, P., et al., "Nuclear antisense effects of neutral, anionic and cationic oligonucleotide analogs," *Nucleic Acids. Res.* 29:3965-3974, Oxford University Press, United Kingdom (2001).
Schwarz, D., et al., "Evidence that siRNAs Function as Guides, Not Primers, in the *Drosophila* and Human RNAi Pathways," *Mol. Cell* 10:537-548, Cell Press, United States (2002).
Seth, P., et al., "Synthesis and Biophysical Evaluation of 2',4'-Constrained 2'O-Methoxyethyl and 2',4'-Constrained 2'O-Ethyl Nucleic Acid Analogues," *J. Org. Chem.* 75:1569-1581, American Chemical Society, United States (2010).
Singh, S. and Wengel, J., "Synthesis of Novel Bicyclo [2.2.1] Ribonucleosides: 2'-Amino- and 2'-Thio-LNA Monomeric Nucleosides," *J. Org. Chem.* 63:6078-6079, American Chemical Society, United States (1998).
Sørensen, M., et al.,"α-L-ribo-Configured Locked Nucleic Acid (α-L-LNA): Synthesis and Properties," *J. Am. Chem. Soc.* 124:2164-2176, American Chemical Society, United States (2002).
Tallet-Lopez, B., et al.," Antisense oligonucleotides targeted to the domain IIId of the hepatitis C virus IRES compete with 40S ribosomal subunit binding and prevent in vitro translation," *Nucleic Acids Res.* 31:734-742, Oxford University Press, Kingdom (2003).
Tam, W., "Identification and characterization of human BIC, a gene on chromosome 21 that encodes a noncoding RNA," *Gene* 274:157-167, Elsevier, The Netherlands (2001).
Tijsterman, M., et al., "RNA Helicase MUT-14-Depedent Gene Silencing Triggered in *C. elegans* by Short Antisense RNAs," *Science* 295:694-697, American Assn. for the Advancement of Science, United States (2002).
Uhlmann, E., "Recent advances in the medicinal chemistry of antisense oligonucleotides," *Curr. Opin. Drug Discov. Develop.* 3:203-213, Pharma Press Ltd., United Kingdom (2000).
Wagner, R., "Gene inhibition using antisense oligodeoxynucleotides," *Nature* 372:333-335, Nature Publishing Group, United Kingdom (1994).
Wagner, R., et al., "Potent and selective inhibition of gene expression by an antisense heptanucleotide," *Nat. Biotechnol.* 14:840-844, Nature Publishing Group, United States (1996).
Wahlestedt, C., et al., "Potent and nontoxic antisense oligonucleotides containing locked nucleic acids," *Proc. Natl. Acad. Sci. USA* 97:5633-5638, National Academy of the Sciences, United States (2000).
Walter, T., et al., "Rejection Under Alpha Interferon Therapy in Liver Transplant Recipients," *Am. J. Transplant.* 7:177-184, Blackwell Munksgaard, Denmark (2007).
Yu, J., et al., "RNA interference by expression of short-interfering RNAs and hairpin RNAs in mammalian cells," *Proc. Natl. Acad. Sci.* 99:6047-6052, National Academy of Sciences, United States (2002).
Zhang, H., et al., "Antisense Oligonucleotide Inhibition of Hepatitis C Virus (HCV) Gene Expression in Livers of Mice Infected with an HCV-Vaccinia Virus Recombinant," *Antimicrob. Agents and Chemother.* 43 :347-353, American Society for Microbiology, United States (1999)

Zhao, Y., et al., "Serum response factor regulates a muscle-specific microRNA that targets Hand2 during cardiogenesis," *Nature* 436:214-220, Nature Publishing Group, United Kingdom (2005).
International Search Report for International Application No. PCT/EP2007/060703, European Patent Office, dated Aug. 13, 2008.
Bennett, C.F., et al., "An ICAM-1 Antisense Oligonucleotide Prevents and Reverses Dextran Sulfate Sodium-Induced Colitis in Mice," *Journal of Pharmacology and Experimental Therapeutics* 280(2):988-1000, American Society for Pharmacology and Experimental Therapeutics, United States (1997).
Fluiter, K., "Filling the gap in LNA antisense oligo gapmers: the effects of unlocked nucleic acid (UNA) and 4'-C-hydroxymethyl-DNA modifications on RNase H recruitment and efficacy of an LNA gapmer," *Molecular BioSystems* 5:838-843, Royal Society of Chemistry, United Kingdom (2009).
Frank-Kamenetsky, M., et al., "Therapeutic RNAi targeting PCSK9 acutely lowers plasma cholesterol in rodents and LDL cholesterol in nonhuman primates," *PNAS* 105(33):11915-11920, National Academy of Sciences, United States (2008).
Gupta, N., et al., "A Locked Nucleic Acid Antisense Oligonucleotide (LNA) Silences PCSK9 and Enhances LDLR Expression In Vitro and In Vivo," *PLoS One* 5(5):e10682, 9 pages, Public Library of Science, United States (2010).
"Inhibition of PCSK9 as a Novel Strategy for the Treatment of Hypercholesterolemia," *Drug News Perspect.* 21(6):323-330, Prous Science, S.A.U., Spain (2008).
Seidah, N. G., "PCSK9 as a therapeutic target of dyslipidemia," *Expert Opin. Ther. Targets* 13(1):19-28, Informa UK Ltd., United Kingdom (2009).
Straarup, E.M., et al., "Short locked nucleic acid antisense oligonucleotides potently reduce apolipoprotein B mRNA and serum cholesterol in mice and non-human primates," *Nucleic Acids Research* 38(20):7100-7111, Oxford University Press, United Kingdom (2010).
NCBI Entrez, GenBank Report, Accession No. NM_174936, Chernogubova, E. et al., Entry Date Jul. 2012.
NCBI Entrez, GenBank Report, Accession No. NP_777596.2, Chernogubova, E. et al., Entry Date Jul. 2012.
International Search Report for International Application No. PCT/EP2010/059257, European Patent Office, Netherlands, dated Nov. 5, 2010.
International Search Report for International Application No. PCT/EP2009/054499, European Patent Office, Netherlands, dated Sep. 2, 2009.
Xu, Y., et al., "Effective small interfering RNAs and phosphorothioate antisense DNAs have different preferences for target sites in the luciferase mRNAs," *Biochem Biophys Res Commun.* 306(3): 712-7, Elsevier Science, USA (2003).
Bertrand, J.R., et al., "Comparison of antisense oligonucleotides and siRNAs in cell culture and in vivo," *Biochemical and Biophysical Research Communications* 296:1000-1004, Elsevier , Netherlands (2002).
Biessen, E., et al.," Targeted delivery of oligodeoxynucleotides to parenchymal liver cells in vivo," *Biochemical Journal* 340(3):15, Portland Press, United Kingdom (1999).
Burel, S.A., et al., "Preclinical Evaluation of the Toxicological Effects of a Novel Constrained Ethyl Modified Antisense Compound Targeting Signal Transducer and Activator of Transcription 3 in Mice and Cynomolgus Monkeys," *Nucleic Acid Research* 44(5):2093-2109, Oxford University Press, England (2015).
Chaltin, P., et al. ,"Delivery of antisense oligonucleotides using cholesterol-modified sense dendrimers and cationic lipids," *Bioconjugate Chemistry* 16(4):827-836, American Chemistry Society, United States(2005).
Hagedorn, P.H., et al., "Hepatotoxic Potential of Therapeutic Oligonucleotides Can Be Predicted from Their Sequence and Modification Pattern," *Nucleic Acid Therapeutics*(23):302-310, Oxford University Press, England (2013).
Henry, S.P., et al., "Toxicologic Properties of 2'O-Methoxyethyl Chimeric Antisense Inhibitors in Animals and Man," in the *Antisense Drug technology, Principles, Strategies, and Applications: Chapter 12*, Crooke, S.T., 2nd ed., pp. 327-363, CRC Press, Florida, United States (2007).

(56) References Cited

OTHER PUBLICATIONS

Henry, S.P., et al., "Activation of the Alternative Pathway of Complement by a Phosphorothioate Oligonucleotide; Potential Mechanism of Action," *Journal of Pharmacology and Experimental Therapeutics* 281(2):810-816, American Society for Pharmacology and Experimental Therapeutics, United States (1997).

Krieg, Arthur., "Targeting LDL Cholesterol with LNA," *Molecular Therapy—Nucleic Acid* 1(e6):1-2, American Society of Gene & Cell Therapy, Untied States (2012).

Lima, W.F., et al., "Structural Requirements at the Catalytic Site of the Heteroduplex Substrate for Human RNase H1 Catalysis," Journal of Biological Chemistry 279(35):36317-36326, American Society for Biochemistry and Molecular Biology, United States (2004).

Lindholm, M.W., et al., "PCSK9 LNA Antisense Oligonucleotides Induce Sustained Reduction of LDL Cholesterol in Nonhuman Primates," *Molecular Therapy* 20(2): 376-381, American Society of Gene & Cell Therapy, United States (2012).

Maier, M., et al., "Synthesis of antisense oligonucleotides conjugated to a multivalent carbohydrate cluster for cellular targeting," *Bioconjugate Chemistry* 14(1):18-29, American Chemistry Society, United States (2003).

Poelgeest, E.P., et al., "Acute Kidney Injury During Therapy With an Antisense Oligonucleotide Directed Against PCSK9," *American Journal of Kidney Dis.* 62(4):796-800, Elsevier, Netherlands (2013).

Seth, P., et al., "Design, Synthesis and Evaluation of Constrained Methoxyethyl (cMOE) and Constrained Ethyl (cEt) Nucleoside Analogs," *Nucleic Acids Symposium Series* 52:553-554, Oxford University Press, England (2008).

Soutschek, J., et al., "Therapeutic Silencing of an endogenous gene by systemic administration of modified siRNAs," *Nature* 432:173-178, Nature Publishing, United States (2004).

Su-Jun, Z., et al., "Distribution and anti-HBV effects of antisense oligodeoxynucleotides conjugated to galactosylated poly-L-lysine," *World Journal of Gastroenterology* 9(6):1, WJG Press, China (2003).

Swayze, E., et al., "Antisense oligonucleotides containing locked nucleic acid improve potency but cause significant hepatotoxicity in animals," *Nucleic Acid Research* 35(2) :687-700, Oxford University Press, England (2007).

Zhao, H., et al., "A New Platform for Oligonucleotide Delivery Utilizing the PEG Prodrug Approach," *Bioconjugate Chemistry* 16:758-766, American Chemistry Society, United States (2005).

Krutzfeldt, J., et al., "Silencing of microRNAs in vivo with 'antagomirs,'" *Nature Letters* 10.1038:1-5, Nature Publishing Group, United States (2005).

Seth, P.P., et al., "Short Antisense Oligonucleotides with Novel 2'-4' Conformational Restricted Nucleoside Analogues Show Improved Potency without Increased Toxicity in Animals," *J. Med. Chem.* 52:10-13, American Chemical Society, United States (2009).

Wallace, T.L., et al., "Single-dose hemodynamic toxicity and pharmacokinetics of a partial phosphorothioate anti-HIV oligonucleotide ($AR_{177}$) after intravenous infusion to cynomolgus monkeys," *Journal of Pharmacology and Experimental Therapeutics* 278(3):1306-1312, American Society for Pharmacology and Experimental Therapeutics, United States (1996).

International Search Report for International Application No. PCT/EP2014/063757, European Patent Office, Netherlands, dated Dec. 15, 2014.

Bhat, B., et al., "RG-101, a GalNAC-conjugated anti-miR employing a unique mechanism of action by targeting host factor microRNA-122 (miR-122), demonstrates potent activity and reduction of HCV in preclinical studies," *Hepatology* 58(6):1393A, John Wiley & Sons, United States (2013).

Manoharan, M., "Oligonucleotide Conjugates as Potential Antisense Drugs with Improved Uptake, Biodistribution, Targeted Delivery, and Mechanism of Action," *Antisense & Nucleic Acid Drug Development* 12:103-128, Mary Ann Liebert, Inc., United States (2002).

Yu, B., et al., "Targeted Delivery Systems for Oligonucleotide Therapeutics," *The AAPS Journal* 11(1):195-203, Springer Science+Business Media, Germany (2009).

Co-pending Application, U.S. Appl. No. 15/836,144, inventors Albak, N., et al., filed Dec. 8, 2017 (Not Published).

Co-pending Application, U.S. Appl. No. 15/971,951 inventors Albak, N., et al., filed May 4, 2018 (Not Published).

Juby, C.D., et al., "Facile Preparation of 3'Oligonucleotide-Peptide Conjugates," *Tetrahedron Letters* 32(7):789-882, Pergamon Press PLC, Great Britain (1991).

Office Action for European Patent Application No. 14739708.71, dated Apr. 28, 2017, European Patent Office, Netherlands, 14 pages.

Ørum, H., et al., "Locked nucleic acids: A Promising molecular family for gene-function analysis function analysis and antisense drug development," *Current Opinion in Molecular Therapeutics* 3(3):239-243, Current Drugs Ltd., United States (2001).

Van Poelgeest, E.P, et al., "Antisesen-mediated reduction of proprotein converstase subtilisin/kexin type 9 (PCSK9): a first-in-human randomized, placebo-controlled trial," *British Journal of Clinical Pharmacology* 80(6):1350-1361, British Pharmacological Society, Britain (2015).

Zheng, S.J., et al., "Distribution and anti-HBV effects of antisense oligodeoxynucleotides conjugated to galactosylated poly-L-lysine", *World J. Gastroenterol* 9(6):1251-1255, Baishideng Publishing Group, United States (2003).

Fougerolles, A.R., et al., "Discovery and Development of RNAi Therapeutics," *Chapter 16: Antisense Drug Technology: Principles, Strategies, and Applications,* $2^{nd}$ ed., Stanley T. Crooke, CRC Press, United States(2007).

* cited by examiner

Figure 1 (cont)
Conj 4=
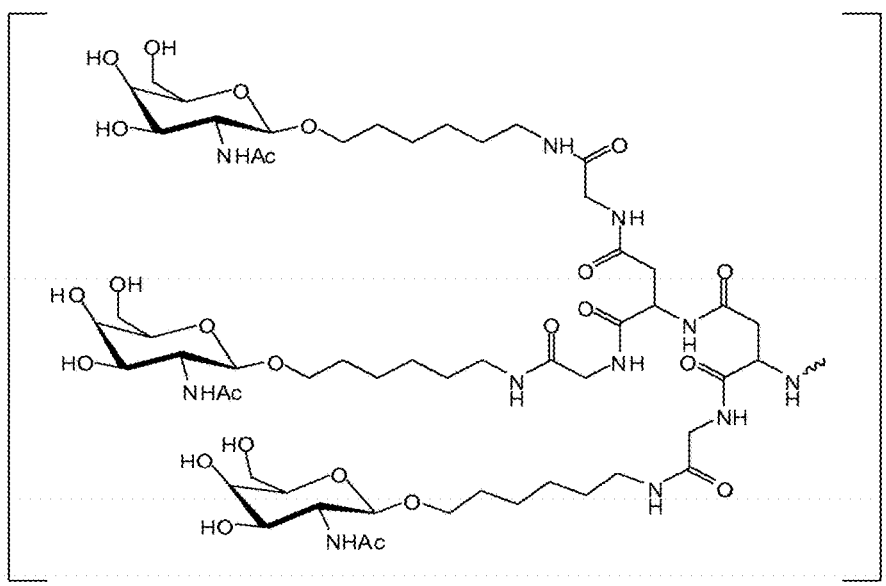
Conj 4a=
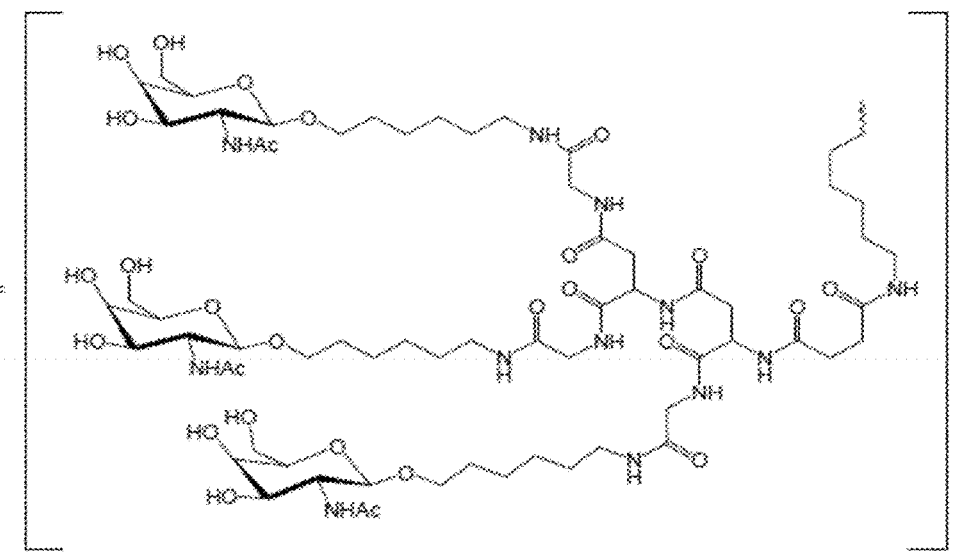

Figure 3

5'-T$^L_s$G$^L_s$$^{Me}$C$^L_s$T$_s$A$_s$C$_s$A$_s$A$_s$A$_s$A$_s$C$_s$$^{Me}$C$^L_s$$^{Me}$C$^L_s$A$^L$-3'
SEQ ID 1

5'- A$^L_s$A$^L_s$T$^L_s$G$_s$C$_s$T$_s$A$_s$C$_s$A$_s$A$_s$A$_s$A$_s$$^{Me}$C$^L_s$$^{Me}$C$^L_s$$^{Me}$C$^L_s$A$^L$-3'
SEQ ID 2

5'-A$^L_s$A$^L_s$T$^L_s$G$_s$C$_s$T$_s$A$_s$C$_s$A$_s$A$_s$A$_s$A$_s$C$_s$$^{Me}$C$^L_s$$^{Me}$C$^L_s$A$^L$-3'
SEQ ID 3

5'-G$^L_s$$^{Me}$C$^L_s$T$_s$G$_s$T$_s$G$_s$T$_s$G$_s$A$_s$G$_s$C$_s$T$_s$T$_s$G$^L_s$G$^L$-3'
SEQ ID 4

5'-T$^L_s$G$^L_s$C$_s$T$_s$G$_s$T$_s$G$_s$T$_s$G$_s$A$_s$G$_s$C$_s$T$_s$T$^L_s$G$^L_s$G$^L$-3'
SEQ ID 5

5'-T$^L_s$G$^L_s$$^{Me}$C$^L_s$T$_s$G$_s$T$_s$G$_s$T$_s$G$_s$A$_s$G$_s$C$_s$T$_s$T$^L_s$G$^L_s$G$^L$-3'
SEQ ID 6

5'-T$^L_s$$^{Me}$C$^L_s$$^{Me}$C$^L_s$T$_s$G$_s$G$_s$T$_s$C$_s$T$_s$G$_s$T$_s$G$_s$T$_s$T$^L_s$$^{Me}$C$^L_s$$^{Me}$C$^L$-3'
SEQ ID 7

5'-T$^L_s$$^{Me}$C$^L_s$$^{Me}$C$^L_s$T$_s$G$_s$G$_s$T$_s$C$_s$T$_s$G$_s$T$_s$G$_s$T$_s$T$_s$$^{Me}$C$^L_s$$^{Me}$C$^L$-3'
SEQ ID 8

Figure 4
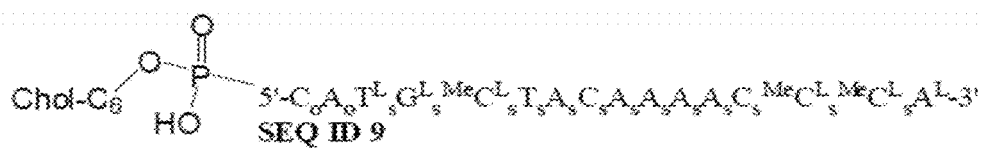
SEQ ID 9
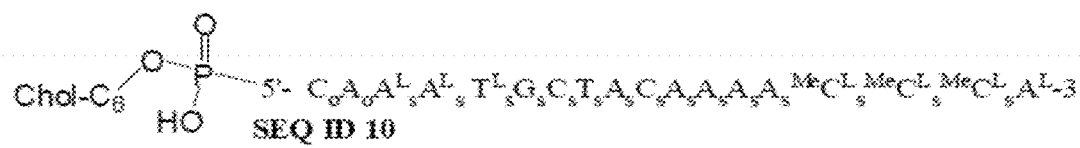
SEQ ID 10
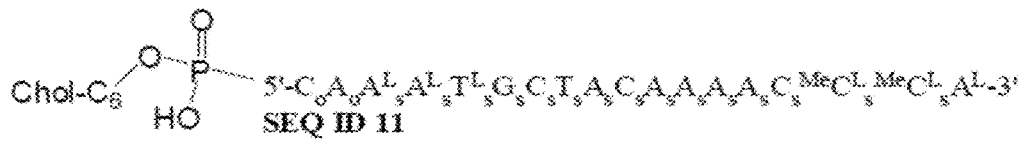
SEQ ID 11
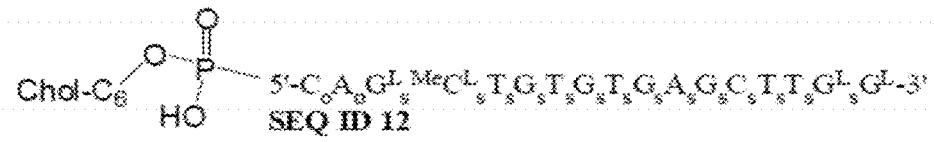
SEQ ID 12
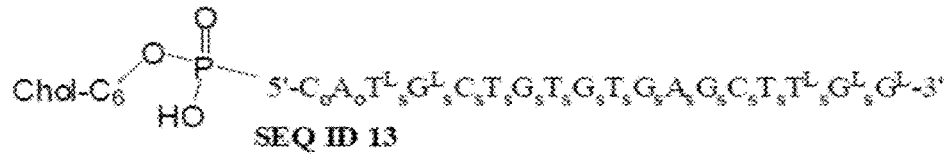
SEQ ID 13
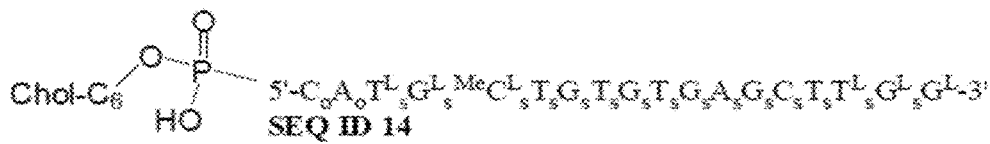
SEQ ID 14
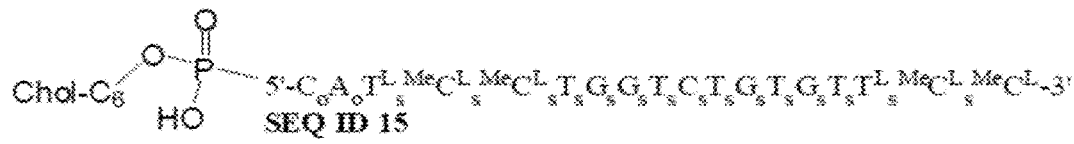
SEQ ID 15
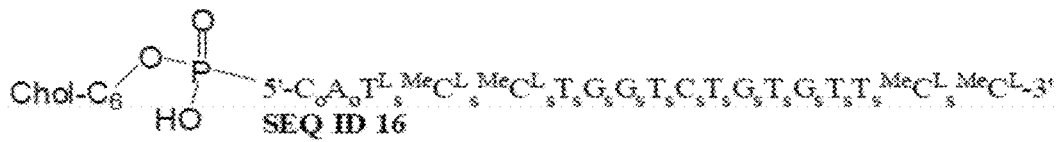
SEQ ID 16

A
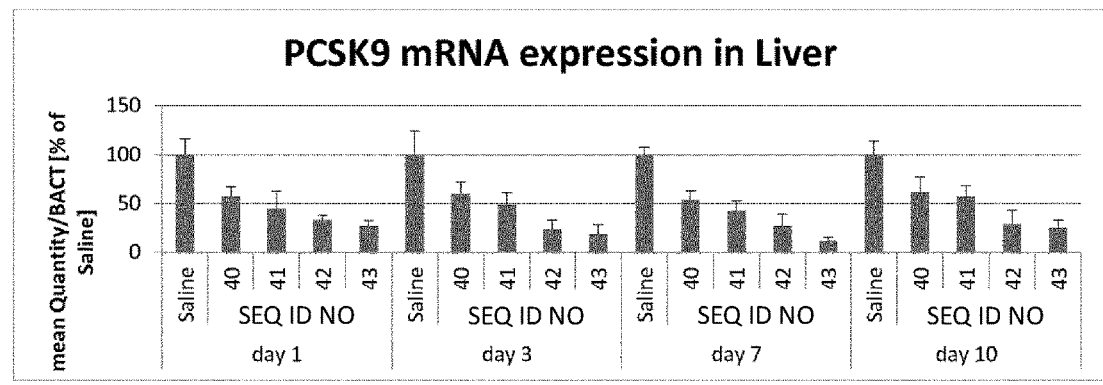
B
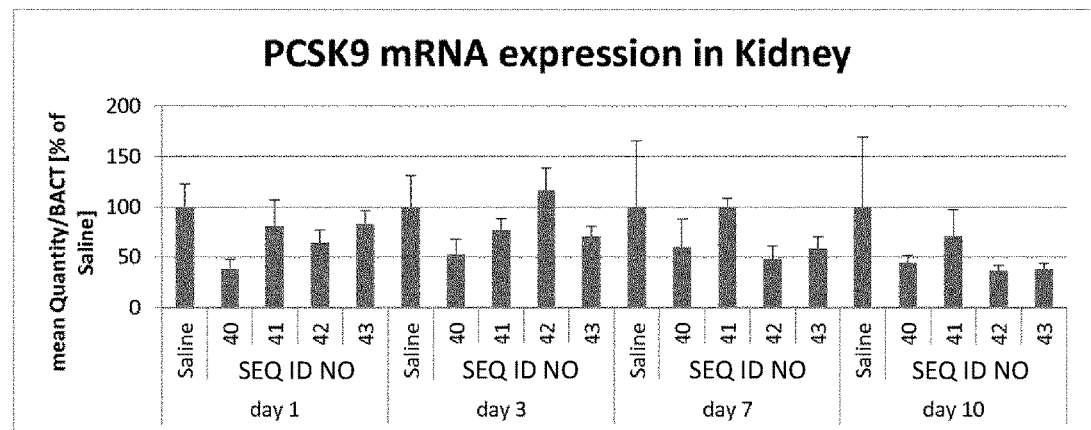
Figure 14

Figure 16 (cont)
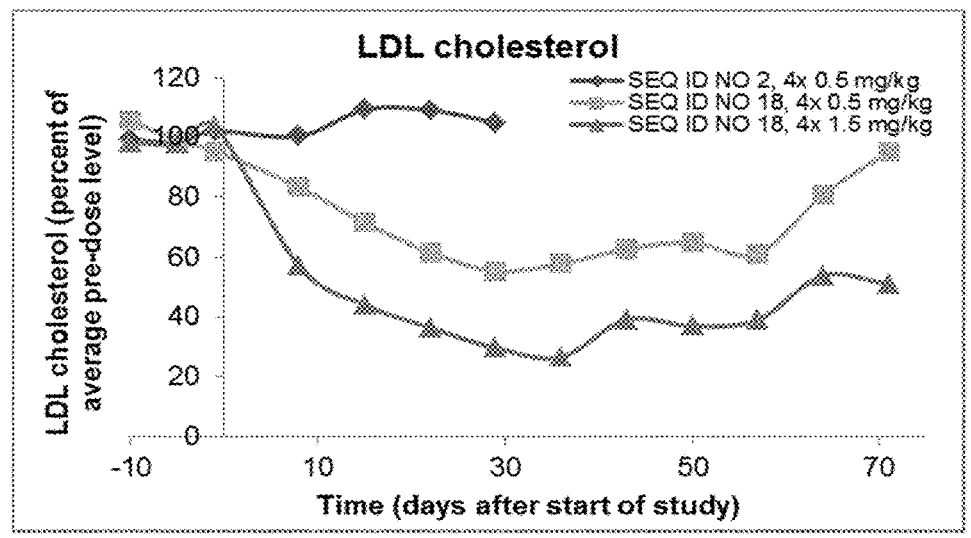
Figure 17
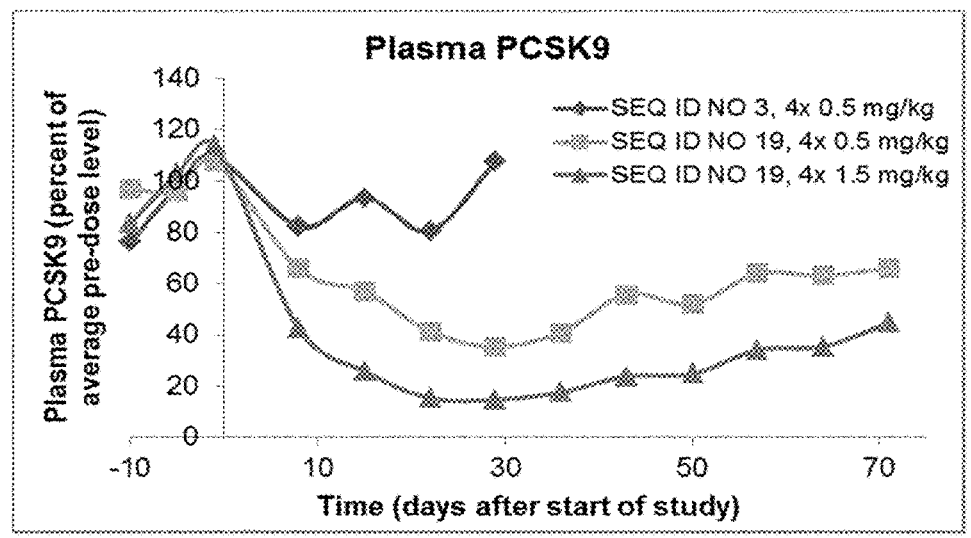
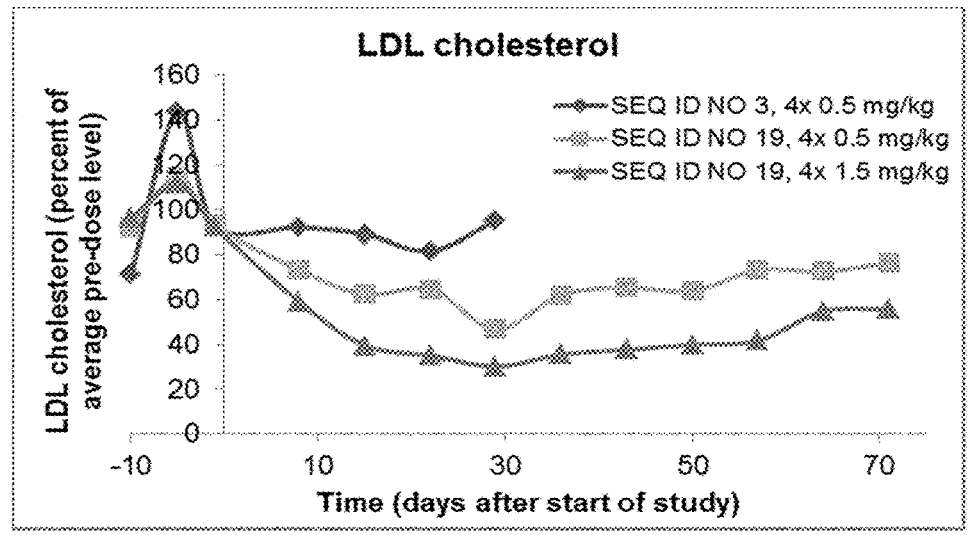

SEQUENCE LISTING

<160> NUMBER OF SEQ ID NOS: 46

<210> SEQ ID NO 1
<211> LENGTH: 14
<212> TYPE: DNA
<213> ORGANISM: ARTIFICIAL
<220> FEATURE:
<223> OTHER INFORMATION: LNA antisense gapmer oligonucleotide
<220> FEATURE:
<221> NAME/KEY: misc_feature
<222> LOCATION: (1)..(14)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (12)..(14)
<223> OTHER INFORMATION: LNA nucleosides, LNA C are 5-methyl C

<400> SEQUENCE: 1
tgctacaaaa ccca                                                        14

<210> SEQ ID NO 2
<211> LENGTH: 16
<212> TYPE: DNA
<213> ORGANISM: ARTIFICIAL
<220> FEATURE:
<223> OTHER INFORMATION: LNA antisense gapmer oligonucleotide
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides
<220> FEATURE:
<221> NAME/KEY: misc_feature
<222> LOCATION: (13)..(16)
<223> OTHER INFORMATION: LNA nucleosides, LNA C are 5-methyl C

<400> SEQUENCE: 2
aatgctacaa aaccca                                                      16

<210> SEQ ID NO 3
<211> LENGTH: 16
<212> TYPE: DNA
<213> ORGANISM: ARTIFICIAL
<220> FEATURE:
<223> OTHER INFORMATION: LNA antisense gapmer oligonucleotide
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides
<220> FEATURE:
<221> NAME/KEY: misc_feature
<222> LOCATION: (14)..(16)
<223> OTHER INFORMATION: LNA nucleosides, LNA C are 5-methyl C

<400> SEQUENCE: 3
aatgctacaa aaccca                                                      16

<210> SEQ ID NO 4
<211> LENGTH: 15
<212> TYPE: DNA
<213> ORGANISM: ARTIFICIAL

```
<220> FEATURE:
<223> OTHER INFORMATION: LNA antisense gapmer oligonucleotide
<220> FEATURE:
<221> NAME/KEY: misc_feature
<222> LOCATION: (1)..(15)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides, LNA C are 5-methyl C
<220> FEATURE:
<221> NAME/KEY: misc_feature
<222> LOCATION: (14)..(15)
<223> OTHER INFORMATION: LNA nucleosides

<400> SEQUENCE: 4
gctgtgtgag cttgg                                                    15

<210> SEQ ID NO 5
<211> LENGTH: 16
<212> TYPE: DNA
<213> ORGANISM: ARTIFICIAL
<220> FEATURE:
<223> OTHER INFORMATION: LNA antisense gapmer oligonucleotide
<220> FEATURE:
<221> NAME/KEY: misc_feature
<222> LOCATION: (1)..(2)
<223> OTHER INFORMATION: LNA nucleosides
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (14)..(16)
<223> OTHER INFORMATION: LNA nucleosides

<400> SEQUENCE: 5
tgctgtgtga gcttgg                                                   16

<210> SEQ ID NO 6
<211> LENGTH: 16
<212> TYPE: DNA
<213> ORGANISM: ARTIFICIAL
<220> FEATURE:
<223> OTHER INFORMATION: LNA antisense gapmer oligonucleotide
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (14)..(16)
<223> OTHER INFORMATION: LNA nucleosides

<400> SEQUENCE: 6
tgctgtgtga gcttgg                                                   16

<210> SEQ ID NO 7
<211> LENGTH: 16
<212> TYPE: DNA
<213> ORGANISM: ARTIFICIAL
<220> FEATURE:
<223> OTHER INFORMATION: LNA antisense gapmer oligonucleotide
<220> FEATURE:
<221> NAME/KEY: misc_feature
<222> LOCATION: (1)..(16)
<223> OTHER INFORMATION: phosphorothioate lnternucleoside linkages
<220> FEATURE:
```

```
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (14)..(16)
<223> OTHER INFORMATION: LNA nucleosides, LNA C are 5-methyl C

<400> SEQUENCE: 7
tcctggtctg tgttcc                                                      16

<210> SEQ ID NO 8
<211> LENGTH: 16
<212> TYPE: DNA
<213> ORGANISM: artificial
<220> FEATURE:
<223> OTHER INFORMATION: LNA antisense gapmer oligonucleotide
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (15)..(16)
<223> OTHER INFORMATION: LNA nucleosides, LNA C are 5-methyl C

<400> SEQUENCE: 8
tcctggtctg tgttcc                                                      16

<210> SEQ ID NO 9
<211> LENGTH: 16
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: Cholesterol-C6
<220> FEATURE:
<221> NAME/KEY: misc_feature
<222> LOCATION: (1)..(2)
<223> OTHER INFORMATION: phosphodiester lnternucleoside linkages
<220> FEATURE:
<221> NAME/KEY: misc_feature
<222> LOCATION: (3)..(16)
<223> OTHER INFORMATION: phosphorothioate lnternucleoside linkages
<220> FEATURE:
<221> NAME/KEY: misc_feature
<222> LOCATION: (3)..(5)
<223> OTHER INFORMATION: LNA nucleosides, LNA C are 5-methyl C
<220> FEATURE:
<221> NAME/KEY: misc_feature
<222> LOCATION: (14)..(16)
<223> OTHER INFORMATION: LNA nucleosides, LNA C are 5-methyl C

<400> SEQUENCE: 9
catgctacaa aaccca                                                      16

<210> SEQ ID NO 10
<211> LENGTH: 18
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: Cholesterol-C6
```

<220> FEATURE:
<221> NAME/KEY: misc_feature
<222> LOCATION: (1)..(2)
<223> OTHER INFORMATION: phosphodiester lnternucleoside linkages
<220> FEATURE:
<221> NAME/KEY: misc_feature
<222> LOCATION: (3)..(18)
<223> OTHER INFORMATION: phosphorothioate lnternucleoside linkages
<220> FEATURE:
<221> NAME/KEY: misc_feature
<222> LOCATION: (3)..(5)
<223> OTHER INFORMATION: LNA nucleosides
<220> FEATURE:
<221> NAME/KEY: misc_feature
<222> LOCATION: (15)..(18)
<223> OTHER INFORMATION: LNA nucleosides, LNA C are 5-methyl C

<400> SEQUENCE: 10
caaatgctac aaaaccca                                                18

<210> SEQ ID NO 11
<211> LENGTH: 18
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: Cholesterol-C6
<220> FEATURE:
<221> NAME/KEY: misc_feature
<222> LOCATION: (1)..(2)
<223> OTHER INFORMATION: phosphodiester lnternucleoside linkages
<220> FEATURE:
<221> NAME/KEY: misc_feature
<222> LOCATION: (3)..(18)
<223> OTHER INFORMATION: phosphorothioate lnternucleoside linkages
<220> FEATURE:
<221> NAME/KEY: misc_feature
<222> LOCATION: (3)..(5)
<223> OTHER INFORMATION: LNA nucleosides
<220> FEATURE:
<221> NAME/KEY: misc_feature
<222> LOCATION: (16)..(18)
<223> OTHER INFORMATION: LNA nucleosides, LNA C are 5-methyl C

<400> SEQUENCE: 11
caaatgctac aaaaccca                                                18

<210> SEQ ID NO 12
<211> LENGTH: 17
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: Cholesterol-C6
<220> FEATURE:
<221> NAME/KEY: misc_feature
<222> LOCATION: (1)..(2)
<223> OTHER INFORMATION: phosphodiester lnternucleoside linkages
<220> FEATURE:
<221> NAME/KEY: misc_feature
<222> LOCATION: (3)..(17)
<223> OTHER INFORMATION: phosphorothioate lnternucleoside linkages
<220> FEATURE:
<221> NAME/KEY: misc_feature
<222> LOCATION: (3)..(4)
<223> OTHER INFORMATION: LNA nucleosides, LNA C are 5-methyl C
<220> FEATURE:
<221> NAME/KEY: misc_feature
<222> LOCATION: (16)..(17)

```
<223> OTHER INFORMATION: LNA nucleosides

<400> SEQUENCE: 12
cagctgtgtg agcttgg                                                          17

<210> SEQ ID NO 13
<211> LENGTH: 18
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: Cholesterol-C6
<220> FEATURE:
<221> NAME/KEY: misc_feature
<222> LOCATION: (1)..(2)
<223> OTHER INFORMATION: phosphodiester lnternucleoside linkages
<220> FEATURE:
<221> NAME/KEY: misc_feature
<222> LOCATION: (3)..(4)
<223> OTHER INFORMATION: LNA nucleosides
<220> FEATURE:
<221> NAME/KEY: misc_feature
<222> LOCATION: (3)..(18)
<223> OTHER INFORMATION: phosphorothioate lnternucleoside linkages
<220> FEATURE:
<221> NAME/KEY: misc_feature
<222> LOCATION: (16)..(18)
<223> OTHER INFORMATION: LNA nucleosides

<400> SEQUENCE: 13
catgctgtgt gagcttgg                                                         18

<210> SEQ ID NO 14
<211> LENGTH: 18
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: Cholesterol-C6
<220> FEATURE:
<221> NAME/KEY: misc_feature
<222> LOCATION: (1)..(2)
<223> OTHER INFORMATION: phosphodiester lnternucleoside linkages
<220> FEATURE:
<221> NAME/KEY: misc_feature
<222> LOCATION: (3)..(18)
<223> OTHER INFORMATION: phosphorothioate lnternucleoside linkages
<220> FEATURE:
<221> NAME/KEY: misc_feature
<222> LOCATION: (3)..(5)
<223> OTHER INFORMATION: LNA nucleosides, LNA C are 5-methyl C
<220> FEATURE:
<221> NAME/KEY: misc_feature
<222> LOCATION: (16)..(18)
<223> OTHER INFORMATION: LNA nucleosides

<400> SEQUENCE: 14
catgctgtgt gagcttgg                                                         18

<210> SEQ ID NO 15
<211> LENGTH: 18
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
```

```
<222> LOCATION: (1)..(1)
<223> OTHER INFORMATION: Cholesterol-C6
<220> FEATURE:
<221> NAME/KEY: misc_feature
<222> LOCATION: (1)..(2)
<223> OTHER INFORMATION: phosphodiester lnternucleoside linkages
<220> FEATURE:
<221> NAME/KEY: misc_feature
<222> LOCATION: (3)..(18)
<223> OTHER INFORMATION: phosphorothioate lnternucleoside linkages
<220> FEATURE:
<221> NAME/KEY: misc_feature
<222> LOCATION: (3)..(5)
<223> OTHER INFORMATION: LNA nucleosides, LNA C are 5-methyl C
<220> FEATURE:
<221> NAME/KEY: misc_feature
<222> LOCATION: (16)..(18)
<223> OTHER INFORMATION: LNA nucleosides, LNA C are 5-methyl C

<400> SEQUENCE: 15
catcctggtc tgtgttcc                                                18

<210> SEQ ID NO 16
<211> LENGTH: 18
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: Cholesterol-C6
<220> FEATURE:
<221> NAME/KEY: misc_feature
<222> LOCATION: (1)..(2)
<223> OTHER INFORMATION: phosphodiester lnternucleoside linkages
<220> FEATURE:
<221> NAME/KEY: misc_feature
<222> LOCATION: (3)..(18)
<223> OTHER INFORMATION: phosphorothioate lnternucleoside linkages
<220> FEATURE:
<221> NAME/KEY: misc_feature
<222> LOCATION: (3)..(5)
<223> OTHER INFORMATION: LNA nucleosides, LNA C are 5-methyl C
<220> FEATURE:
<221> NAME/KEY: misc_feature
<222> LOCATION: (17)..(18)
<223> OTHER INFORMATION: LNA nucleosides, LNA C are 5-methyl C

<400> SEQUENCE: 16
catcctggtc tgtgttcc                                                18

<210> SEQ ID NO 17
<211> LENGTH: 14
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: GalNAc Conj2a
<220> FEATURE:
<221> NAME/KEY: misc_feature
<222> LOCATION: (1)..(14)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (12)..(14)
<223> OTHER INFORMATION: LNA nucleosides, LNA C are 5-methyl C
```

-continued

```
<400> SEQUENCE: 17
tgctacaaaa ccca                                                    14

<210> SEQ ID NO 18
<211> LENGTH: 16
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: GalNAc Conj2a
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides
<220> FEATURE:
<221> NAME/KEY: misc_feature
<222> LOCATION: (13)..(16)
<223> OTHER INFORMATION: LNA nucleosides, LNA C are 5-methyl C

<400> SEQUENCE: 18
aatgctacaa aaccca                                                  16

<210> SEQ ID NO 19
<211> LENGTH: 16
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: GalNAc Conj2a
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides
<220> FEATURE:
<221> NAME/KEY: misc_feature
<222> LOCATION: (14)..(16)
<223> OTHER INFORMATION: LNA nucleosides, LNA C are 5-methyl C

<400> SEQUENCE: 19
aatgctacaa aaccca                                                  16

<210> SEQ ID NO 20
<211> LENGTH: 15
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: GalNAc Conj2a
<220> FEATURE:
<221> NAME/KEY: misc_feature
<222> LOCATION: (1)..(15)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides, LNA C are 5-methyl C
```

```
<220> FEATURE:
<221> NAME/KEY: misc_feature
<222> LOCATION: (14)..(15)
<223> OTHER INFORMATION: LNA nucleosides

<400> SEQUENCE: 20
gctgtgtgag cttgg                                                      15

<210> SEQ ID NO 21
<211> LENGTH: 16
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: GalNAc Conj2a
<220> FEATURE:
<221> NAME/KEY: misc_feature
<222> LOCATION: (1)..(2)
<223> OTHER INFORMATION: LNA nucleosides
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (14)..(16)
<223> OTHER INFORMATION: LNA nucleosides

<400> SEQUENCE: 21
tgctgtgtga gcttgg                                                     16

<210> SEQ ID NO 22
<211> LENGTH: 16
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: GalNAc Conj2a
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (14)..(16)
<223> OTHER INFORMATION: LNA nucleosides

<400> SEQUENCE: 22
tgctgtgtga gcttgg                                                     16

<210> SEQ ID NO 23
<211> LENGTH: 16
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: GalNAc Conj2a
<220> FEATURE:
<221> NAME/KEY: misc_feature
<222> LOCATION: (1)..(16)
```

```
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (14)..(16)
<223> OTHER INFORMATION: LNA nucleosides, LNA C are 5-methyl C

<400> SEQUENCE: 23
tcctggtctg tgttcc                                                     16

<210> SEQ ID NO 24
<211> LENGTH: 16
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: GalNAc Conj2a
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (15)..(16)
<223> OTHER INFORMATION: LNA nucleosides, LNA C are 5-methyl C

<400> SEQUENCE: 24
tcctggtctg tgttcc                                                     16

<210> SEQ ID NO 25
<211> LENGTH: 14
<212> TYPE: DNA
<213> ORGANISM: Artificial Sequence
<220> FEATURE:
<223> OTHER INFORMATION: nucleobase sequence motif

<400> SEQUENCE: 25
tgctacaaaa ccca                                                       14

<210> SEQ ID NO 26
<211> LENGTH: 16
<212> TYPE: DNA
<213> ORGANISM: ARTIFICIAL
<220> FEATURE:
<223> OTHER INFORMATION: nucleobase sequence motif

<400> SEQUENCE: 26
aatgctacaa aaccca                                                     16

<210> SEQ ID NO 27
<211> LENGTH: 15
<212> TYPE: DNA
<213> ORGANISM: ARTIFICIAL
<220> FEATURE:
<223> OTHER INFORMATION: nucleobase sequence motif

<400> SEQUENCE: 27
gctgtgtgag cttgg                                                      15
```

```
<210> SEQ ID NO 28
<211> LENGTH: 16
<212> TYPE: DNA
<213> ORGANISM: ARTIFICIAL
<220> FEATURE:
<223> OTHER INFORMATION: nucleobase sequence motif

<400> SEQUENCE: 28
tgctgtgtga gcttgg                                                   16

<210> SEQ ID NO 29
<211> LENGTH: 16
<212> TYPE: DNA
<213> ORGANISM: ARTIFICIAL
<220> FEATURE:
<223> OTHER INFORMATION: nucleobase sequence motif

<400> SEQUENCE: 29
tcctggtctg tgttcc                                                   16

<210> SEQ ID NO 30
<211> LENGTH: 14
<212> TYPE: RNA
<213> ORGANISM: Homo sapiens

<400> SEQUENCE: 30
uggguuuugu agca                                                     14

<210> SEQ ID NO 31
<211> LENGTH: 16
<212> TYPE: RNA
<213> ORGANISM: Homo sapiens

<400> SEQUENCE: 31
uggguuuugu agcauu                                                   16

<210> SEQ ID NO 32
<211> LENGTH: 15
<212> TYPE: RNA
<213> ORGANISM: Homo sapiens

<400> SEQUENCE: 32
ccaagcucac acagc                                                    15

<210> SEQ ID NO 33
<211> LENGTH: 16
<212> TYPE: RNA
<213> ORGANISM: Homo sapiens

<400> SEQUENCE: 33
ccaagcucac acagca                                                   16

<210> SEQ ID NO 34
<211> LENGTH: 16
<212> TYPE: RNA
<213> ORGANISM: Homo sapiens

<400> SEQUENCE: 34
ggaacacaga ccagga                                                   16

<210> SEQ ID NO 35
<211> LENGTH: 16
<212> TYPE: DNA
<213> ORGANISM: artificial
<220> FEATURE:
```

```
<223> OTHER INFORMATION: LNA antisense gapmer oligonucleotide conjugate
<220> FEATURE:
<221> NAME/KEY: misc_feature
<222> LOCATION: (1)..(3)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: FAM conjugate
<220> FEATURE:
<221> NAME/KEY: misc_feature
<222> LOCATION: (4)..(16)
<223> OTHER INFORMATION: phosphorothioate lnternucleoside linkages
<220> FEATURE:
<221> NAME/KEY: misc_feature
<222> LOCATION: (4)..(5)
<223> OTHER INFORMATION: LNA nucleosides, LNA C are 5-methyl C
<220> FEATURE:
<221> NAME/KEY: misc_feature
<222> LOCATION: (14)..(16)
<223> OTHER INFORMATION: LNA nucleosides, LNA C are 5-methyl C

<400> SEQUENCE: 35
tcagcattgg tattca                                                     16

<210> SEQ ID NO 36
<211> LENGTH: 15
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(2)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: FAM conjugate
<220> FEATURE:
<221> NAME/KEY: misc_feature
<222> LOCATION: (3)..(15)
<223> OTHER INFORMATION: phosphorothioate lnternucleoside linkages
<220> FEATURE:
<221> NAME/KEY: misc_feature
<222> LOCATION: (3)..(4)
<223> OTHER INFORMATION: LNA nucleosides, LNA C are 5-methyl C
<220> FEATURE:
<221> NAME/KEY: misc_feature
<222> LOCATION: (13)..(15)
<223> OTHER INFORMATION: LNA nucleosides, LNA C are 5-methyl C

<400> SEQUENCE: 36
cagcattggt attca                                                      15

<210> SEQ ID NO 37
<211> LENGTH: 14
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: FAM conjugate
<220> FEATURE:
<221> NAME/KEY: misc_feature
<222> LOCATION: (2)..(14)
<223> OTHER INFORMATION: phosphorothioate lnternucleoside linkages
<220> FEATURE:
<221> NAME/KEY: misc_feature
```

```
<222> LOCATION: (2)..(3)
<223> OTHER INFORMATION: LNA nucleosides, LNA C are 5-methyl C
<220> FEATURE:
<221> NAME/KEY: misc_feature
<222> LOCATION: (12)..(14)
<223> OTHER INFORMATION: LNA nucleosides, LNA C are 5-methyl C

<400> SEQUENCE: 37
agcattggta ttca                                                       14

<210> SEQ ID NO 38
<211> LENGTH: 16
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(3)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: FAM conjugate
<220> FEATURE:
<221> NAME/KEY: misc_feature
<222> LOCATION: (4)..(16)
<223> OTHER INFORMATION: phosphorothioate lnternucleoside linkages
<220> FEATURE:
<221> NAME/KEY: misc_feature
<222> LOCATION: (4)..(5)
<223> OTHER INFORMATION: LNA nucleosides, LNA C are 5-methyl C
<220> FEATURE:
<221> NAME/KEY: misc_feature
<222> LOCATION: (14)..(16)
<223> OTHER INFORMATION: LNA nucleosides, LNA C are 5-methyl C

<400> SEQUENCE: 38
gacgcattgg tattca                                                     16

<210> SEQ ID NO 39
<211> LENGTH: 13
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides, LNA C are 5-methyl C
<220> FEATURE:
<221> NAME/KEY: misc_feature
<222> LOCATION: (1)..(1)
<223> OTHER INFORMATION: FAM conjugate
<220> FEATURE:
<221> NAME/KEY: misc_feature
<222> LOCATION: (11)..(13)
<223> OTHER INFORMATION: LNA nucleosides, LNA C are 5-methyl C

<400> SEQUENCE: 39
gcattggtat tca                                                        13

<210> SEQ ID NO 40
<211> LENGTH: 13
<212> TYPE: DNA
<213> ORGANISM: artificial
<220> FEATURE:
<223> OTHER INFORMATION: LNA antisense gapmer oligonucleotide
<220> FEATURE:
```

```
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides
<220> FEATURE:
<221> NAME/KEY: misc_feature
<222> LOCATION: (11)..(13)
<223> OTHER INFORMATION: LNA nucleosides, LNA C are 5-methyl C

<400> SEQUENCE: 40
gtctgtggaa gcg                                                          13

<210> SEQ ID NO 41
<211> LENGTH: 13
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: Cholesterol-C6
<220> FEATURE:
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides
<220> FEATURE:
<221> NAME/KEY: misc_feature
<222> LOCATION: (11)..(13)
<223> OTHER INFORMATION: LNA nucleosides, LNA C are 5-methyl C

<400> SEQUENCE: 41
gtctgtggaa gcg                                                          13

<210> SEQ ID NO 42
<211> LENGTH: 15
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: Cholesterol-C6
<220> FEATURE:
<221> NAME/KEY: misc_feature
<222> LOCATION: (1)..(2)
<223> OTHER INFORMATION: phosphodiester lnternucleoside linkages
<220> FEATURE:
<221> NAME/KEY: misc_feature
<222> LOCATION: (3)..(4)
<223> OTHER INFORMATION: LNA nucleosides
<220> FEATURE:
<221> NAME/KEY: misc_feature
<222> LOCATION: (3)..(15)
<223> OTHER INFORMATION: phosphorothioate lnternucleoside linkages
<220> FEATURE:
<221> NAME/KEY: misc_feature
<222> LOCATION: (13)..(15)
<223> OTHER INFORMATION: LNA nucleosides, LNA C are 5-methyl C

<400> SEQUENCE: 42
cagtctgtgg aagcg                                                        15

<210> SEQ ID NO 43
<211> LENGTH: 15
```

```
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: Cholesterol-C6
<220> FEATURE:
<221> NAME/KEY: misc_feature
<222> LOCATION: (1)..(2)
<223> OTHER INFORMATION: phosphodiester lnternucleoside linkages
<220> FEATURE:
<221> NAME/KEY: misc_feature
<222> LOCATION: (3)..(4)
<223> OTHER INFORMATION: LNA nucleosides
<220> FEATURE:
<221> NAME/KEY: misc_feature
<222> LOCATION: (3)..(15)
<223> OTHER INFORMATION: phosphorothioate lnternucleoside linkages
<220> FEATURE:
<221> NAME/KEY: misc_feature
<222> LOCATION: (13)..(15)
<223> OTHER INFORMATION: LNA nucleosides, LNA C are 5-methyl C

<400> SEQUENCE: 43
ctgtctgtgg aagcg                                                    15

<210> SEQ ID NO 44
<211> LENGTH: 13
<212> TYPE: DNA
<213> ORGANISM: artificial
<220> FEATURE:
<223> OTHER INFORMATION: nucleobase sequence motif

<400> SEQUENCE: 44
gtctgtggaa gcg                                                      13

<210> SEQ ID NO 45
<211> LENGTH: 13
<212> TYPE: RNA
<213> ORGANISM: Homo sapiens

<400> SEQUENCE: 45
cgcuuccaca gac                                                      13

<210> SEQ ID NO 46
<211> LENGTH: 3731
<212> TYPE: DNA
<213> ORGANISM: homo sapiens

<400> SEQUENCE: 46
gtccgatggg gctctggtgg cgtgatctgc gcgccccagg cgtcaagcac ccacaccta     60 gaaggtttcc gcagcgacgt cgaggcgctc atggttgcag gcgggcgccg ccgttcagtt   120
cagggtctga gcctggagga gtgagccagg cagtgagact ggctcgggcg ggccgggacg   180
cgtcgttgca gcagcggctc ccagctccca gccaggattc cgcgcgcccc ttcacgcgcc   240
ctgctcctga acttcagctc ctgcacagtc ctccccaccg caaggctcaa ggcgccgccg   300
gcgtggaccg cgcacggcct ctaggtctcc tcgccaggac agcaacctct ccctggccc    360 tcatgggcac cgtcagctcc aggcggtcct ggtggccgct gccactgctg ctgctgctgc   420
tgctgctcct gggtcccgcg ggcgcccgtg cgcaggagga cgaggacggc gactacgagg   480
agctggtgct agccttgcgt tccgaggagg acgcctggc cgaagcaccc gagcacggaa    540
ccacagccac cttccaccgc tgcgccaagg atccgtggag gttgcctggc acctacgtgg   600
```

```
tggtgctgaa ggaggagacc cacctctcgc agtcagagcg cactgcccgc cgcctgcagg    660
cccaggctgc ccgccgggga tacctcacca agatcctgca tgtcttccat ggccttcttc    720
ctggcttcct ggtgaagatg agtggcgacc tgctggagct ggcctttgaag ttgccccatg   780 tcgactacat cgaggaggac tcctctgtct ttgcccagag catcccgtgg aacctggagc    840
ggattacccc tccacggtac cgggcggatg aataccagcc ccccgacgga ggcagcctgg    900
tggaggtgta tctcctagac accagcatac agagtgacca ccgggaaatc gagggcaggg    960
tcatggtcac cgacttcgag aatgtgcccg aggaggacgg gacccgcttc cacagacagg   1020
ccagcaagtg tgacagtcat ggcacccacc tggcaggggt ggtcagcggc cgggatgccg   1080
gcgtggccaa gggtgccagc atgcgcagcc tgcgcgtgct caactgccaa gggaagggca   1140
cggttagcgg caccctcata ggcctggagt ttattcggaa aagccagctg gtccagcctg   1200
tggggccact ggtggtgctg ctgcccctgg cgggtgggta cagccgcgtc ctcaacgccg   1260
cctgccagcg cctggcgagg gctggggtcg tgctggtcac cgctgccggc aacttccggg   1320
acgatgcctg cctctactcc ccagcctcag ctcccgaggt catcacagtt ggggccacca   1380
atgcccaaga ccagccggtg accctgggga cttttgggga caactttggc cgctgtgtgg   1440 acctcttttgc cccaggggag gacatcattg gtgcctccag cgactgcagc acctgctttg   1500
tgtcacagag tgggacatca caggctgctg cccacgtggc tggcattgca gccatgatgc   1560
tgtctgccga gccggagctc accctggccg agttgaggca gagactgatc cacttctctg   1620
ccaaagatgt catcaatgag gcctggttcc ctgaggacca gcgggtactg acccccaacc   1680
tggtggccgc cctgcccccc agcacccatg gggcaggttg gcagctgttt tgcaggactg   1740
tatggtcagc acactcgggg cctacacgga tggccacagc cgtcgcccgc tgcgccccag   1800
atgaggagct gctgagctgc tccagtttct ccaggagtgg gaagcggcgg ggcgagcgca   1860
tggaggccca aggggcaag ctggtctgcc gggcccacaa cgcttttggg ggtgagggtg    1920
tctacgccat tgccaggtgc tgcctgctac cccaggccaa ctgcagcgtc cacacagctc   1980
caccagctga ggccagcatg gggacccgtg tccactgcca ccaacagggc cacgtcctca   2040
caggctgcag ctcccactgg gaggtggagg accttggcac ccacaagccg cctgtgctga   2100
ggccacgagg tcagcccaac cagtgcgtgg ccacaggga ggccagcatc cacgcttcct    2160
gctgccatgc cccaggtctg gaatgcaaag tcaaggagca tggaatcccg gcccctcagg   2220
agcaggtgac cgtggcctgc gaggagggct ggaccctgac tggctgcagt gccctccctg   2280
ggacctccca cgtcctgggg gcctacgccg tagacaacac gtgtgtagtc aggagccggg   2340
acgtcagcac tacaggcagc accagcgaag gggccgtgac agccgttgcc atctgctgcc   2400
ggagccggca cctggcgcag gcctcccagg agctccagtg acagccccat cccaggatgg   2460
gtgtctgggg agggtcaagg gctggggctg agctttaaaa tggttccgac ttgtccctct   2520
ctcagccctc catggcctgg cacgagggga tggggatgct tccgcctttc cggggctgct   2580
ggcctggccc ttgagtgggg cagcctcctt gcctggaact cactcactct gggtgcctcc   2640
tccccaggtg gaggtgccag gaagctccct ccctcactgt ggggcatttc accattcaaa   2700
caggtcgagc tgtgctcggg tgctgccagc tgctcccaat gtgccgatgt ccgtgggcag   2760
aatgactttt attgagctct tgttccgtgc caggcattca atcctcaggt ctccaccaag   2820
gaggcaggat tcttcccatg gatagggag ggggcggtag gggctgcagg acaaacatc     2880 gttgggggt gagtgtgaaa ggtgctgatg gccctcatct ccagctaact gtggagaagc   2940
ccctgggggc tccctgatta atggaggctt agctttctgg atggcatcta gccagaggct   3000
```

```
ggagacaggt gcgccctgg tggtcacagg ctgtgccttg gtttcctgag ccacctttac    3060
tctgctctat gccaggctgt gctagcaaca cccaaaggtg gcctgcgggg agccatcacc    3120
taggactgac tcggcagtgt gcagtggtgc atgcactgtc tcagccaacc cgctccacta    3180
cccggcaggg tacacattcg caccoctact tcacagagga agaaacctgg aaccagaggg    3240
ggcgtgcctg ccaagctcac acagcaggaa ctgagccaga aacgcagatt gggctggctc    3300
tgaagccaag cctcttctta cttcacccgg ctgggctcct cattttttacg ggtaacagtg    3360 aggctgggaa ggggaacaca gaccaggaag ctcggtgagt gatggcagaa cgatgcctgc    3420
aggcatggaa cttttccgt  tatcacccag gcctgattca ctggcctggc ggagatgctt    3480
ctaaggcatg gtcgggggag agggccaaca actgtccctc cttgagcacc agcccacc     3540 aagcaagcag acatttatct tttgggtctg tcctctctgt tgccttttta cagccaactt    3600
ttctagacct gttttgcttt tgtaacttga agatatttat tctgggtttt gtagcatttt    3660
tattaatatg gtgacttttt aaaataaaaa caaacaaacg ttgtcctaac aaaaaaaaaa    3720
aaaaaaaaaa a                                                         3731
```

METHODS OF TREATMENT USING ANTISENSE OLIGOMERS AND CONJUGATES TARGETING PCSK9

RELATED APPLICATIONS

This application is a continuation of U.S. application Ser. No. 15/836,144, filed Dec. 8, 2017, which is a continuation of U.S. application Ser. No. 14/897,223, filed Dec. 9, 2015, which was the National Stage under 35 C.F.R. § 371 of International Application No. PCT/EP2014/063757, filed Jun. 27, 2014, which claims the benefit of EP Application No. 13174092.0, filed Jun. 27, 2013, EP Application No. 13192930.9, filed Nov. 14, 2013, EP Application No. 13192938.2, filed Nov. 14, 2013, EP Application No. 14153253.1, filed Jan. 30, 2014, EP Application No. 14168331.8, filed May 14, 2014, and International Application No. PCT/EP2013/073858, filed Nov. 14, 2013, all of which are incorporated herein by reference in their entireties.

REFERENCE TO SEQUENCE LISTING SUBMITTED ELECTRONICALLY VIA EFS-WEB

The content of the electronically submitted sequence listing (Name: 4009.0030008_Sequence_listing_ST25.txt; Size: 26,491 bytes; and Date of Creation: May 4, 2018) filed with the application is incorporated herein by reference in its entirety.

FIELD OF INVENTION

The present invention relates to oligomeric compounds and conjugates thereof that target Proprotein Convertase Subtilisin/Kexin type 9 (PCSK9) mRNA in a cell, leading to reduced expression of PCSK9. Reduction of PCSK9 expression is beneficial for a range of medical disorders, such as hypercholesterolemia and related disorders.

BACKGROUND

Proprotein convertase subtilisin/kexin type 9 (PCSK9) has emerged as a therapeutic target for the reduction of low-density lipoprotein cholesterol (LDL-C). PCSK9 increases the degradation of the LDL receptor, resulting in high LDL-C in individuals with high PCSK9 activity.

Lindholm et al., Molecular Therapy (2012); 20 2, 376-381 reports on two LNA antisense oligonucleotides targeting PCSK9 that produce sustained reduction of LDL-C in non-human primates after a loading dose (20 mg/kg) and four weekly maintenance doses (5 mg/kg). The compounds used were a 14mer SPC5001 (SEQ ID NO 1) and a 13mer SPC4061. SPC5001 is likewise disclosed in WO2011/009697. The efficacy of these PCSK9 inhibitors has been attributed to their short length (Krieg et al., Molecular Therapy Nucleic Acids (2012) 1, e6).

WO2007/146511 reports on short bicyclic (LNA) gapmer antisense oligonucleotides which apparently are more potent and less toxic than longer compounds. The exemplified compounds appear to be 14 nts in length.

According to van Poelgeest et al., (American Journal of Kidney Disease, 2013 October; 62(4):796-800), the administration of LNA antisense oligonucleotide SPC5001 in human clinical trials may result in acute kidney injury.

According to EP 1 984 381B1, Seth et al., Nucleic Acids Symposium Series 2008 No. 52 553-554 and Swayze et al., Nucleic Acid Research 2007, vol 35, pp687-700, LNA oligonucleotides cause significant hepatotoxicity in animals. According to WO2007/146511, the toxicity of LNA oligonucleotides may be avoided by using LNA gapmers as short as 12-14 nucleotides in length. EP 1 984 381 B1 recommends using 6' substituted bicyclic nucleotides to decrease the hepatotoxicity potential of LNA oligonucleotides. According to Hagedorn et al., Nucleic Acid Therapeutics 2013, the hepatotoxic potential of antisense oligonucleotide may be predicted from their sequence and modification pattern.

Oligonucleotide conjugates have been extensively evaluated for use in siRNAs, where they are considered essential in order to obtain sufficient in vivo potency. For example, see WO2004/044141 refers to modified oligomeric compounds that modulate gene expression via an RNA interference pathway. The oligomeric compounds include one or more conjugate moieties that can modify or enhance the pharmacokinetic and pharmacodynamic properties of the attached oligomeric compound.

WO2012/083046 reports on a galactose cluster-pharmacokinetic modulator targeting moiety for siRNAs.

In contrast, single stranded antisense oligonucleotides are typically administered therapeutically without conjugation or formulation. The main target tissues for antisense oligonucleotides are the liver and the kidney, although a wide range of other tissues are also accessible by the antisense modality, including lymph node, spleen, and bone marrow.

WO 2005/086775 refers to targeted delivery of therapeutic agents to specific organs using a therapeutic chemical moiety, a cleavable linker and a labeling domain. The cleavable linker may be, for example, a disulfide group, a peptide or a restriction enzyme cleavable oligonucleotide domain.

WO 2011/126937 refers to targeted intracellular delivery of oligonucleotides via conjugation with small molecule ligands.

WO2009/025669 refers to polymeric (polyethylene glycol) linkers containing pyridyl disulphide moieties. See also Zhao et al., Bioconjugate Chem. 2005 16 758-766.

Chaltin et al., Bioconjugate Chem. 2005 16 827-836 reports on cholesterol modified mono- di- and tetrameric oligonucleotides used to incorporate antisense oligonucleotides into cationic liposomes, to produce a dendrimeric delivery system. Cholesterol is conjugated to the oligonucleotides via a lysine linker.

Other non-cleavable cholesterol conjugates have been used to target siRNAs and antagomirs to the liver—see for example, Soutscheck et al., Nature 2004 vol. 432 173-178 and Krützfeldt et al., Nature 2005 vol 438, 685-689. For the partially phosphorothiolated siRNAs and antagomirs, the use of cholesterol as a liver targeting entity was found to be essential for in vivo activity.

OBJECTIVE OF THE INVENTION

There is therefore a need for PCSK9 targeting antisense compounds, which are as effective as SPC5001, but have a reduced toxicity risk, in particular reduced kidney toxicity.

According to the present invention this has been achieved by identification of new human PCSK9 sequences which are particularly effective to target using the antisense approach (SEQ ID NO 33 and SEQ ID NO 34), as well as longer variants of the SPC5001 sequence which retain or are improved over the remarkable potency of SPC5001 without toxicity issues. The antisense oligonucleotides of the invention may be further improved by using conjugates, which have been found to greatly enhance the therapeutic index of LNA antisense oligonucleotides.

The compounds of the present invention are potent and non-toxic inhibitors of PCSK9, useful for in treatment of hypercholesterolemia and related disorders.

SUMMARY OF INVENTION

The oligomer of the invention may comprise between 10-22, such as 12-18 nucleotides in length, which either comprises a) contiguous sequence of 10-16 nucleotides which are complementary to a corresponding length of SEQ ID NO 33 or 34 or 45, or b) a contiguous sequence of 16 nucleotides which are complementary to a corresponding length of SEQ ID NO 31.

The invention provides for an antisense oligonucleotide conjugate comprising the oligomer according to the invention, and at least one non-nucleotide or non-polynucleotide moiety covalently attached to said oligomer.

The invention also provides for an antisense oligonucleotide conjugate comprising the oligomer (A) according to the invention, and at least one non-nucleotide or non-polynucleotide moiety covalently attached to said oligomer (C), optionally via a linker region (B and/or Y) positioned between the contiguous sequence of the oligomer and the conjugate moiety.

In some embodiments, the invention also provides for an antisense oligonucleotide conjugate comprising an oligomer of 10-22, such as 12-18 nucleotides in length, wherein said oligomer comprises a) a contiguous sequence of 10-16 nucleotides which are complementary to a corresponding length of SEQ ID NO 33 or 34, or 45 or b) a contiguous sequence of 16 nucleotides which are complementary to a corresponding length of SEQ ID NO 31.

The invention also provides for a compound selected from the group consisting of SEQ ID NO 2, 3, 4, 5, 6, 7, 8, 9, 10, 11, 12, 13, 14, 15, 17, 16, 18, 19, 20, 21, 22, 23, and 24.

The invention provides for a pharmaceutical composition comprising the oligomer or the conjugate according to the invention, and a pharmaceutically acceptable diluent, carrier, salt or adjuvant.

The invention provides for an oligomer or conjugate or pharmaceutical composition according to the invention, for use as a medicament, such as for the treatment of hypercholesterolemia or related disorder, such as a disorder selected from the group consisting of atherosclerosis, hyperlipidemia, hypercholesterolemia, familiar hypercholesterolemia e.g. gain of function mutations in PCSK9, HDL/LDL cholesterol imbalance, dyslipidemias, e.g., familial hyperlipidemia (FCHL) orfamilial hypercholesterolemia (FHC), acquired hyperlipidemia, statin-resistant hypercholesterolemia, coronary artery disease (CAD), and coronary heart disease (CHD).

The invention provides for the use of an oligomer or conjugate or pharmaceutical composition of the invention, for the manufacture of a medicament for the treatment of hypercholesterolemia or a related disorder, such as a disorder selected from the group consisting of atherosclerosis, hyperlipidemia, hypercholesterolemia, familiar hypercholesterolemia e.g. gain of function mutations in PCSK9, HDL/LDL cholesterol imbalance, dyslipidemias, e.g., familial hyperlipidemia (FCHL) or familial hypercholesterolemia (FHC), acquired hyperlipidemia, statin-resistant hypercholesterolemia, coronary artery disease (CAD), and coronary heart disease (CHD).

The invention provides for a method of treating hypercholesterolemia or a related disorder, such as a disorder selected from the group consisting atherosclerosis, hyperlipidemia, hypercholesterolemia, familiar hypercholesterolemia e.g. gain of function mutations in PCSK9, HDL/LDL cholesterol imbalance, dyslipidemias, e.g., familial hyperlipidemia (FCHL) or familial hypercholesterolemia (FHC), acquired hyperlipidemia, statin-resistant hypercholesterolemia, coronary artery disease (CAD), and coronary heart disease (CHD), said method comprising administering an effective amount of an oligomer or conjugate or pharmaceutical composition according to the invention, to a patient suffering from, or likely to suffer from hypercholesterolemia or a related disorder.

The invention provides for an in vivo or in vitro method for the inhibition of PCSK9 in a cell which is expressing PCSK9, said method comprising administering an oligomer or conjugate or pharmaceutical composition according to the invention to said cell so as to inhibit PCSK9 in said cell.

The invention also provides for an oligomer according to the invention, such as an LNA oligomer, comprising a contiguous region of 10-22, such as 12-18, such as 13, 14, 15, 16 or 17 phosphorothioate linked nucleosides, (i.e. region A, which typically is complementary to a corresponding region of the target sequence, such as SEQ ID NO 46) and further comprising between 1 and 6 DNA nucleosides which are contiguous with the LNA oligomer, wherein the inter-nucleoside linkages between the DNA, and/or adjacent to the DNA nucleoside(s), is physiologically labile, such as is/are phosphodiester linkages. Such an LNA oligomer may be in the form of a conjugate, as described herein, or may, for example be an intermediate to be used in a subsequent conjugation step. When conjugated, the conjugate may, for example be or comprise a sterol, such as cholesterol or tocopherol, or may be or comprise a (non-nucleotide) carbohydrate, such as a GalNAc conjugate, or another conjugate as described herein.

The invention also provides a gapmer oligomer which comprises at least one cET, such as (S)-cET nucleotides, of between 10-22, such as 12-18, such as 13, 14, 15, 16 or 17 nucleotides in length, which targets (i.e. has a sequence which is complementary to a corresponding part of) human PCSK9.

BRIEF DESCRIPTION OF FIGURES

FIG. 3: Specific LNA compounds. Beta-D-oxy LNA are identified by a superscript $^L$ after the letter, subscript $_s$ represents a phosphorothioate linkage, superscript $^{Me}$ preceding a capital C represents 5-methyl cytosine LNA, non LNA nucleotides are DNA nucleotides (no superscript L).

FIG. 4: Examples of cholesterol conjugates of the LNA compounds. Beta-D-oxy LNA are identified by a superscript $^L$ after the letter, subscript $_s$ represents a phosphorothioate linkage, $_o$ subscript represents a phosphodiester linkage, superscript $^{Me}$ preceding a capital C represents 5-methyl cytosine LNA, non LNA nucleotides are DNA nucleotides (no superscript L).

FIG. 14. Silencing of PCSK9 mRNA with cholesterol-conjugates in vivo. Mice were injected with a single dose of 10 mg/kg unconjugated LNA-antisense oligonucleotide (SEQ ID NO:40) or equimolar amounts of LNA antisense oligonucleotides conjugated to Cholesterol with different linkers and sacrificed at days 1, 3, 7 and 1 0 after dosing. RNA was isolated from liver and kidney and subjected to PCSK9 specific RT-qPCR A. Quantification of PCSK9 mRNA from liver samples normalized to BACT and shown as percentage of the average of equivalent saline controls B. Quantification of PCSK9 mRNA from kidney samples normalized to BACT and shown as percentage of the average of equivalent saline controls.

FIG. 17. Serum PCSK9 and LDL cholesterol in samples from cynomolgus monkeys injected four times (one injection/week) with 0.5 or 1.5 mg/kg/week of SEQ ID 3 and 19.

DETAILED DESCRIPTION OF INVENTION

Figure 12:
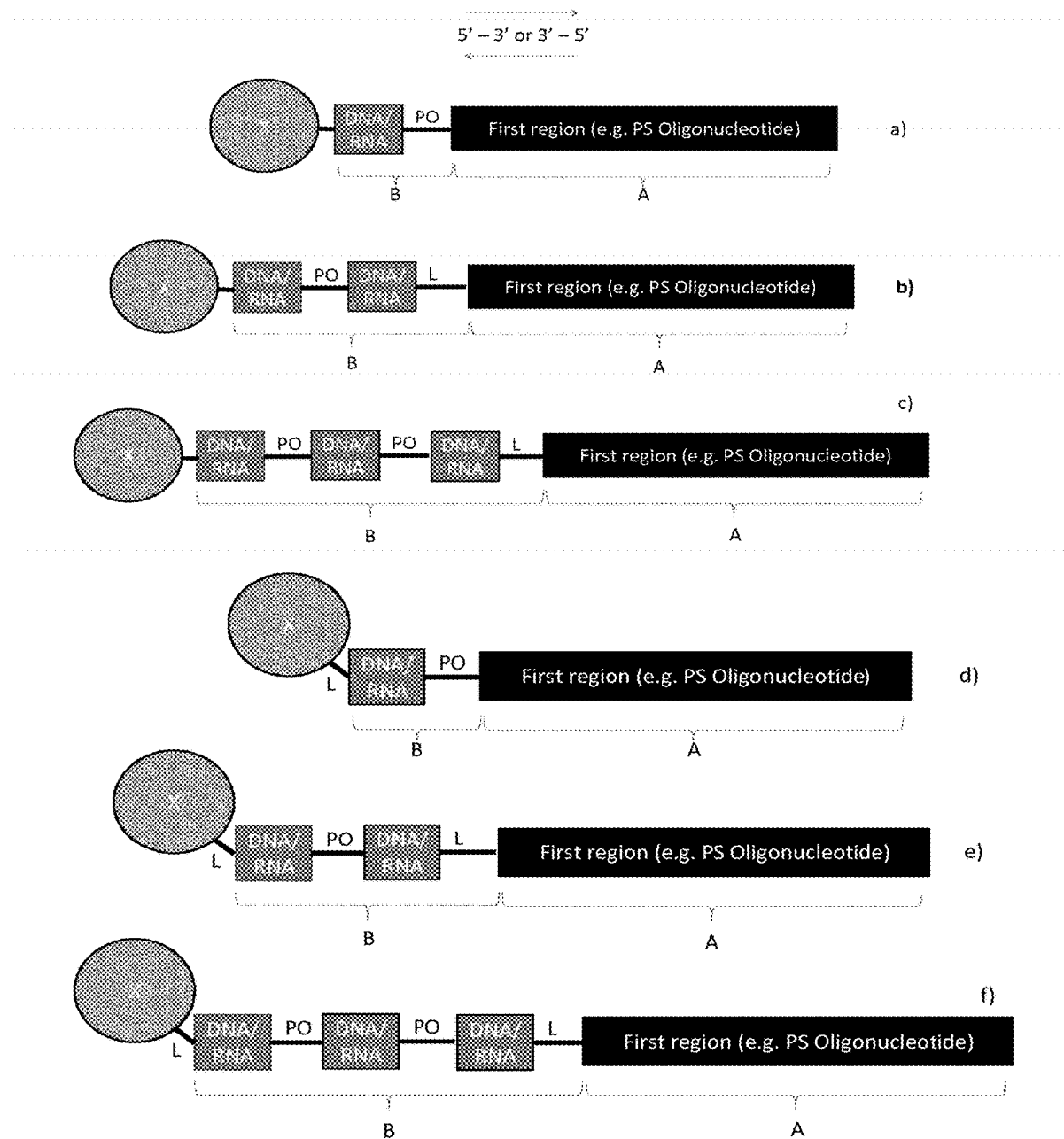
FIG. 12: Non-limiting Illustration of compounds of the invention. The inter-nucleoside linkage L may be, for example phosphodiester, phosphorothioate, phosphorodithioate, boranophosphate or methylphosphonate, such as phosphodiester. PO is a phosphodiester linkage. Compound a) has a region B with a single DNA (or RNA), the linkage between the second and the first region is PO. Compound b) has two DNA/RNA (such as DNA) nucleosides linked by a phosphodiester linkage. Compound c) has three DNA/RNA (such as DNA) nucleosides linked by a phosphodiester linkages. In some embodiments, Region B may be further extended by further phosphodiester DNA/RNA (such as DNA nucleosides). The conjugate group (Marked X, otherwise region C herein) is illustrated on the left side of each compound (e.g. Cholesterol, GalNAc, Conj1-4, 1a-4a, and 5 or 6), and may, optionally be covalently attached to the terminal nucleoside of region B via a phosphorus nucleoside linkage group, such as phosphodiester, phosphorothioate, phosphorodithioate, boranophosphate or methylphosphonate, or may be linked via an alternative linkage, e.g. a triazol linkage (see L in compounds d), e), and f FIG. 13. Non-limiting Illustration of compounds of the invention, where the compounds comprise the optional linker (Y) between the third (conjugate) region (X) and the second region (region B). Same nomenclature as FIG. 12. Suitable linkers are disclosed herein, and include, for example alkyl linkers, for example C6 linkers. In compounds a), b) and c), the linker between X and region B is attached to region B via a phosphorus nucleoside linkage group, such as phosphodiester, phosphorothioate, phosphorodithioate, boranophosphate or methylphosphonate, or may be linked via an alternative linkage eg. a triazol linkage (Li). In these compounds Lii represents the internucleoside linkage between the first (A) and second regions (B). Compounds d), e), & f) further comprise a linker (Y) between region B and the conjugate group, and region Y may be linked to region B via, for example, a phosphorus nucleoside linkage group, such as phosphodiester, phosphorothioate, phosphorodithioate, boranophosphate or methylphosphonate, or in some embodiments a triazole linkage. In addition, or alternatively X may be an activation group or a reactive group. X may be covalently attached to region B via a phosphorus nucleoside linkage group, such as phosphodiester, phosphorothioate, phosphorodithioate, boranophosphate or methylphosphonate, or may be linked via an alternative linkage, e.g. a triazol linkage.
Figure 13:
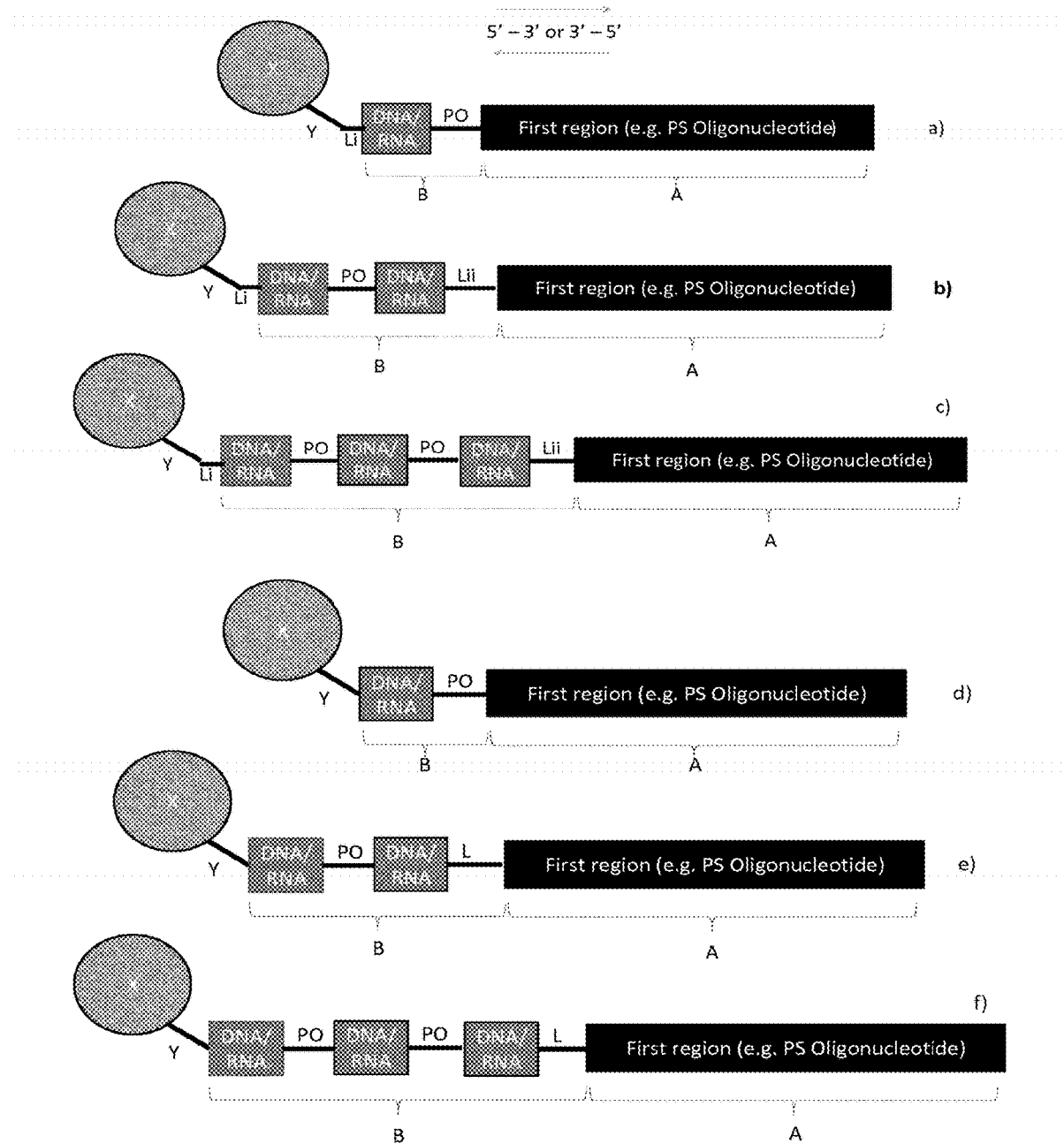

In the following different elements of the invention are described under separate headings. It is understood that an embodiment from one element can be combined with embodiments from the other elements to arrive at a compound of the invention (e.g. as illustrated in FIGS. 12 and 13)

The Oligomer (Region A)

The term "oligomer" or "oligonucleotide" in the context of the present invention, refers to a molecule formed by covalent linkage of two or more nucleotides (i.e. an oligonucleotide). Herein, a single nucleotide (unit) may also be referred to as a monomer or unit. In some embodiments, the terms "nucleoside", "nucleotide", "unit" and "monomer" are used interchangeably. It will be recognized that when referring to a sequence of nucleotides or monomers, what is referred to is the sequence of bases, such as A, T, G, C or U.

The oligomer of the invention may comprise between 10-22, such as 12-22 nucleotides, such as 12-18 nucleotides in length. The oligomer comprises either a) a contiguous sequence of 10-16 nucleotides which are complementary to a corresponding length of SEQ ID NO 33 or 34 or 45, or b) a contiguous sequence of 16 nucleotides which are complementary to a corresponding length of SEQ ID NO 31.

In some embodiments, the oligomer of the invention comprises a contiguous sequence selected from the group consisting of SEQ ID NO 26, 27, 28, 29 and 44.

The compound (e.g. oligomer or conjugate) of the invention targets PCSK9, and as such is capable of down regulating the expression of or inhibiting PCSK9, such as PCSK9 in a human or in a cell expressing PCSK9.

In some embodiments, the internucleoside linkages of the a contiguous sequence of 10-16 nucleotides which are complementary to a corresponding length of SEQ ID NO 33 or 34 or 45 may be phosphorothioate linkages.

In some embodiments, the oligomer of the invention comprises or consists a contiguous sequence selected from the group consisting of SEQ ID NO 2, 3, 4, 5, 6, 7, 8 and 40. In one embodiment, the oligomer comprises or consists of a sequence selected from a) SEQ ID NO 2 or 3, or b) SEQ ID NO 4, 5 or 6, or c) SEQ ID NO 7 or 8, or d) SEQ ID NO 40.

In some embodiments, the oligomer comprises 10-16 phosporothiolate linked nucleosides.

In some embodiments, the oligomer of the invention comprises a contiguous sequence of at least 10-16 nucleotides which are complementary to a corresponding length of SEQ ID NO 33 or 34 or 45 or a contiguous sequence of 16 nucleotides which are complementary to a corresponding length of SEQ ID NO 31, wherein the contiguous sequence comprises nucleotide analogues. Preferably, the nucleotide analogues are affinity enhancing nucleotide analogues.

In some embodiments, the nucleotide analogues are sugar modified nucleotides, such as sugar modified nucleotides independently or dependently selected from the group consisting of: Locked Nucleic Acid (LNA) units; 2'-O-alkyl-RNA units, 2'-OMe-RNA units, 2'-amino-DNA units, and 2'-fluoro-DNA units.

In some embodiments, the nucleotide analogues comprise or are Locked Nucleic Acid (LNA) units.

In some embodiments, the oligomer of the invention comprises or is a gapmer, such as a LNA gapmer oligonucleotide.

In some embodiments, the Gapmer comprise a wing on each side (5' and 3') of 2 to 4 nucleotide analogues, preferably LNA analogues.

In some embodiments, the oligomer of the invention comprises a contiguous sequence of 13, 14, 15 or 16 nucleotides which are complementary to a corresponding length of SEQ ID NO 33 or 34 or 45 or a contiguous sequence of 16 nucleotides which are complementary to a corresponding length of SEQ ID NO 31, and may optionally comprise a further 1-6 nucleotides, which may form or comprise a biocleavable nucleotide region, such as a phosphate nucleotide linker. Suitably, the biocleavable nucleotide region is formed of a short stretch (eg. 1, 2, 3, 4, 5 or 6) of nucleotides which are physiologically labile. This may be achieved by using phosphodiester linkages with DNA/RNA nucleosides, or if physiological liability can be maintained, other nucleoside may be used. Physiological liability may be measured using a liver extract, as illustrated in example 6.

The oligomer of the invention may therefore comprise of a contiguous nucleotide sequence of 10-16 nts in length which is complementary to a corresponding length of SEQ ID NO 33 or 34 or 45 or a contiguous sequence of 16 nucleotides which are complementary to a corresponding length of SEQ ID NO 31 (A first region, or region A). The oligomer of the invention may comprise a further nucleotide region. In some embodiments, the further nucleotide region comprises a biocleavable nucleotide region, such as a phosphate nucleotide sequence (a second region, region B), which may covalently link region A to a non-nucleotide moiety, such as a conjugate group, (a third region, or region C). In some embodiments the contiguous nucleotide sequence of the oligomer of the invention (region A) is directly covalently linked to region C. In some embodiments region C is biocleavable.

The oligomer consists or comprises of a contiguous nucleotide sequence of from 12-22, such as 13, 14, 15, 16, 17, 18, 19, 20, 21, nucleotides in length, such as 14-16 nucleotides in length, such as 15 or 16 nucleotides in length. The oligomer may therefore refer to the combined length of region A and region B, e.g. (Region A 10-16 nt) and region B (1-6 nt).

In various embodiments, the compound of the invention does not comprise RNA (units). In some embodiments, the compound according to the invention, the first region, or the first and second regions together (e.g. as a single contiguous sequence), is a linear molecule or is synthesised as a linear molecule. The oligomer may therefore be single stranded molecule. In some embodiments, the oligomer does not comprise short regions of, for example, at least 3, 4 or 5 contiguous nucleotides, which are complementary to equivalent regions within the same oligomer (i.e. duplexes). The oligomer, in some embodiments, may be not (essentially) double stranded. In some embodiments, the oligomer is essentially not double stranded, such as is not a siRNA.

Oligomer Sequences

The following table provides oligomers and oligomer conjugates of the invention and PCSK9 target sequences of the invention

TABLE 1

| SEQ ID | Sequence | PO | Chol-C6 | GalNAc | Position on the PCSK9 gene SEQ ID NO 44 |
|---|---|---|---|---|---|
| 1 | TGCtacaaaacCCA | | | | 3643-3656 |
| 2 | AATgctacaaaaCCCA | | | | 3643-3658 |
| 3 | AATgctacaaaacCCA | | | | 3643-3658 |
| 4 | GCtgtgtgagcttGG | | | | 3251-3265 |
| 5 | TGctgtgtgagctTGG | | | | 3251-3266 |
| 6 | TGCtgtgtgagctTGG | | | | 3251-3266 |
| 7 | TCCtggtctgtgtTCC | | | | 3373-3388 |
| 8 | TCCtggtctgtgttCC | | | | 3373-3388 |
| 9 | TGCtacaaaacCCA | yes | yes | | 3643-3656 |
| 10 | AATgctacaaaaCCCA | yes | yes | | 3643-3658 |
| 11 | AATgctacaaaacCCA | yes | yes | | 3643-3658 |
| 12 | GCtgtgtgagcttGG | yes | yes | | 3251-3265 |

TABLE 1-continued

| SEQ ID | Sequence | PO | Chol-C6 | GalNAc | Position on the PCSK9 gene SEQ ID NO 44 |
|---|---|---|---|---|---|
| 13 | TGctgtgtgagctTGG | yes | yes | | 3251-3266 |
| 14 | TGCtgtgtgagctTGG | yes | yes | | 3251-3266 |
| 15 | TCCtggtctgtgtTCC | yes | yes | | 3373-3388 |
| 16 | TCCtggtctgtgttCC | yes | yes | | 3373-3388 |
| 17 | TGCtacaaaacCCA | | | yes | 3643-3656 |
| 18 | AATgctacaaaaCCCA | | | yes | 3643-3658 |
| 19 | AATgctacaaaacCCA | | | yes | 3643-3658 |
| 20 | GCtgtgtgagcttGG | | | yes | 3251-3265 |
| 21 | TGctgtgtgagctTGG | | | yes | 3251-3266 |
| 22 | TGCtgtgtgagctTGG | | | yes | 3251-3266 |
| 23 | TCCtggtctgtgtTCC | | | yes | 3373-3388 |
| 24 | TCCtggtctgtgttCC | | | yes | 3373-3388 |
| 40 | GTctgtggaaGCG | | | | 1005-1017 |
| 41 | GTctgtggaaGCG | | yes | | 1005-1017 |
| 42 | GTctgtggaaGCG | yes | yes | | 1005-1017 |
| 43 | GTctgtggaaGCG | yes | yes | | 1005-1017 |
| 25 | tgctacaaaaccca | | | | 3643-3656 |
| 26 | aatgctacaaaaccca | | | | 3643-3658 |
| 27 | gctgtgtgagcttgg | | | | 3251-3265 |
| 28 | tgctgtgtgagcttgg | | | | 3251-3266 |
| 29 | tcctggtctgtgttcc | | | | 3373-3388 |
| 44 | gtctgtggaagcg | | | | 1005-1017 |
| 30 | UGGGUUUUGUAGCA | | | | 3643-3656 |
| 31 | UGGGUUUUGUAGCAUU | | | | 3643-3658 |
| 32 | CCAAGCUCACACAGC | | | | 3251-3265 |
| 33 | CCAAGCUCACACAGCA | | | | 3251-3266 |
| 34 | GGAACACAGACCAGGA | | | | 3373-3388 |
| 45 | CGCUUCCACAGAC | | | | 1005-1017 |

SEQ ID NO 25-29 and 44 are nucleobase sequence motifs.

SEQ ID NOs 30-34 and 45 are the RNA target sequences present in the human PCSK9 mRNA.

SEQ ID NO 1 is SPC5001.

SEQ ID NOs 1-24 and 40 to 43 are oligomers comprising nucleotide analogues such as LNA gapmer oligomers, where lower case letters are DNA units (nucleoside/nucleotide) where capital letters are LNA units, In some embodiments all LNA C are 5-methyl cytosine. In some embodiments all LNA units are beta-D-oxy LNA. In some embodiments the internucleoside linkages between the nucleosides of SEQ ID NOs 1-24 and 40 to 43 are all phosphorothioate linkages.

SEQ ID NOs 9-16 and 41 to 43 comprise the oligomer (as indicated by the SEQ ID) as well as a cholesterol conjugate which may be covalently linked to the oligomer 5' or 3' end of the oligomer, optionally via a biocleavable linker, such as a phosphate nucleoside linker. In some embodiments, the cholesterol conjugate is linked at the 5' end of the oligomer.

SEQ ID NOs 17-24 comprise the oligomer (as indicated by the SEQ ID) as well as a GalNAc conjugate which may be covalently linked to the oligomer 5' or 3' end of the oligomer, optionally via a biocleavable linker, such as a phosphate nucleoside linker or cleavable peptide linker. In some embodiments, the GalNAc conjugate is linked at the 5' end of the oligomer.

Figure 1:
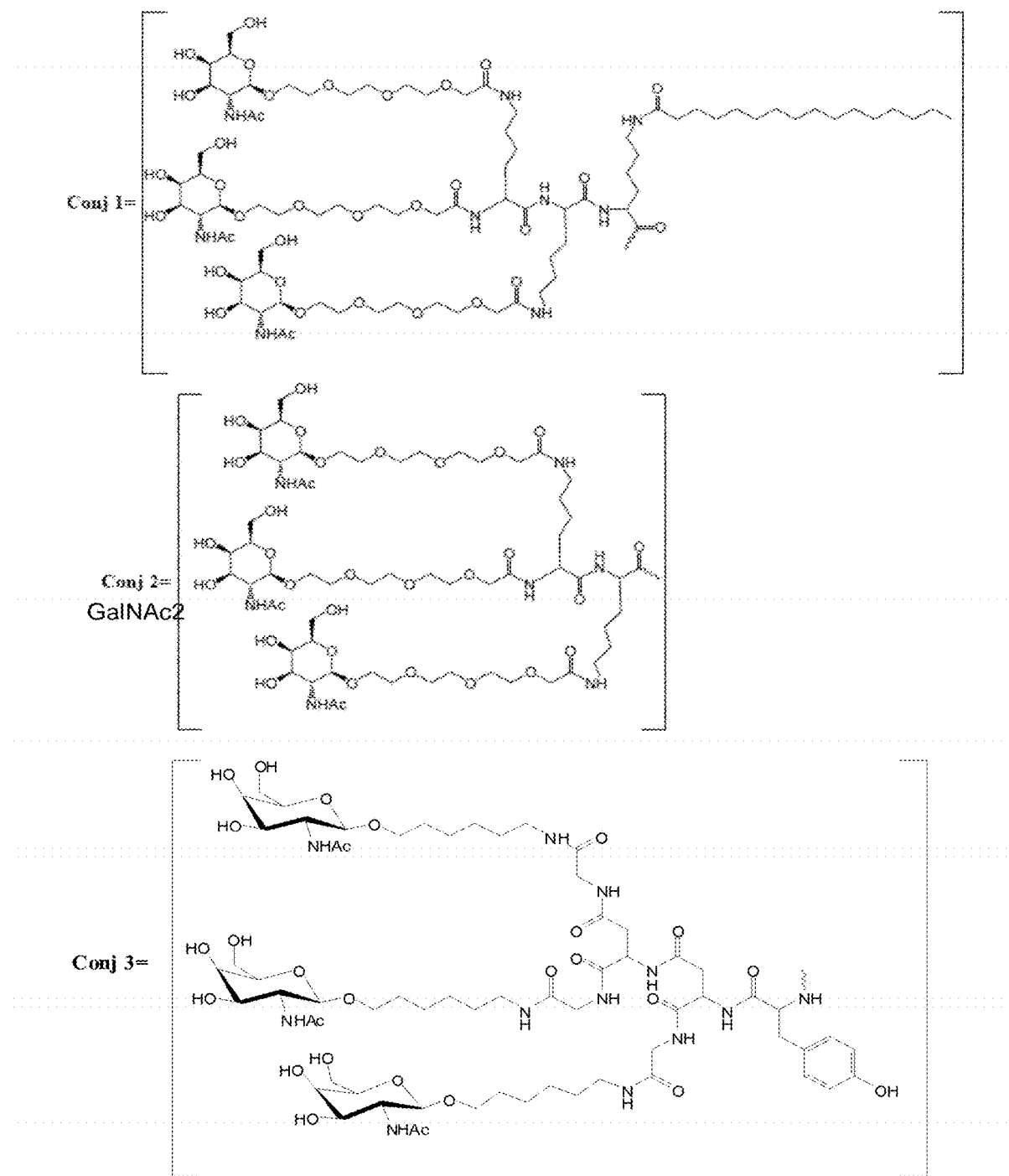
FIG. 1: Examples of tri-GalNAc conjugates which may be used. Conjugates 1-4 illustrate 4 suitable GalNAc conjugate moieties, and conjugates 1a-4a refer to the same conjugates with an additional linker moiety (Y) which is used to link the conjugate to the oligomer (region A or to a bio-cleavable linker, such as region B). The wavy line represents the covalent link to the oligomer.
Figure 1:
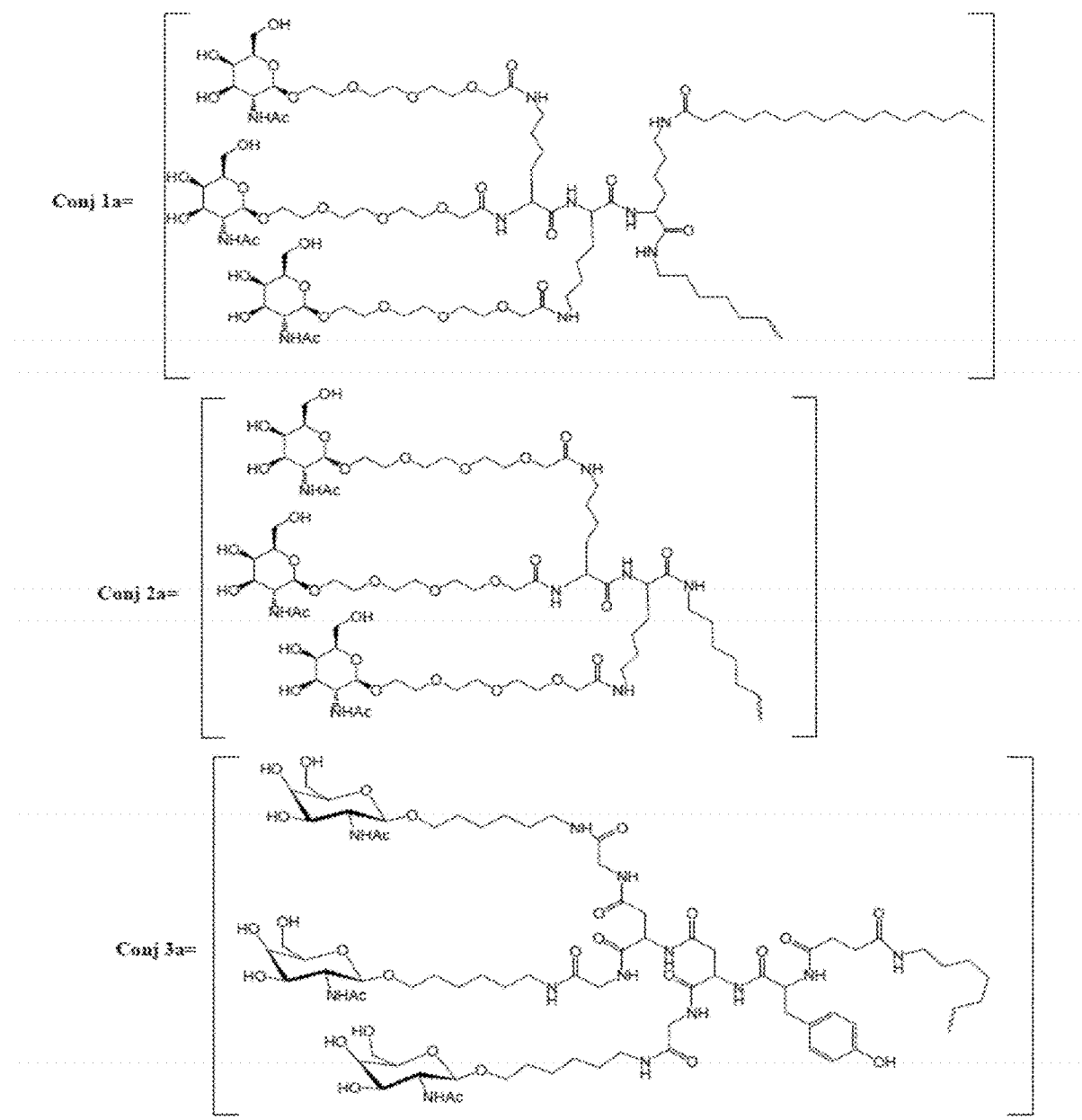
Figure 2:
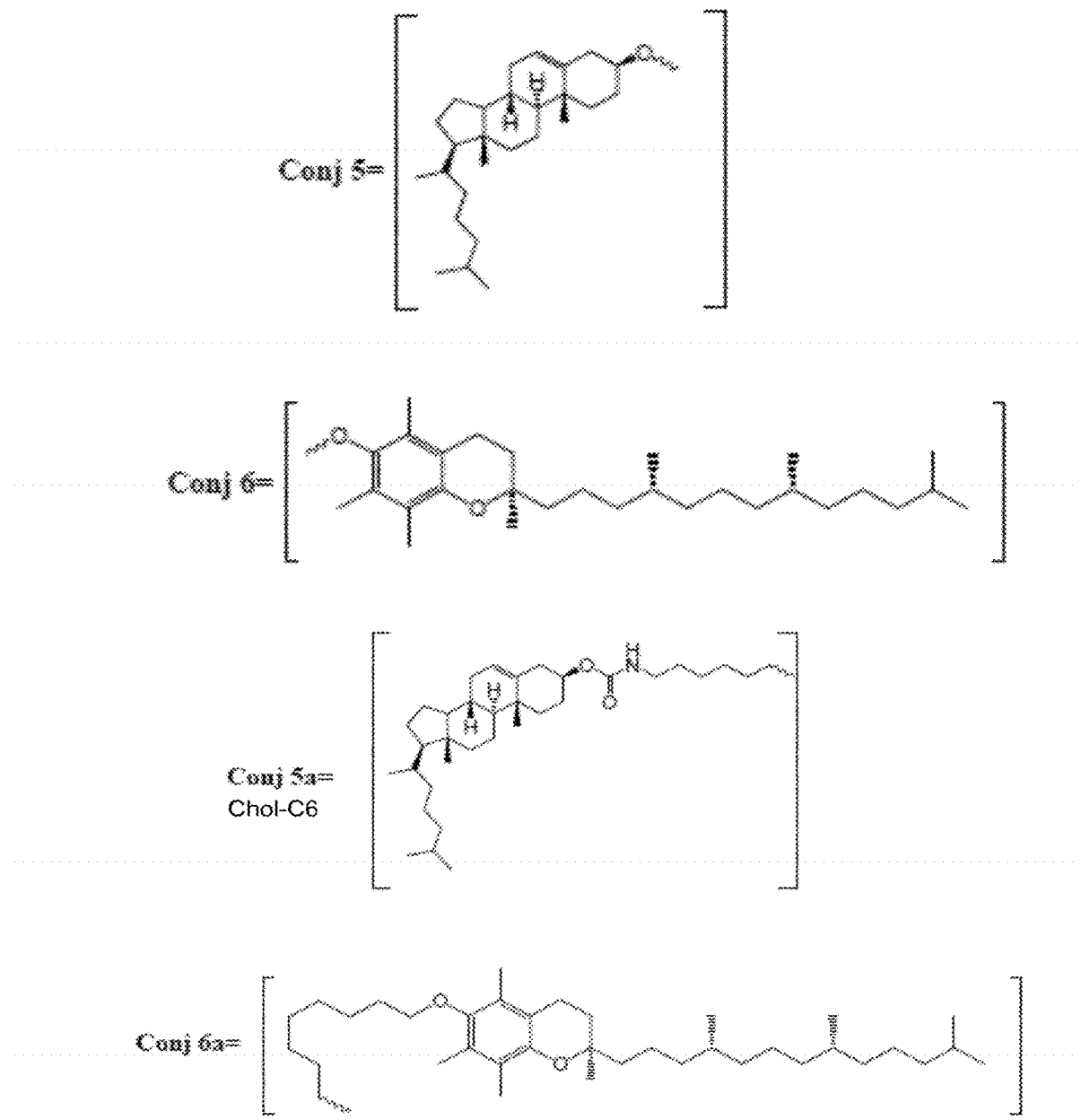
FIG. 2: Examples of cholesterol and tocopherol conjugate moieties. Conjugates 5a and 6a refer to the same conjugates with an additional linker moiety (Y) which is used to link the conjugate to the oligomer (region A or to a bio-cleavable linker, such as region B). The wavy line represents the covalent link to the oligomer.
Figure 5:
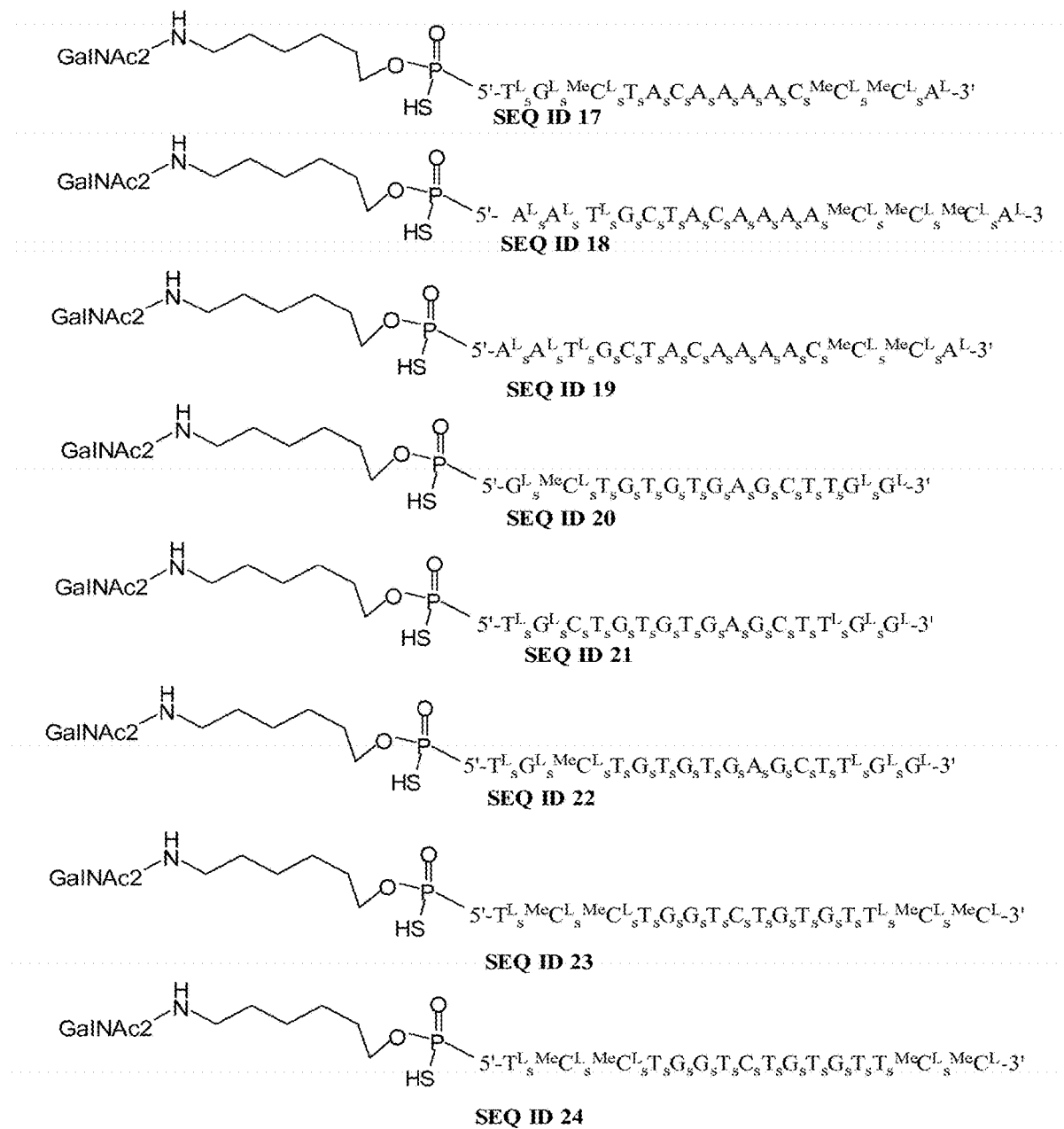
FIG. 5: Examples of GalNAc conjugates of the LNA compounds. The conjugates essentially correspond to Conj2a in Figure where the wavy line is substituted with the LNA oligomer. Beta-D-oxy LNA are identified by a superscript $^L$ after the letter, subscript $_s$ represents a phosphorothioate linkage, superscript $^{Me}$ preceding a capital C represents 5-methyl cytosine LNA, non LNA nucleotides are DNA nucleotides (no superscript L).

Specific oligomers and conjugates used herein are illustrated in FIG. 3 (oligomers), FIG. 4 (cholesterol conjugates), FIG. 5 (GalNAc conjugates). Other examples of conjugates which may be used with the oligomer of the invention are illustrated in FIGS. 1 and 2 and described in section GalNAc Conjugate Moieties.

Table 2 provides specific combinations of oligomer and conjugates.

TABLE 2

Oligomer/conjugate combinations.

| SEQ ID | Conjugate Number (See FIG.1) | | | | | | | |
|---|---|---|---|---|---|---|---|---|
| | Conj1 | Conj2 | Conj3 | Conj4 | Conj1a | Conj2a | Conj3a | Conj4a |
| 2 | C1 | C2 | C3 | C4 | C5 | C6 | C7 | C8 |
| 3 | C11 | C12 | C13 | C14 | C15 | C16 | C17 | C18 |
| 4 | C12 | C13 | C14 | C15 | C16 | C17 | C18 | C19 |
| 5 | C30 | C31 | C32 | C33 | C34 | C35 | C36 | C37 |
| 6 | C40 | C41 | C42 | C43 | C44 | C45 | C46 | C47 |
| 7 | C50 | C51 | C52 | C53 | C54 | C55 | C56 | C57 |
| 8 | C60 | C61 | C62 | C63 | C64 | C65 | C66 | C67 |

| SEQ ID | Conjugate Number (See FIG. 2) | | | |
|---|---|---|---|---|
| | Conj5 | Conj6 | Conj5a | Conj6a |
| 2 | C9 | C10 | C70 | C71 |
| 3 | C19 | C20 | C72 | C73 |
| 4 | C20 | C21 | C74 | C75 |
| 5 | C38 | C39 | C76 | C77 |
| 6 | C48 | C49 | C78 | C79 |
| 7 | C58 | C59 | C80 | C81 |
| 8 | C68 | C69 | C82 | C83 |

Figure 5A:
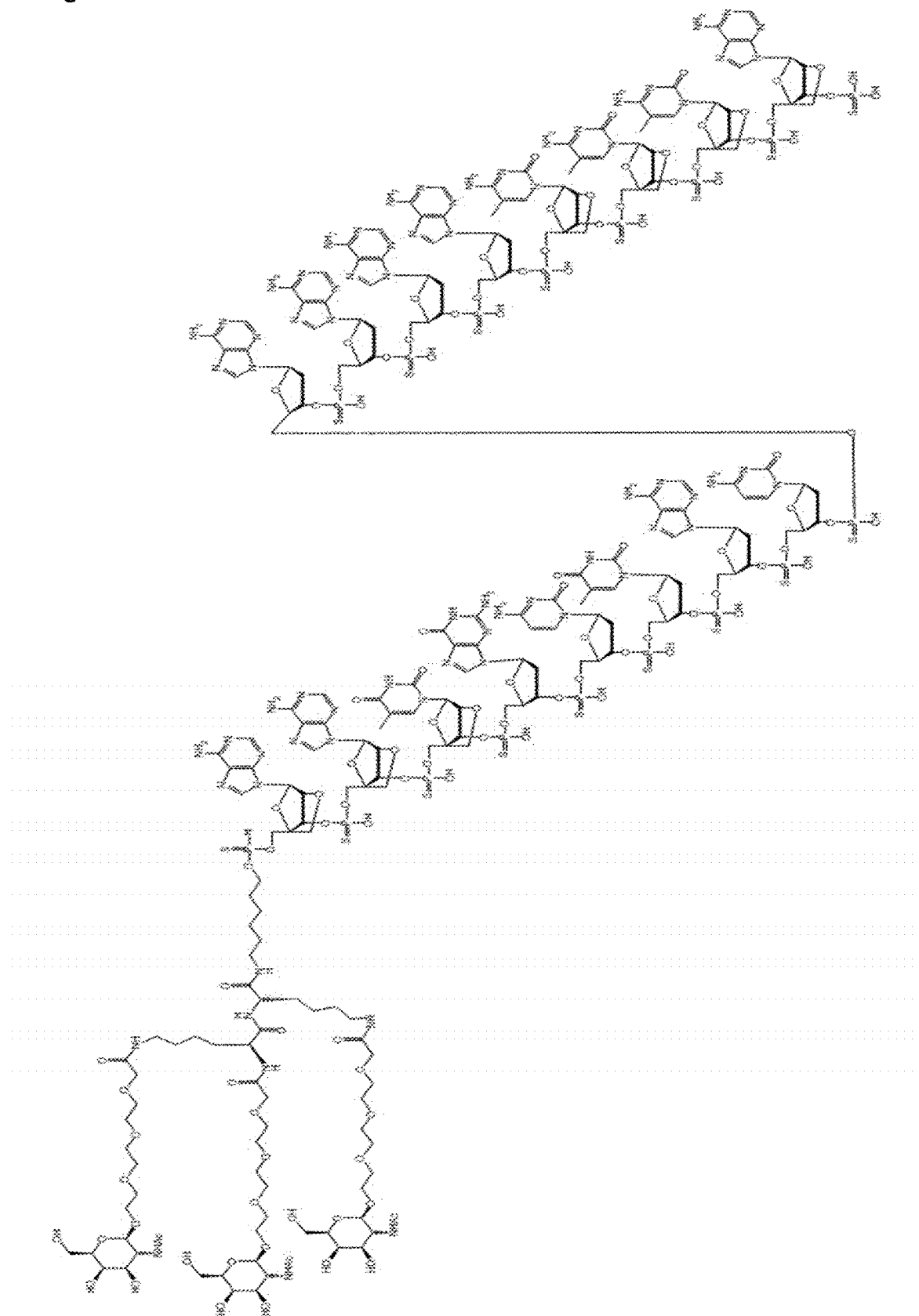
FIG. 5A: Detailed structure of SEQ ID NO 18
Figure 5B:
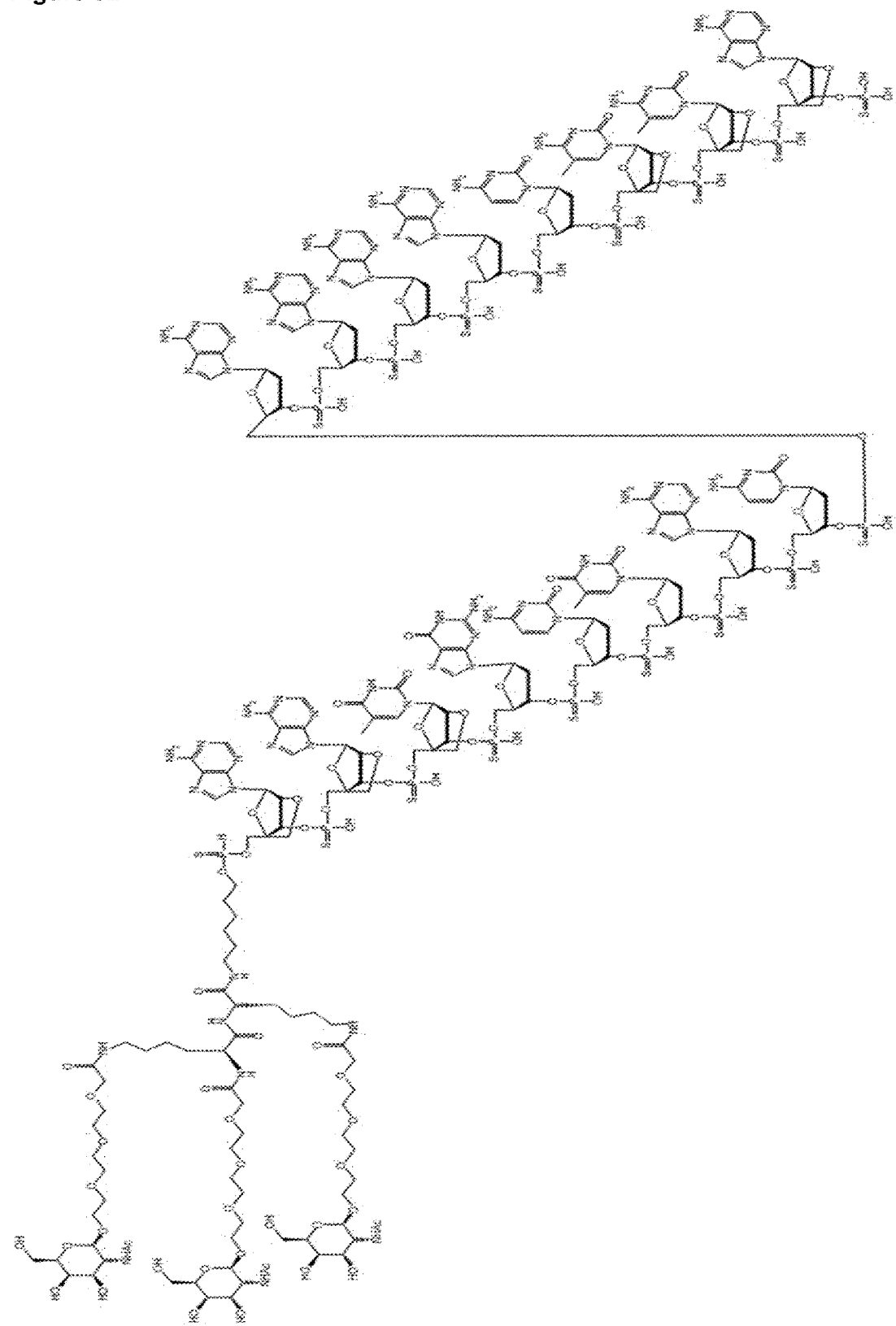
FIG. 5B: Detailed structure of SEQ ID NO 19

All these combinations can be visualized by substituting the wavy line in FIG. 1 or 2 with the sequence of the oligomer. FIG. 5 show the combination of Conj2a with the indicated SEQ ID NO's above. FIGS. 5A and 5B are two detailed examples of the compounds in FIG. 5. Please note that a biocleavable linker (B) may or may not be present between the conjugate moiety (C) and the oligomer(A). For Conj1-4 and 1a-4a the GalNAc conjugate itself is biocleavable, utilizing a peptide linker in the GalNAc cluster, and as such a further biocleavable linker (B) may or may not be used. However, preliminary data indicates inclusion of a biocleavable linker (B), such as the phosphate nucleotide linkers disclosed herein may enhance activity of such GalNAc cluster oligomer conjugates. FIG. 4 shows the combination of Conj5a with the indicated SEQ ID NO's above with a biocleavable linker (B) composed of two DNA monomers C and A linked with a phosphodiester linkage. For use with Conj 5 and Conj 6, the use of a biocleavable linker greatly enhances compound activity inclusion of a biocleavable linker (B), such as the phosphate nucleotide linkers disclosed herein is recommended.

The terms "corresponding to" and "corresponds to" refer to the comparison between the nucleotide sequence of the oligomer (i.e. the nucleobase or base sequence) or contiguous nucleotide sequence (a first region/region A) and the reverse complement of the nucleic acid target, or sub-region thereof (e.g. SEQ ID NO 31, 32 33, 34 or 45). Nucleotide analogues are compared directly to their equivalent or corresponding nucleotides. In a preferred embodiment, the oligomers (or first region thereof) are complementary to the target region or sub-region thereof (e.g. SEQ ID NO 31, 32, 33, 34 or 45), such as fully complementary.

The terms "reverse complement", "reverse complementary" and "reverse complementarity" as used herein are interchangeable with the terms "complement", "complementary" and "complementarity".

The term, "complementary" means that two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence. Normally, the complementary sequence of the oligonucleotide has at least 90%, preferably 95%, most preferably 100%, complementarity to a defined sequence.

The terms "corresponding nucleotide analogue" and "corresponding nucleotide" are intended to indicate that the nucleotide in the nucleotide analogue and the naturally occurring nucleotide are identical. For example, when the 2-deoxyribose unit of the nucleotide is linked to an adenine, the "corresponding nucleotide analogue" contains a pentose unit (different from 2-deoxyribose) linked to an adenine.

The term "nucleobase" refers to the base moiety of a nucleotide and covers both naturally occurring a well as non-naturally occurring variants. Thus, "nucleobase" covers not only the known purine and pyrimidine heterocycles but also heterocyclic analogues and tautomeres thereof. It will be recognised that the DNA or RNA nucleosides of region B may have a naturally occurring and/or non-naturally occurring nucleobase(s).

Examples of nucleobases include, but are not limited to adenine, guanine, cytosine, thymidine, uracil, xanthine, hypoxanthine, 5-methylcytosine, isocytosine, pseudoisocytosine, 5-bromouracil, 5-propynyluracil, 6-aminopurine, 2-aminopurine, inosine, diaminopurine, and 2-chloro-6-aminopurine. In some embodiments the nucleobases may be independently selected from the group consisting of adenine, guanine, cytosine, thymidine, uracil, 5-methylcytosine. In some embodiments the nucleobases may be independently selected from the group consisting of adenine, guanine, cytosine, thymidine, and 5-methylcytosine.

In some embodiments, at least one of the nucleobases present in the oligomer is a modified nucleobase selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

The Target

Suitably the oligomer of the invention is capable of modulating the expression of the PCSK9 gene. Preferably the oligomer is capable of down-regulating expression of the PCSK9 gene. In this regards, the oligomer of the invention can affect the expression of PCSK9, typically in a mammalian such as a human cell, such as a liver cell. In some embodiments, the oligomers of the invention bind to the target nucleic acid and the effect on expression is at least 10% or 20% reduction compared to the normal expression level (e.g. the expression level of a cell, animal or human treated with saline), more preferably at least a 30%, 40%, 50%, 60%, 70%, 80%, 90% or 95% inhibition compared to the normal expression level. In some embodiments, such modulation is seen when using between 0.04 and 25 nM, such as between 0.8 and 20 nM concentration of the compound of the invention. In some embodiments, such modulation is seen when using between 0.01 and 15 mg/kg, such as between 0.05 and 10 mg/kg, such as between 0.1 and 7.5 mg/kg, such as between 0.25 and 5 mg/kg, such as 0.5 and 2.5 mg/kg concentration of the compound of the invention. In the same or a different embodiment, the inhibition of expression is less than 100%, such as less than 98% inhibition, less than 95% inhibition, less than 90% inhibition, less than 80% inhibition, such as less than 70% inhibition. Modulation of expression level may be determined by measuring protein levels, e.g. by the methods such as SDS-PAGE followed by western blotting using suitable antibodies raised against the target protein. Alternatively, modulation of expression levels can be determined by measuring levels of mRNA, e.g. by northern blotting or quantitative RT-PCR. When measuring via mRNA levels, the level of down-regulation when using an appropriate dosage, such as between 0.04 and 25 nM, such as between 0.8 and 20 nM concentration, is, in some embodiments, typically to a level of between 10-20% the normal levels in the absence of the compound of the invention.

The invention therefore provides a method of down-regulating or inhibiting the expression of PCSK9 protein and/or mRNA in a cell which is expressing PCSK9 protein and/or mRNA, said method comprising administering the oligomer or conjugate according to the invention to said cell to down-regulating or inhibiting the expression of PCSK9 protein and/or mRNA in said cell. Suitably the cell is a mammalian cell such as a human cell. The administration may occur, in some embodiments, in vitro. The administration may occur, in some embodiments, in vivo.

The term "target nucleic acid", as used herein refers to the DNA or RNA encoding mammalian PCSK9 polypeptide, such as human PCSK9, such as NCBI accession number NM_174936 SEQ ID NO: 46. PCSK9 encoding nucleic acids or naturally occurring variants thereof, and RNA nucleic acids derived therefrom, preferably mRNA, such as pre-mRNA, although preferably mature mRNA. In some embodiments, for example when used in research or diagnostics the "target nucleic acid" may be a cDNA or a synthetic oligonucleotide derived from the above DNA or RNA nucleic acid targets. The oligomer according to the invention is preferably capable of hybridising to the target nucleic acid. It will be recognised that SEQ ID NO: 46 is a cDNA sequence, and as such, corresponds to the mature mRNA target sequence, although uracil is replaced with thymidine in the cDNA sequences.

The term "naturally occurring variant thereof" refers to variants of the PCSK9 polypeptide of nucleic acid sequence which exist naturally within the defined taxonomic group, such as mammalian, such as mouse, monkey, and preferably human. Typically, when referring to "naturally occurring variants" of a polynucleotide the term also may encompass any allelic variant of the PCSK9 encoding genomic DNA which are found at the chromosome 4, at 4 C7 by chromosomal translocation or duplication, and the RNA, such as mRNA derived therefrom. "Naturally occurring variants" may also include variants derived from alternative splicing of the PCSK9 mRNA. When referenced to a specific polypeptide sequence, e.g., the term also includes naturally occurring forms of the protein which may therefore be processed, e.g. by co- or post-translational modifications, such as signal peptide cleavage, proteolytic cleavage, glycosylation, etc.

In some embodiments the oligomer (or contiguous nucleotide portion thereof) is selected from, or comprises, one of the sequences selected from the group consisting of SEQ ID NOS: 28 or 29 or 44, or a sub-sequence of at least 10 contiguous nucleotides thereof, wherein said oligomer (or contiguous nucleotide portion thereof) may optionally comprise one, two, or three mismatches when compared to the sequence.

In some embodiments the target sequence is selected from, or comprises or consists of, one of the sequences selected from the group consisting of SEQ ID NOs 31, 32, 33, 34 or 45, or a sub-sequence of at least 10 contiguous nucleotides of SEQ ID NOs: 33, 34 or 45.

In some embodiments the sub-sequence may consist of 11, 12, 13, 14, 15 or 16 contiguous nucleotides, such as between 12-16 nucleotides. Suitably, in some embodiments, the sub-sequence is of the same length as the contiguous nucleotide sequence of the oligomer of the invention (optionally excluding region B when region B is not complementary to the target).

However, it is recognised that, in some embodiments the nucleotide sequence of the oligomer may comprise additional 5' or 3' nucleotides, such as, independently, 1, 2, 3, 4, 5 or 6 additional nucleotides 5' and/or 3', which are non-complementary to the target sequence—such non-complementary oligonucleotides may form region B In this respect the oligomer of the invention, may, in some embodiments, comprise a contiguous nucleotide sequence which is flanked 5' and or 3' by additional nucleotides. In some embodiments the additional 5' or 3' nucleotides are naturally occurring nucleotides, such as DNA or RNA. In some embodiments, the additional 5' or 3' nucleotides may represent region D as referred to in the context of gapmer oligomers herein.

In some embodiments, the oligomer according to the invention consists or comprises of a nucleotide sequence according to SEQ ID NO: 27, or a sub-sequence of at least 10 or 12 nucleobases thereof.

In some embodiments, the oligomer according to the invention consists or comprises of a nucleotide sequence according to SEQ ID NO: 28, or a sub-sequence of at least 10 or 12 nucleobases thereof. In a preferred embodiment, the oligomer according to the invention consists or comprises of a nucleotide sequence according to SEQ ID NO: 5 or 6. In another preferred embodiment the oligomer conjugate according to the invention consists or comprises of a nucleotide sequence according to SEQ ID NO: 13 or 14 or 21 or 22.

In some embodiments, the oligomer according to the invention consists or comprises of a nucleotide sequence according to SEQ ID NO: 29, or a sub-sequence of at least 10 or 12 nucleobases thereof. In a preferred embodiment, the oligomer according to the invention consists or comprises of a nucleotide sequence according to SEQ ID NO: 7 or 8. In another preferred embodiment the oligomer conjugate according to the invention consists or comprises of a nucleotide sequence according to SEQ ID NO: 15 or 16 or 23 or 24.

In some embodiments, the oligomer according to the invention consists or comprises of a nucleotide sequence according to SEQ ID NO: 44, or a sub-sequence of at least 10 or 12 nucleobases thereof. In a preferred embodiment, the oligomer according to the invention consists or comprises of a nucleotide sequence according to SEQ ID NO: 40. In another preferred embodiment the oligomer conjugate according to the invention consists or comprises of a nucleotide sequence according to SEQ ID NO: 41, 42 or 43.

In some embodiments the oligomer according to the invention consists or comprises of a nucleotide sequence according to SEQ ID NO:26. In a preferred embodiment, the oligomer according to the invention consists or comprises of a nucleotide sequence according to SEQ ID NO: 2 or 3. In another preferred embodiment, the oligomer conjugate according to the invention consists or comprises of a nucleotide sequence according to SEQ ID NO: 10 or 11 or 18 or 19.

Length

The oligomers may comprise or consist of a contiguous nucleotide sequence of a total of 10, 11, 12, 13, 14, 15, 16, 17, 18, 19, 20, 21, or 22 contiguous nucleotides in length. Lengths may include region A or region A and B for example.

In some embodiments, the oligomers comprise or consist of a contiguous nucleotide sequence of a total of between 10-22, such as 12-18, such as 13-17 or 12-16, such as 13, 14, 15, 16 contiguous nucleotides in length. Preferably the oligomer of region A comprise or consist of a contiguous nucleotide sequence of 14 contiguous nucleotides in length, more preferred of 15 contiguous nucleotides in length, and most preferred of 16 contiguous nucleotides in length.

In some embodiments, the oligomer according to the invention consists of no more than 22 nucleotides, such as no more than 20 nucleotides, such as no more than 18 nucleotides, such as 15, 16 or 17 nucleotides. In some embodiments, the oligomer of the invention comprises less than 20 nucleotides.

Nucleotide Analogues

The term "nucleotide" as used herein, refers to a glycoside comprising a sugar moiety, a base moiety and a covalently linked group, such as a phosphate or phosphorothioate internucleotide linkage group, and covers both naturally occurring nucleotides, such as DNA or RNA, and non-naturally occurring nucleotides comprising modified sugar and/or base moieties, which are also referred to as "nucleotide analogues" herein. Herein, a single nucleotide (unit) may also be referred to as a monomer or nucleic acid unit.

In field of biochemistry, the term "nucleoside" is commonly used to refer to a glycoside comprising a sugar moiety and a base moiety. The covalent linkage between two nucleosides may be referred to as an internucleoside linkage. Alternatively, the term internucleotide linkage may be used to characterize the linkage between the nucleotides of the oligomer.

As one of ordinary skill in the art would recognise, the 5' nucleotide of an oligonucleotide does not comprise a 5' internucleotide linkage group, although may or may not comprise a 5' terminal group, such as a phophodiester or phosphorothioate suitable for conjugating a linker (B or Y or a conjugate moiety).

Non-naturally occurring nucleotides include nucleotides which have modified sugar moieties, such as bicyclic nucleotides or 2' modified nucleotides, such as 2' substituted nucleotides.

"Nucleotide analogues" are variants of natural nucleotides, such as DNA or RNA nucleotides, by virtue of modifications in the sugar and/or base moieties. Analogues could in principle be merely "silent" or "equivalent" to the natural nucleotides in the context of the oligonucleotide, i.e. have no functional effect on the way the oligonucleotide works to inhibit target gene expression. Such "equivalent" analogues may nevertheless be useful if, for example, they are easier or cheaper to manufacture, or are more stable to storage or manufacturing conditions, or represent a tag or label. Preferably, however, the analogues will have a functional effect on the way in which the oligomer works to inhibit expression; for example by producing increased binding affinity (affinity enhancing) to the target and/or increased resistance to intracellular nucleases and/or increased ease of transport into the cell. Specific examples of nucleoside analogues are described by e.g. Freier & Altmann; *Nucl. Acid Res.*, 1997, 25, 4429-4443 and Uhlmann; *Curr. Opinion in Drug Development*, 2000, 3(2), 293-213, and in Scheme 1:

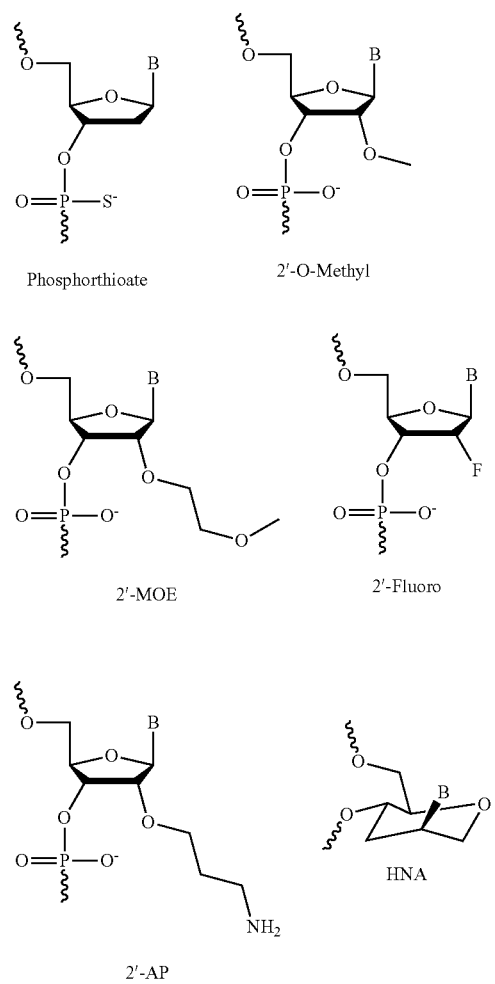

Scheme 1

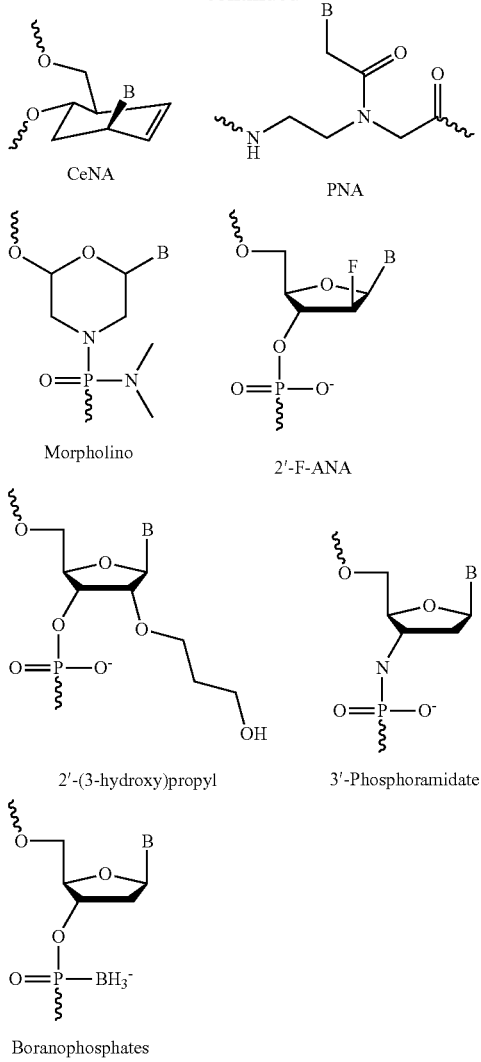

CeNA
PNA
Morpholino
2'-F-ANA
2'-(3-hydroxy)propyl
3'-Phosphoramidate
Boranophosphates The oligomer may thus comprise or consist of a simple sequence of natural occurring nucleotides—preferably 2'-deoxynucleotides (referred here generally as "DNA"), but also possibly ribonucleotides (referred here generally as "RNA"), or a combination of such naturally occurring nucleotides and one or more non-naturally occurring nucleotides, i.e. nucleotide analogues. Such nucleotide analogues may suitably enhance the affinity of the oligomer for the target sequence. Examples of suitable and preferred nucleotide analogues are provided by WO2007/031091 or are referenced therein.

Incorporation of affinity-enhancing nucleotide analogues in the oligomer, such as LNA or 2'-substituted sugars, can allow the size of the specifically binding oligomer to be reduced, and may also reduce the upper limit to the size of the oligomer before non-specific or aberrant binding takes place.

In some embodiments the oligomer comprises at least 2 nucleotide analogues. In some embodiments, the oligomer comprises from 3-8 nucleotide analogues, e.g. 6 or 7 nucleotide analogues.

Examples of nucleotide analogues include modifying the sugar moiety to provide a 2'-substituent group or to produce a bicyclic structure which enhances binding affinity and may also provide increased nuclease resistance.

In some embodiments, nucleotide analogues present within an antisense oligomer of the present invention (such as in regions X' and Y' mentioned in the section "Gapmer Design") are independently selected from, for example: 2'-O-alkyl-RNA units, 2'-OMe-RNA units, 2'-O-alkyl-DNA, 2'-amino-DNA units, 2'-fluoro-DNA units, LNA units, arabino nucleic acid (ANA) units, 2'-fluoro-ANA units, HNA units, INA (intercalating nucleic acid—Christensen, 2002. Nucl. Acids. Res. 2002 30: 4918-4925, hereby incorporated by reference) units and 2'MOE units.

In some embodiments, nucleotide analogues are 2'-O-methoxyethyl-RNA (2'MOE), 2'-fluoro-DNA monomers or LNA nucleotide analogues, and as such an antisense oligonucleotide of the present invention may comprise nucleotide analogues which are independently selected from these three types of analogue, or may comprise only one type of analogue selected from the three types. In some embodiments at least one of said nucleotide analogues is 2'-MOE-RNA, such as 2, 3, 4, 5, 6, 7, 8, 9 or 10 2'-MOE-RNA nucleotide units. In some embodiments, at least one of said nucleotide analogues is 2'-fluoro DNA, such as 2, 3, 4, 5, 6, 7, 8, 9 or 10 2'-fluoro-DNA nucleotide units.

A preferred nucleotide analogue is LNA, such as oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA). Most preferred is beta-D-oxy-LNA.

In some embodiments, there is only one of the above types of nucleotide analogues present in an antisense oligonucleotide of the present invention, or contiguous nucleotide sequence thereof.

In some embodiments, an antisense oligonucleotide of the present invention comprises at least one Locked Nucleic Acid (LNA) unit, such as 1, 2, 3, 4, 5, 6, 7, or 8 LNA units, such as from 3-7 or 4 to 8 LNA units. In the by far most preferred embodiments, at least one of said nucleotide analogues is a locked nucleic acid (LNA); for example at least 3 or at least 4, or at least 5, or at least 6, or at least 7, or 8, of the nucleotide analogues may be LNA. In some embodiments all the nucleotides analogues may be LNA.

In some embodiments, an antisense oligonucleotide of the present invention may comprise both nucleotide analogues (preferably LNA) and DNA units. Preferably, the combined total of nucleotide analogues (preferably LNA) and DNA units is 10-25, such as 10-24, preferably 10-20, such as 10-18, even more preferably 12-16. In some embodiments, the nucleotide sequence of an antisense oligonucleotide of the present invention, such as the contiguous nucleotide sequence, consists of at least one nucleotide analogue (preferably LNA) and the remaining nucleotide units are DNA units. In some embodiments, an antisense oligonucleotide of the present invention comprises only LNA nucleotide analogues and naturally occurring nucleotides (such as RNA or DNA, most preferably DNA nucleotides), optionally with modified internucleotide linkages such as phosphorothioate.

It will be recognised that when referring to a preferred nucleotide sequence motif or nucleotide sequence, which consists of only nucleotides, the oligomers of the invention which are defined by that sequence may comprise a corresponding nucleotide analogue in place of one or more of the nucleotides present in said sequence, such as LNA units or other nucleotide analogues, which raise the duplex stability/$T_m$ of the oligomer/target duplex (i.e. affinity enhancing nucleotide analogue).

$T_m$ Assay:

The oligonucleotide: Oligonucleotide and RNA target (PO) duplexes are diluted to 3 mM in 500 ml RNase-free water and mixed with 500 ml 2× $T_m$-buffer (200 mM NaCl, 0.2 mM EDTA, 20 mM Naphosphate, pH 7.0). The solution is heated to 95° C. for 3 min and then allowed to anneal in room temperature for 30 min. The duplex melting temperatures ($T_m$) is measured on a Lambda 40 UV/VIS Spectrophotometer equipped with a Peltier temperature programmer PTP6 using PE Templab software (Perkin Elmer). The temperature is ramped up from 20° C. to 95° C. and then down to 25° C., recording absorption at 260 nm. First derivative and the local maximums of both the melting and annealing are used to assess the duplex $T_m$.

In some embodiments, any mismatches between the nucleotide sequence of the oligomer and the target sequence are preferably found in regions outside the affinity enhancing nucleotide analogues, such as region Y' as referred to in the section "Gapmer Design, and/or at a position with non-modified, such as DNA nucleotides, in the oligonucleotide, and/or in regions which are 5' or 3' to the contiguous nucleotide sequence.

LNA

The term "LNA" refers to a bicyclic nucleoside analogue which comprises with a bridge between the 2' and 4' position in the ribose ring (2' to 4' bicyclic nucleotide analogue), and is known as "Locked Nucleic Acid".). LNA is in the literature sometimes referred to as BNA (bridged nucleic acid or bicyclic nucleic acid and the two terms may be used interchangeably. The term LNA may refer to an LNA monomer, or, when used in the context of an "LNA oligonucleotide", LNA refers to an oligonucleotide containing one or more such bicyclic nucleotide analogues. In some aspects bicyclic nucleoside analogues are LNA nucleotides, and these terms may therefore be used interchangeably, and is such embodiments, both are be characterized by the presence of a linker group (such as a bridge) between C2' and C4' of the ribose sugar ring.

In some embodiments, an antisense oligonucleotide of the present invention may comprise both beta-D-oxy-LNA, and one or more of the following LNA units: thio-LNA, amino-LNA, oxy-LNA, 5'-methyl-LNA and/or ENA in either the beta-D or alpha-L configurations or combinations thereof. In some embodiments, all LNA cytosine units are 5'-methyl-Cytosine. In some embodiments, at least one nucleoside analogue present in the first region (X') is a bicyclic nucleoside analogue, such as at least 2, at least 3, at least 4, at least 5, at least 6, at least 7, at least 8, (except the DNA and or RNA nucleosides of region Y') are sugar modified nucleoside analogues, such as such as bicyclic nucleoside analogues, such as LNA, e.g. beta-D-X-LNA or alpha-L-X-LNA (wherein X is oxy, amino or thio), or other LNAs disclosed herein including, but not limited to, (R/S) cET, cMOE or 5'-Me-LNA.

In some embodiments the LNA used in the oligonucleotide compounds of the invention preferably has the structure of the general formula II:

Formula II

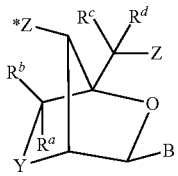

wherein Y is selected from the group consisting of —O—, —CH₂O—, —S—, —NH—, N(R$^e$) and/or —CH₂—; Z and Z* are independently selected among an internucleotide linkage, R$^H$, a terminal group or a protecting group; B constitutes a natural or non-natural nucleotide base moiety (nucleobase), and R$^H$ is selected from hydrogen and $C_{1-4}$-alkyl; R$^a$, R$^b$ R$^C$, R$^d$ and R$^e$ are, optionally independently, selected from the group consisting of hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents R$^a$ and R$^b$ together may designate optionally substituted methylene (=CH₂); and R$^H$ is selected from hydrogen and $C_{1-4}$-alkyl. In some embodiments R$^a$, R$^b$ R$^C$, R$^d$ and R$^e$ are, optionally independently, selected from the group consisting of hydrogen and $C_{1-6}$alkyl, such as methyl. For all chiral centers, asymmetric groups may be found in either R or S orientation, for example, two exemplary stereochemical isomers include the beta-D and alpha-L isoforms, which may be illustrated as follows:

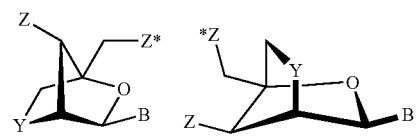

Specific exemplary LNA units are shown below:

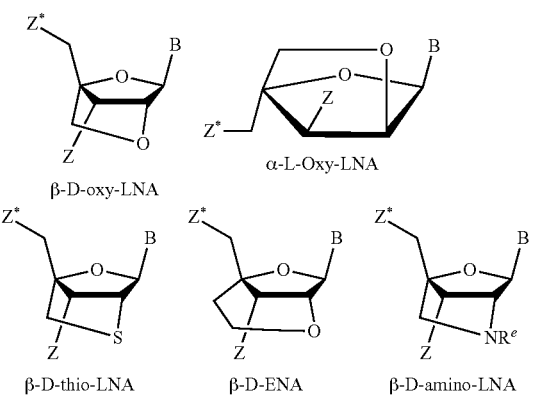

β-D-oxy-LNA    α-L-Oxy-LNA

β-D-thio-LNA    β-D-ENA    β-D-amino-LNA

The term "thio-LNA" comprises a locked nucleotide in which Y in the general formula above is selected from S or —CH₂—S—. Thio-LNA can be in both beta-D and alpha-L-configuration.

The term "amino-LNA" comprises a locked nucleotide in which Y in the general formula above is selected from —N(H)—, N(R)—, $CH_2$—N(H)—, and —$CH_2$—N(R)— where R is selected from hydrogen and $C_{1-4}$-alkyl. Amino-LNA can be in both beta-D and alpha-L-configuration.

The term "oxy-LNA" comprises a locked nucleotide in which Y in the general formula above represents —O—. Oxy-LNA can be in both beta-D and alpha-L-configuration.

The term "ENA" comprises a locked nucleotide in which Y in the general formula above is —$CH_2$—O— (where the oxygen atom of —$CH_2$—O— is attached to the 2'-position relative to the base B). $R^e$ is hydrogen or methyl.

In some exemplary embodiments LNA is selected from beta-D-oxy-LNA, alpha-L-oxy-LNA, beta-D-amino-LNA and beta-D-thio-LNA, in particular beta-D-oxy-LNA.

As used herein, "bicyclic nucleosides" refer to modified nucleosides comprising a bicyclic sugar moiety. Examples of bicyclic nucleosides include, without limitation, nucleosides comprising a bridge between the 4' and the 2' ribosyl ring atoms. In some embodiments, compounds provided herein include one or more bicyclic nucleosides wherein the bridge comprises a 4' to 2' bicyclic nucleoside. Examples of such 4' to 2' bicyclic nucleosides, include, but are not limited to, one of the formulae: 4'-($CH_2$)—O-2' (LNA); 4'-($CH_2$)—S-2'; 4'-($CH_2$)$_2$—O-2' (ENA); 4'-CH($CH_3$)—O-2' and 4'-CH($CH_2OCH_3$)—O-2', and analogs thereof (see, U.S. Pat. No. 7,399,845, issued on Jul. 15, 2008); 4'-C($CH_3$)($CH_3$)—O-2', and analogs thereof (see, published PCT International Application WO2009/006478, published Jan. 8, 2009); 4'-$CH_2$—N(O$CH_3$)-2', and analogs thereof (see, published PCT International Application WO2008/150729, published Dec. 11, 2008); 4'-$CH_2$—O—N($CH_3$)-2' (see, published U.S. Patent Application US2004/0171570, published Sep. 2, 2004); 4'-$CH_2$—N(R)—O-2', wherein R is H, $C_1$-$C_{10}$ alkyl, or a protecting group (see, U.S. Pat. No. 7,427,672, issued on Sep. 23, 2008); 4'-$CH_2$—C(H)($CH_3$)-2' (see, Chattopadhyaya, et al, J. Org. Chem., 2009, 74, 118-134); and 4'-$CH_2$—C(=$CH_2$)-2', and analogs thereof (see, published PCT International Application WO 2008/154401, published on Dec. 8, 2008). Also see, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A, 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc, 129(26) 8362-8379 (Jul. 4, 2007); Elayadi et al., Curr. Opinion Invens. Drugs, 2001, 2, 558-561; Braasch et al., Chem. Biol, 2001, 8, 1-7; Oram et al, Curr. Opinion Mol. Ther., 2001, 3, 239-243; U.S. Pat. Nos. 6,670,461, 7,053,207, 6,268,490, 6,770,748, 6,794,499, 7,034,133, 6,525,191, 7,399,845; published PCT International applications WO 2004/106356, WO 94/14226, WO 2005/021570, and WO 2007/134181; U.S. Patent Publication Nos. US2004/0171570, US2007/0287831, and US2008/0039618; and U.S. patent Ser. Nos. 12/129,154, 60/989,574, 61/026,995, 61/026,998, 61/056,564, 61/086,231, 61/097,787, and 61/099,844; and PCT International Application Nos. PCT/US2008/064591, PCT/US2008/066154, and PCT/US2008/068922. Each of the foregoing bicyclic nucleosides can be prepared having one or more stereochemical sugar configurations including for example a-L-ribofuranose and beta-D-ribofuranose (see PCT international application PCT DK98/00393, published on Mar. 25, 1999 as WO 99/14226).

In some embodiments, bicyclic sugar moieties of LNA nucleosides include, but are not limited to, compounds having at least one bridge between the 4' and the 2' position of the pentofuranosyl sugar moiety wherein such bridges independently comprises 1 or from 2 to 4 linked groups independently selected from —[$CiR_aXR_b$)]—, —C($R_a$)=C($R_b$)—, —C($R_a$)=N—, —C(=$NR_a$)—, —C(=O)—, —C(=S)—, —O—, —Si($R_a$)$_2$—, —S(=O)$_x$—, and —N(Ra)—; wherein: x is 0, 1, or 2; n is 1, 2, 3, or 4; each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_6$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_2$ alkynyl, $C_5$-$C_{20}$ aryl, substituted $C_5$-$C_{20}$ aryl, acyl (C(=O)—H), substituted acyl, a heterocycle radical, a substituted heterocycle radical, C1-$C_{12}$ aminoalkyl, substituted $C_1$-$C_{12}$ aminoalkyl, or a protecting group.

In some embodiments, the bridge of a bicyclic sugar moiety is, —[C($R_a$)(Rb)]$_n$—, —[C($R_a$)($R_b$)]$_n$—O—, —C($R_aR_b$)—N(R)—O— or, —C($R_aR_b$)—O—N(R)—. In some embodiments, the bridge is 4'-$CH_2$-2', 4'-($CH_2$)$_2$-2', 4'-($CH_2$)$_3$-2', 4'-$CH_2$—O-2', 4'-($CH_2$)$_2$—O-2', 4'-$CH_2$—O—N(R)-2', and 4'-$CH_2$—N(R)—O-2'-, wherein each R is, independently, H, a protecting group, or $C_1$-$C_{12}$ alkyl.

In some embodiments, bicyclic nucleosides are further defined by isomeric configuration. For example, a nucleoside comprising a 4'-2' methylene-oxy bridge, may be in the a-L configuration or in the beta-D configuration. Previously, a-L-methyleneoxy (4'-$CH_2$—O-2') BNA's have been incorporated into antisense oligonucleotides that showed antisense activity (Frieden et al, Nucleic Acids Research, 2003, 21, 6365-6372).

In some embodiments, bicyclic nucleosides include, but are not limited to, (A) a-L-Methyleneoxy (4'-$CH_2$—O-2') BNA, (B) beta-D-Methyleneoxy (4'-$CH_2$—O-2') BNA, (C) Ethyleneoxy (4'-($CH_2$)$_2$—O-2') BNA, (D) Aminooxy (4'-$CH_2$—O—N(R)-2') BNA, (E) Oxyamino (4'-$CH_2$—N(R)—O-2') BNA, (F), Methyl(methyleneoxy) (4'-CH($CH_3$)—O-2') BNA, (G) methylene-thio (4'-$CH_2$—S-2') BNA, (H) methylene-amino (4'-$CH_2$—N(R)-2') BNA, (I) methyl carbocyclic (4'-$CH_2$—CH($CH_3$)-2') BNA, and (J) propylene carbocyclic (4'-($CH_2$)$_3$-2') BNA as depicted below.

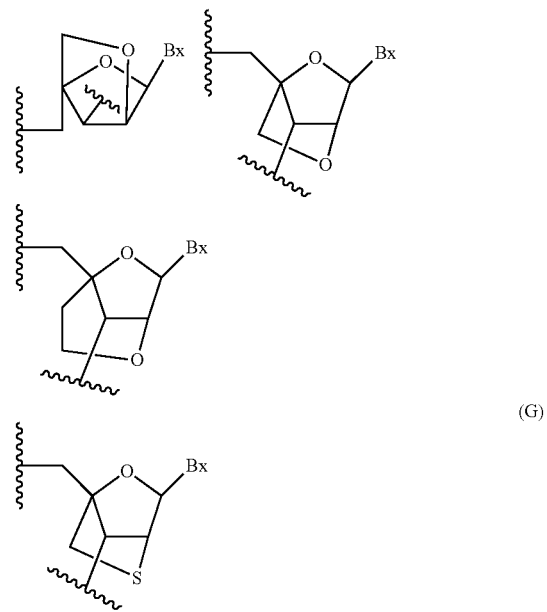

-continued (H)
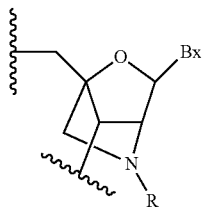

(I)
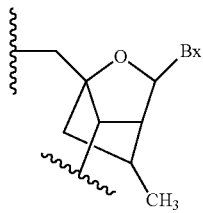

(J)
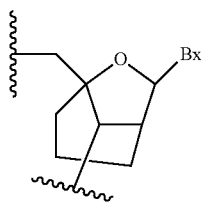

wherein Bx is the base moiety and R is, independently, H, a protecting group or $C_1$-$C_2$ alkyl.

In some embodiments, bicyclic nucleoside is defined by Formula I:

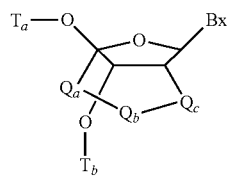
I wherein:
Bx is a heterocyclic base moiety;
-$Q_a$-$Q_b$-$Q_c$- is —$CH_2$—N(Rc)-$CH_2$—, —C(=O)—N($R_c$)—$CH_2$—, —$CH_2$—O—N(Rc)-, —$CH_2$—N(Rc)-O—, or —N(Rc)-O—$CH_2$;
$R_c$ is $C_1$-$C_{12}$ alkyl or an amino protecting group; and
$T_a$ and $T_b$ are each, independently, H, a hydroxyl protecting group, a conjugate group, a reactive phosphorus group, a phosphorus moiety, or a covalent attachment to a support medium.

In some embodiments, bicyclic nucleoside is defined by Formula II:

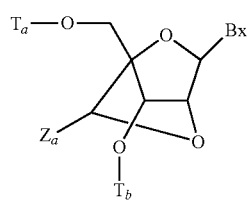
II wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium; $Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol, or substituted thio.

In some embodiments, each of the substituted groups is, independently, mono or poly substituted with substituent groups independently selected from halogen, oxo, hydroxyl, $OJ_c$, $NJ_d$, $SJ_c$, $N_3$, OC(=X)$J_c$, and $NJ_eC$(=X)$NJ_cJ_d$, wherein each $J_c$, $J_d$, and $J_e$ is, independently, H, $C_1$-$C_6$ alkyl, or substituted $C_1$-$C_6$ alkyl and X is O or $NJ_c$.

In some embodiments, bicyclic nucleoside is defined by Formula III:

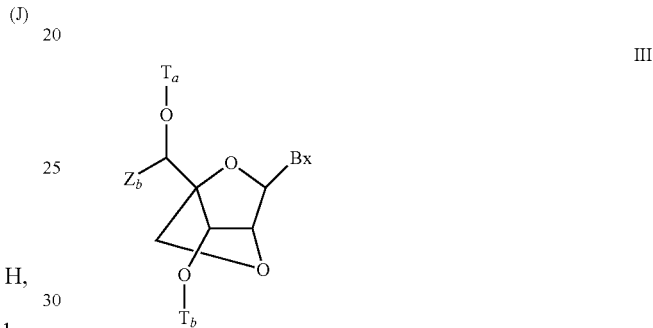
III wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium;
$R_d$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, or substituted acyl (C(=O)—).

In some embodiments, bicyclic nucleoside is defined by Formula IV:

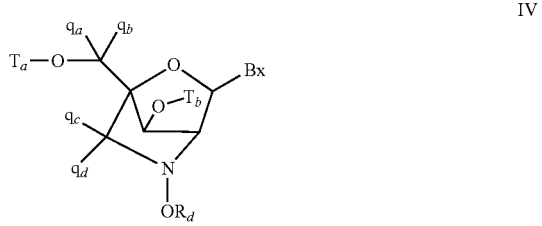
IV wherein:
Bx is a heterocyclic base moiety;
$T_a$ and $T_b$ are each, independently H, a hydroxyl protecting group, a conjugate group, a reactive phosphorus group, a phosphorus moiety, or a covalent attachment to a support medium;
$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl; each $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl, $C_1$-$C_6$ alkoxyl, substituted $Q$-$C_6$ alkoxyl, acyl, substituted acyl, $C_1$-$C_6$ aminoalkyl, or substituted $C_1$-$C_6$ aminoalkyl;

In some embodiments, bicyclic nucleoside is defined by Formula V:

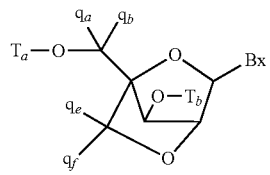

V wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium; $q_a$, $q_b$, $q_c$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SO_2J_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; or $q_e$ and $q_f$ together are =C($q_g$)($q_h$); $q_g$ and $q_h$ are each, independently, H, halogen, $C_1$-$C_{12}$ alkyl, or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine, and uracil, along with their oligomerization, and nucleic acid recognition properties have been described (see, e.g., Koshkin et al., Tetrahedron, 1998, 54, 3607-3630). BNAs and preparation thereof are also described in WO 98/39352 and WO 99/14226.

Analogs of methyleneoxy (4'-$CH_2$—O-2') BNA, methyleneoxy (4'-$CH_2$—O-2') BNA, and 2'-thio-BNAs, have also been prepared {see, e.g., Kumar et al., Bioorg. Med. Chem. Lett., 1998, 8, 2219-2222). Preparation of locked nucleoside analogs comprising oligodeoxyribonucleotide duplexes as substrates for nucleic acid polymerases has also been described (see, e.g., Wengel et al., WO 99/14226). Furthermore, synthesis of 2'-amino-BNA, a novel conformationally restricted high-affinity oligonucleotide analog, has been described in the art (see, e.g., Singh et al., J. Org. Chem., 1998, 63, 10035-10039). In addition, 2'-amino- and 2'-methylamino-BNA's have been prepared and the thermal stability of their duplexes with complementary RNA and DNA strands has been previously reported.

In some embodiments, the bicyclic nucleoside is defined by Formula VI:

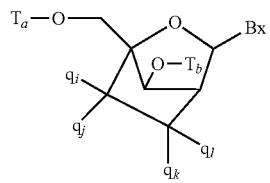

VI wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium; each qj, qj, $q_k$ and ql is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_2$-$C_{12}$ alkoxyl, $OJ_j$, $SJ_j$, $SO_2J_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$, or (H)C(=S)$NJ_jJ_k$; and qi and $q_j$ or ql and $q_k$ together are =C($q_g$)($q_h$), wherein $q_g$ and $q_h$ are each, independently, H, halogen, $C_1$-$C_{12}$ alkyl, or substituted $C_1$-$C_6$ alkyl.

One carbocyclic bicyclic nucleoside having a 4'-($CH_2$)$_3$-2' bridge and the alkenyl analog, bridge 4'-CH=CH—$CH_2$-2', have been described (see, e.g., Freier et al, Nucleic Acids Research, 1997, 25(22), 4429-4443 and Albaek et al, J. Org. Chem., 2006, 71, 7731-77 '40). The synthesis and preparation of carbocyclic bicyclic nucleosides along with their oligomerization and biochemical studies have also been described (see, e.g., Srivastava et al, J. Am. Chem. Soc. 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting the 2' carbon atom and the 4' carbon atom.

As used herein, "monocylic nucleosides" refer to nucleosides comprising modified sugar moieties that are not bicyclic sugar moieties. In some embodiments, the sugar moiety, or sugar moiety analogue, of a nucleoside may be modified or substituted at any position.

As used herein, "2'-modified sugar" means a furanosyl sugar modified at the 2' position. In some embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In some embodiments, 2' modifications are selected from substituents including, but not limited to: O[($CH_2$)$_n$O]$_m$$CH_3$, O($CH_2$)$_n$$NH_2$, O($CH_2$)$_n$$CH_3$, O($CH_2$)$_n$$ONH_2$, $OCH_2$C(=O)N(H)$CH_3$, and O($CH_2$)$_n$ON[($CH_2$)$_n$$CH_3$]2, where n and m are from 1 to about 10. Other 2'-substituent groups can also be selected from: $C_1$-$C_{12}$ alkyl; substituted alkyl; alkenyl; alkynyl; alkaryl; aralkyl; O-alkaryl or O-aralkyl; SH; $SCH_3$; OCN; Cl; Br; CN; $CF_3$; $OCF_3$; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an R; a cleaving group; a reporter group; an intercalator; a group for improving pharmacokinetic properties; and a group for improving the pharmacodynamic properties of an antisense compound, and other substituents having similar properties. In some embodiments, modified nucleosides comprise a 2'-MOE side chain {see, e.g., Baker et al., J. Biol. Chem., 1997, 272, 1 1944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2-MOE substituent also have been shown to be antisense inhibitors of gene expression with promising features for in vivo use {see, e.g., Martin, P., Helv. Chim. Acta, 1995, 78, 486-504; Altmann et al., Chimia, 1996, 50, 168-176; Altmann et al., Biochem.

Soc. Trans., 1996, 24, 630-637; and Altmann et al., Nucleosides Nucleotides, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified ?THP nucleosides include, but are not limited to, what is referred to in the art as hexitol nucleic acid (HNA), anitol nucleic acid (ANA), manitol nucleic acid (MNA) {see Leumann, C J. Bioorg. and Med. Chem. (2002) 10:841-854), fluoro HNA (F-HNA), or those compounds defined by Formula X:

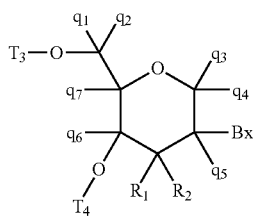

Formula X wherein independently for each of said at least one tetrahydropyran nucleoside analog of Formula X:

Bx is a heterocyclic base moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and T4 is H, a hydroxyl protecting group, a linked conjugate group, or a 5' or 3'-terminal group; $q_1$ $q_2$ $q_3$ $q_4$ $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and one of R, and $R_2$ is hydrogen and the other is selected from halogen, substituted or unsubstituted alkoxy, NJ, $J_2$, SJ, $N_3$, OC(=X) $J_1$, OC(=X)$NJ_1J_2$, $NJ_3$C(=X) $NJ_1J_2$, and CN, wherein X is O, S, or $NJ_1$ and each $J_1$, $J_2$, and $J_3$ is, independently, H or $C_1$-$C_6$ alkyl.

In some embodiments, the modified THP nucleosides of Formula X are provided wherein $q_m$, $q_n$, $q_p$, $q_r$, $q_s$, $q_t$, and $q_u$ are each H. In some embodiments, at least one of $q_m$, $q_n$, $q_p$, $q_r$, $q_s$, $q_t$ and $q_u$ is other than H. In some embodiments, at least one of $q_m$, $q_n$, $q_p$, $q_r$, $q_s$, $q_t$ and $q_u$ is methyl. In some embodiments, THP nucleosides of Formula X are provided wherein one of R, and $R_2$ is F. In some embodiments, $R_1$ is fluoro and $R_2$ is H, R, is methoxy and $R_2$ is H, and R, is methoxyethoxy and $R_2$ is H.

As used herein, "2'-modified" or "2'-substituted" refers to a nucleoside comprising a sugar comprising a substituent at the 2' position other than H or OH. 2'-modified nucleosides, include, but are not limited to nucleosides with non-bridging 2'substituents, such as allyl, amino, azido, thio, O-allyl, O—$C_1$-$C_{10}$alkyl, —$OCF_3$, O—$(CH_2)_2$—O—$CH_3$, 2'-O $(CH_2)_2SCH_3$, O—$(CH_2)_2$—O—$N(R_m)(R_n)$, or O—$CH_2$—C(=O)—$N(R_m)(R_n)$, where each $R_m$ and $R_n$ is, independently, H or substituted or unsubstituted $C_1$-$C_{10}$ alkyl. 2'-modified nucleosides may further comprise other modifications, for example, at other positions of the sugar and/or at the nucleobase.

As used herein, "2'-F" refers to a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "oligonucleotide" refers to a compound comprising a plurality of linked nucleosides.

In some embodiments, one or more of the plurality of nucleosides is modified. In some embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds {see, e.g., review article: Leumann, J. C, Bioorganic and Medicinal Chemistry, 2002, 10, 841-854). Such ring systems can undergo various additional substitutions to enhance activity. Methods for the preparations of modified sugars are well known to those skilled in the art. In nucleotides having modified sugar moieties, the nucleobase moieties (natural, modified, or a combination thereof) are maintained for hybridization with an appropriate nucleic acid target.

In some embodiments, antisense compounds comprise one or more nucleotides having modified sugar moieties. In some embodiments, the modified sugar moiety is 2'-MOE. In some embodiments, the 2'-MOE modified nucleotides are arranged in a gapmer motif. In some embodiments, the modified sugar moiety is a cEt. In some embodiments, the cEt modified nucleotides are arranged throughout the wings of a gapmer motif.

In some embodiments, in the LNA, $R^{4*}$ and $R^{2*}$ together designate the biradical —O—CH($CH_2OCH_3$)— (2'O-methoxyethyl bicyclic nucleic acid—Seth at al., 2010, J. Org. Chem)—in either the R- or S-configuration.

In some embodiments, in the LNA, $R^{4*}$ and $R^{2*}$ together designate the biradical —O—CH($CH_2CH_3$)— (2'O-ethyl bicyclic nucleic acid—Seth at al., 2010, J. Org. Chem).—in either the R- or S-configuration.

In some embodiments, in the LNA, $R^{4*}$ and $R^{2*}$ together designate the biradical —O—CH($CH_3$)—.—in either the R- or S-configuration. In some embodiments, $R^{4*}$ and $R^{2*}$ together designate the biradical —O—$CH_2$—O—$CH_2$— (Seth at al., 2010, J. Org. Chem).

In some embodiments, in the LNA, $R^{4*}$ and $R^{2*}$ together designate the biradical —O—NR—$CH_3$—(Seth at al., 2010, J. Org. Chem).

In some embodiments, the LNA units have a structure selected from the following group:

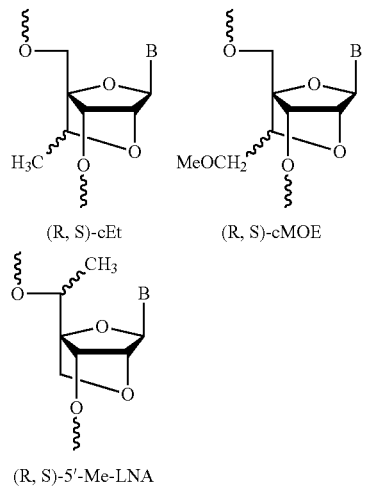

Incorporation of affinity-enhancing nucleotide analogues in the oligomer, such as LNA or 2'-substituted sugars, can allow the size of the specifically binding oligomer to be reduced, and may also reduce the upper limit to the size of the oligomer before non-specific or aberrant binding takes place.

We have evaluated the nephrotoxicity of a cET compound (using (S)-cET, with the sequence (Compound ID 6/411847 of WO2009/12495 and a comparative beta-D-oxy LNA compound (6/392063 of WO2009/12495) and found that the cET compounds elicit surprisingly high nephrotoxicity as compared to the beta-D-oxy LNA control. The study was a single dose study, with sacrifice after 3 days (see EP1984381 example 41 for the methodology, although we used NMRI mice). Nephrotoxicity was confirmed by histological analysis. Notably signs of nephrotoxicity we seen at dosages of the cET compound below those where serum ALT was noted, indicating that for cET compounds, nephrotoxicity may be a particular problem. The use of the conjugates of the present invention, such as trivalent GalNAc conjugates are therefore highly useful in reducing the nephrotoxicity of LNA compounds, such as cET compounds.

In some embodiments, the oligomer comprises at least 1 nucleoside analogue. In some embodiments the oligomer comprises at least 2 nucleotide analogues. In some embodiments, the oligomer comprises from 3-8 nucleotide analogues, e.g. 6 or 7 nucleotide analogues. In the by far most preferred embodiments, at least one of said nucleotide analogues is a locked nucleic acid (LNA); for example at least 3 or at least 4, or at least 5, or at least 6, or at least 7, or 8, of the nucleotide analogues may be LNA. In some embodiments all the nucleotides analogues may be LNA.

It will be recognized that when referring to a preferred nucleotide sequence motif or nucleotide sequence, which consists of only nucleotides, the oligomers of the invention which are defined by that sequence may comprise a corresponding nucleotide analogue in place of one or more of the nucleotides present in said sequence, such as LNA units or other nucleotide analogues, which raise the duplex stability/$T_m$ of the oligomer/target duplex (i.e. affinity enhancing nucleotide analogues).

A preferred nucleotide analogue is LNA, such as oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA).

In some embodiments, the oligomer of the invention, such as region A, may comprise LNA units and other nucleotide analogues, further nucleotide analogues present within the oligomer of the invention are independently selected from, for example: 2'-O-alkyl-RNA units, 2'-amino-DNA units, 2'-fluoro-DNA units, LNA units, arabino nucleic acid (ANA) units, 2'-fluoro-ANA units, HNA units, INA (intercalating nucleic acid—Christensen, 2002. Nucl. Acids. Res. 2002 30: 4918-4925, hereby incorporated by reference) units and 2'MOE units. In some embodiments there is only one of the above types of nucleotide analogues present in the oligomer of the invention, such as the first region, or contiguous nucleotide sequence thereof.

In some embodiments, the oligomer according to the invention (region A) may therefore comprises at least one Locked Nucleic Acid (LNA) unit, such as 1, 2, 3, 4, 5, 6, 7, or 8 LNA units, such as from 3-7 or 4 to 8 LNA units, or 3, 4, 5, 6 or 7 LNA units. In some embodiments, all the nucleotide analogues are LNA. In some embodiments, the oligomer may comprise both beta-D-oxy-LNA, and one or more of the following LNA units: thio-LNA, amino-LNA, oxy-LNA, and/or ENA in either the beta-D or alpha-L configurations or combinations thereof. In some embodiments all LNA, cytosine units are 5'methyl-Cytosine. In some embodiments of the invention, the oligomer (such as the first and optionally second regions) may comprise both LNA and DNA units. In some embodiments, the combined total of LNA and DNA units is 10-25, such as 10-24, preferably 10-20, such as 10-18, such as 12-16. In some embodiments of the invention, the nucleotide sequence of the oligomer, of first region thereof, such as the contiguous nucleotide sequence consists of at least one LNA and the remaining nucleotide units are DNA units. In some embodiments the oligomer, or first region thereof, comprises only LNA, nucleotide analogues and naturally occurring nucleotides (such as RNA or DNA, most preferably DNA nucleotides), optionally with modified internucleotide linkages such as phosphorothioate.

RNAse Recruitment

It is recognized that an oligomeric compound may function via non RNase mediated degradation of target mRNA, such as by steric hindrance of translation, or other methods, In some embodiments, the oligomers of the invention are capable of recruiting an endoribonuclease (RNase), such as RNase H.

It is preferable such oligomers, such as region A, or contiguous nucleotide sequence, comprises of a region of at least 4, such as at least 5, such as at least 6, such as at least 7 consecutive nucleotide units, such as at least 8 or at least 9 consecutive nucleotide units (residues), including 7, 8, 9, 10, 11, 12, 13, 14, 15 or 16 consecutive nucleotides, which, when formed in a duplex with the complementary target RNA is capable of recruiting RNase (such as DNA units). The contiguous sequence which is capable of recruiting RNAse may be region Y' as referred to in the context of a gapmer as described herein. In some embodiments the size of the contiguous sequence which is capable of recruiting RNAse, such as region Y', may be higher, such as 10, 11, 12, 13, 14, 15, 16, 17, 18, 19 or 20 nucleotide units.

EP 1 222 309 provides in vitro methods for determining RNaseH activity, which may be used to determine the ability to recruit RNaseH. A oligomer is deemed capable of recruiting RNase H if, when provided with the complementary RNA target, it has an initial rate, as measured in pmol/l/min, of at least 1%, such as at least 5%, such as at least 10% or more than 20% of the of the initial rate determined using DNA only oligonucleotide, having the same base sequence but containing only DNA monomers, with no 2' substitutions, with phosphorothioate linkage groups between all monomers in the oligonucleotide, using the methodology provided by Example 91-95 of EP 1 222 309.

In some embodiments, an oligomer is deemed essentially incapable of recruiting RNaseH if, when provided with the complementary RNA target, and RNaseH, the RNaseH initial rate, as measured in pmol/l/min, is less than 1%, such as less than 5%, such as less than 10% or less than 20% of the initial rate determined using the equivalent DNA only oligonucleotide, with no 2' substitutions, with phosphorothioate linkage groups between all nucleotides in the oligonucleotide, using the methodology provided by Example 91-95 of EP 1 222 309.

In other embodiments, an oligomer is deemed capable of recruiting RNaseH if, when provided with the complementary RNA target, and RNaseH, the RNaseH initial rate, as measured in pmol/l/min, is at least 20%, such as at least 40%, such as at least 60%, such as at least 80% of the initial rate determined using the equivalent DNA only oligonucleotide, with no 2' substitutions, with phosphorothioate linkage groups between all nucleotides in the oligonucleotide, using the methodology provided by Example 91-95 of EP 1 222 309.

Typically the region of the oligomer which forms the consecutive nucleotide units which, when formed in a duplex with the complementary target RNA is capable of recruiting RNase consists of nucleotide units which form a DNA/RNA like duplex with the RNA target. The oligomer of the invention, such as the first region, may comprise a nucleotide sequence which comprises both nucleotides and nucleotide analogues, and may be e.g. in the form of a gapmer.

Gapmer Design

In some embodiments, the oligomer of the invention, such as the first region, comprises or is a gapmer. A gapmer oligomer is an oligomer which comprises a contiguous stretch of nucleotides which is capable of recruiting an RNAse, such as RNAseH, such as a region of at least 6 or 7 DNA nucleotides, referred to herein in as region Y' (Y'), wherein region Y' is flanked both 5' and 3' by regions of affinity enhancing nucleotide analogues, such as from 1-6 nucleotide analogues 5' and 3' to the contiguous stretch of nucleotides which is capable of recruiting RNAse—these regions are referred to as regions X' (X') and Z' (Z'), respectively. The X' and Z' regions can also be termed the wings of the Gapmer. Examples of gapmers are disclosed in WO2004/046160, WO2008/113832, and WO2007/146511.

In some embodiments, the monomers which are capable of recruiting RNAse are selected from the group consisting of DNA monomers, alpha-L-LNA monomers, C4' alkylayted DNA monomers (see PCT/EP2009/050349 and Vester et al., Bioorg. Med. Chem. Lett. 18 (2008) 2296-2300, hereby incorporated by reference), and UNA (unlinked nucleic acid) nucleotides (see Fluiter et al., Mol. Biosyst., 2009, 10, 1039 hereby incorporated by reference). UNA is unlocked nucleic acid, typically where the C2-C3 C—C bond of the ribose has been removed, forming an unlocked "sugar" residue. Preferably the gapmer comprises a (poly)nucleotide sequence of formula (5' to 3'), X'—Y'—Z', wherein; region X' (X') (5' region) consists or comprises of at least one nucleotide analogue, such as at least one LNA unit, such as from 1-6 nucleotide analogues, such as LNA units, and; region Y' (Y') consists or comprises of at least four or at least five consecutive nucleotides which are capable of recruiting RNAse (when formed in a duplex with a complementary RNA molecule, such as the mRNA target), such as DNA nucleotides, and; region Z' (Z') (3'region) consists or comprises of at least one nucleotide analogue, such as at least one LNA unit, such as from 1-6 nucleotide analogues, such as LNA units.

In some embodiments, region X' consists of 1, 2, 3, 4, 5 or 6 nucleotide analogues, such as LNA units, such as from 2-5 nucleotide analogues, such as 2-5 LNA units, such as 3 or 4 nucleotide analogues, such as 3 or 4 LNA units; and/or region Z consists of 1, 2, 3, 4, 5 or 6 nucleotide analogues, such as. LNA units, such as from 2-5 nucleotide analogues, such as 2-5 LNA units, such as 3 or 4 nucleotide analogues, such as 3 or 4 LNA units.

In some embodiments Y' consists or comprises of 4, 5, 6, 7, 8, 9, 10, 11 or 12 consecutive nucleotides which are capable of recruiting RNAse, or from 4-12 or from 6-10, or from 7-9, such as 8 consecutive nucleotides which are capable of recruiting RNAse. In some embodiments region Y' consists or comprises at least one DNA nucleotide unit, such as 1-12 DNA units, preferably from 4-12 DNA units, more preferably from 6-10 DNA units, such as from 7-10 DNA units, most preferably 8, 9 or 10 DNA units.

In some embodiments region X' consist of 3 or 4 nucleotide analogues, such as LNA, region X' consists of 7, 8, 9 or 10 DNA units, and region Z' consists of 3 or 4 nucleotide analogues, such as LNA. Such designs include (X'—Y'—Z') 3-10-3, 3-10-4, 4-10-3, 3-9-3, 3-9-4, 4-9-3, 3-8-3, 3-8-4, 4-8-3, 3-7-3, 3-7-4, 4-7-3. In a preferred embodiment the gapmer is a 3-9-4 gapmer, even more preferred it is a 3-10-3 gapmer.

Further gapmer designs are disclosed in WO2004/046160, which is hereby incorporated by reference. WO2008/113832, which claims priority from U.S. provisional application 60/977,409 hereby incorporated by reference, refers to 'shortmer' gapmer oligomers. In some embodiments, oligomers presented here may be such shortmer gapmers.

In some embodiments the oligomer, e.g. region X', is consisting of a contiguous nucleotide sequence of a total of 10, 11, 12, 13 or 14 nucleotide units, wherein the contiguous nucleotide sequence comprises or is of formula (5'-3'), X'—Y'—Z' wherein; X' consists of 1, 2 or 3 nucleotide analogue units, such as LNA units; Y' consists of 7, 8 or 9 contiguous nucleotide units which are capable of recruiting RNAse when formed in a duplex with a complementary RNA molecule (such as a mRNA target); and Z' consists of 1, 2 or 3 nucleotide analogue units, such as LNA units.

In some embodiments X' consists of 1 LNA unit. In some embodiments X' consists of 2 LNA units. In some embodiments X' consists of 3 LNA units. In some embodiments Z' consists of 1 LNA units. In some embodiments Z' consists of 2 LNA units. In some embodiments Z' consists of 3 LNA units. In some embodiments Y' consists of 7 nucleotide units. In some embodiments Y' consists of 8 nucleotide units. In some embodiments Y' consists of 9 nucleotide units. In certain embodiments, region Y' consists of 10 nucleoside monomers. In certain embodiments, region Y' consists or comprises 1-10 DNA monomers. In some embodiments Y' comprises of from 1-9 DNA units, such as 2, 3, 4, 5, 6, 7, 8 or 9 DNA units. In some embodiments Y' consists of DNA units. In some embodiments Y' comprises of at least one LNA unit which is in the alpha-L configuration, such as 2, 3, 4, 5, 6, 7, 8 or 9 LNA units in the alpha-L-configuration. In some embodiments Y' comprises of at least one alpha-L-oxy LNA unit or wherein all the LNA units in the alpha-L-configuration are alpha-L-oxy LNA units. In some embodiments the number of nucleotides present in X'—Y'—Z' are selected from the group consisting of (nucleotide analogue units—region Y'—nucleotide analogue units): 1-8-1, 1-8-2, 2-8-1, 2-8-2, 3-8-3, 2-8-3, 3-8-2, 4-8-1, 4-8-2, 1-8-4, 2-8-4, or; 1-9-1, 1-9-2, 2-9-1, 2-9-2, 2-9-3, 3-9-2, 1-9-3, 3-9-1, 4-9-1, 1-9-4, or; 1-10-1, 1-10-2, 2-10-1, 2-10-2, 1-10-3, 3-10-1, 2-10-3, 3-10-2. In some embodiments the number of nucleotides in X'—Y'—Z' are selected from the group consisting of: 2-7-1, 1-7-2, 2-7-2, 3-7-3, 2-7-3, 3-7-2, 3-7-4, and 4-7-3. In certain embodiments, each of regions X' and Y' consists of three LNA monomers, and region Y' consists of 8 or 9 or 10 nucleoside monomers, preferably DNA monomers. In some embodiments both X' and Z' consists of two LNA units each, and Y' consists of 8 or 9 nucleotide units, preferably DNA units. In various embodiments, other gapmer designs include those where regions X' and/or Z' consists of 3, 4, 5 or 6 nucleoside analogues, such as monomers containing a 2'-O-methoxy-ethyl-ribose sugar (2'-MOE) or monomers containing a 2'-fluoro-deoxyribose sugar, and region Y' consists of 8, 9, 10, 11 or 12 nucleosides, such as DNA monomers, where regions X'—Y'—Z' have 3-9-3, 3-10-3, 5-10-5 or 4-12-4 monomers. Further gapmer designs are disclosed in WO 2007/146511A2, hereby incorporated by reference.

LNA Gapmers: A LNA gapmer is a gapmer oligomer (region A) which comprises at least one LNA nucleotide. SEQ ID NO 1, 2, 3, 4, 5, 6, 7, 8 and 40 are LNA gapmer oligomers. The oligomers with a contiguous sequence of 10-16 nucleotides which are complementary to a corresponding length of SEQ ID NO 33 or 34 or 45 may also be gapmer oligomers such as LNA gapmers.

Internucleotide Linkages

The nucleoside monomers of the oligomers (e.g. first and second regions) described herein are coupled together via internucleoside linkage groups. Suitably, each monomer is linked to the 3' adjacent monomer via a linkage group.

The person having ordinary skill in the art would understand that, in the context of the present invention, the 5' monomer at the end of an oligomer does not comprise a 5' linkage group, although it may or may not comprise a 5' terminal group, or a linkage group for conjugation.

The terms "linkage group" or "internucleotide linkage" are intended to mean a group capable of covalently coupling together two nucleotides. Specific and preferred examples include phosphate groups and phosphorothioate groups. Internucleoside linkage may be used interchangeably with internucleotide linkage.

The nucleotides of the oligomer of the invention or contiguous nucleotides sequence thereof are coupled together via linkage groups. Suitably each nucleotide is linked to the 3' adjacent nucleotide via a linkage group.

Suitable internucleotide linkages include those listed within WO2007/031091, for example the internucleotide linkages listed on the first paragraph of page 34 of WO2007/031091 (hereby incorporated by reference). It is, in some embodiments, other than the phosphodiester linkage(s) of region B (where present), it is preferred to modify the internucleotide linkage from its normal phosphodiester to one that is more resistant to nuclease attack, such as phosphorothioate or boranophosphate—these two, being cleavable by RNase H, also allow that route of antisense inhibition in reducing the expression of the target gene.

In some embodiments the oligomer of the present invention comprises one or more nucleoside linkages selected from the group consisting of phosphorothioate, phosphorodithioate and boranophosphate.

Suitable sulphur (S) containing internucleotide linkages as provided herein may be preferred, such as phosphorothioate or phosphodithionate. Phosphorothioate internucleotide linkages are also preferred, particularly for the first region, such as in gapmers, mixers, antimirs splice switching oligomers, and totalmers.

The term 'mixmer' refers to oligomers which comprise both naturally and non-naturally occurring nucleotides, where, as opposed to gapmers, tailmers, and headmers there is no contiguous sequence of more than 5, and in some embodiments no more than 4 consecutive, such as no more than three consecutive, naturally occurring nucleotides, such as DNA units The term "totalmer" refers to a single stranded oligomer which only comprises non-naturally occurring nucleosides, such as sugar-modified nucleoside analogues.

For gapmers, the internucleotide linkages in the oligomer may, for example be phosphorothioate or boranophosphate so as to allow RNase H cleavage of targeted RNA. Phosphorothioate is preferred, for improved nuclease resistance and other reasons, such as ease of manufacture.

In one aspect, with the exception of the phosphodiester linkage between the first and second region, and optionally within region B, the remaining internucleoside linkages of the oligomer of the invention, the nucleotides and/or nucleotide analogues are linked to each other by means of phosphorothioate groups. In some embodiments, at least 50%, such as at least 70%, such as at least 80%, such as at least 90% such as all the internucleoside linkages between nucleosides in the first region are other than phosphodiester (phosphate), such as are selected from the group consisting of phosphorothioate phosphorodithioate, or boranophosphate. In some embodiments, at least 50%, such as at least 70%, such as at least 80%, such as at least 90% such as all the internucleoside linkages between nucleosides in the first region are phosphorothioate.

WO09124238 refers to oligomeric compounds having at least one bicyclic nucleoside attached to the 3' or 5' termini by a neutral internucleoside linkage. The oligomers of the invention may therefore have at least one bicyclic nucleoside attached to the 3' or 5' termini by a neutral internucleoside linkage, such as one or more phosphotriester, methylphosphonate, MMI, amide-3, formacetal or thioformacetal. The remaining linkages may be phosphorothioate.

Oligomer Conjugates (Region C)

A further aspect of the invention is an antisense oligonucleotide conjugate comprising an oligomer of the invention, and at least one non-nucleotide or non-polynucleotide moiety (C) covalently attached to said oligomer (A), optionally via a linker region positioned between the contiguous sequence of the oligomer and the conjugate moiety (B and/or Y).

Representative conjugate moieties which have been used with oligonucleotides can include lipophilic molecules (aromatic and non-aromatic) including steroid molecules; proteins (e.g., antibodies, enzymes, serum proteins); peptides; vitamins (water-soluble or lipid-soluble); polymers (water-soluble or lipid-soluble); small molecules including drugs, toxins, reporter molecules, and receptor ligands; carbohydrate complexes; nucleic acid cleaving complexes; metal chelators (e.g., porphyrins, texaphyrins, crown ethers, etc.); intercalators including hybrid photonuclease/intercalators; crosslinking agents (e.g., photoactive, redox active), and combinations and derivatives thereof. Numerous suitable conjugate moieties, their preparation and linkage to oligomeric compounds are provided, for example, in WO 93/07883 and U.S. Pat. No. 6,395,492, each of which is incorporated herein by reference in its entirety. Oligonucleotide conjugates and their syntheses are also reported in comprehensive reviews by Manoharan in Antisense Drug Technology, Principles, Strategies, and Applications, S. T. Crooke, ed., Ch. 16, Marcel Dekker, Inc., 2001 and Manoharan, Antisense and Nucleic Acid Drug Development, 2002, 12, 103, each of which is incorporated herein by reference in its entirety.

In some embodiments the oligomer of the invention is targeted to the liver—i.e. after systemic administration the compound accumulates in the liver cells (such as hepatocytes). Targeting to the liver can be greatly enhanced by the addition of a conjugate moiety (C). However, in order to maximize the efficacy of the oligomer it is often desirable that the conjugate (or targeting moiety) is linked to the oligomer via a biocleavable linker (B), such as a nucleotide phosphate linker. It is therefore desirable to use a conjugate moiety which enhances uptake and activity in hepatocytes. The enhancement of activity may be due to enhanced uptake or it may be due to enhanced potency of the compound in hepatocytes.

In some embodiments, the oligomeric compound is a LNA oligomer, such as a gapmer, or for example an LNA antisense oligomer, (which may be referred to as region A herein) comprising an antisense oligomer, optionally a biocleavable linker, such as region B, and a carbohydrate conjugate (which may be referred to as region C). The LNA antisense oligomer may be 7-30, such as 8-26 nucleosides in length and it comprises at least one LNA unit (nucleoside).

In some embodiments, the conjugate is or may comprise a carbohydrate or comprises a carbohydrate group. In some embodiments, the carbohydrate is selected from the group consisting of galactose, lactose, n-acetylgalactosamine, mannose, and mannose-6-phosphate. In some embodiments, the conjugate group is or may comprise mannose or mannose-6-phosphate. Carbohydrate conjugates may be used to enhance delivery or activity in a range of tissues, such as liver and/or muscle. See, for example, EP1495769, WO99/65925, Yang et al., Bioconjug Chem (2009) 20(2): 213-21. Zatsepin & Oretskaya Chem Biodivers. (2004) 1(10): 1401-17.

In some embodiments the carbohydrate moiety is not a linear carbohydrate polymer. In some embodiments, the oligomeric compound is a LNA oligomer, for example an LNA antisense oligomer, (which may be referred to as region A herein) comprising an antisense oligomer, region B as defined herein, and an asialoglycoprotein receptor targeting moiety conjugate moiety, such as a GalNAc moiety (which may be referred to as region C). The carbohydrate moiety may be multi-valent, such as, for example 2, 3, 4 or 4 identical or non-identical carbohydrate moieties may be covalently joined to the oligomer, optionally via a linker or linkers (such as region Y).

GalNAc Conjugate Moieties

In some embodiments the carbohydrate moiety is not a linear carbohydrate polymer. The carbohydrate moiety may however be multi-valent, such as, for example 2, 3, 4 or 4 identical or non-identical carbohydrate moieties may be covalently joined to the oligomer, optionally via a linker or linkers. In some embodiments the invention provides a conjugate comprising the oligomer of the invention and a carbohydrate conjugate moiety. In some embodiments the invention provides a conjugate comprising the oligomer of the invention and an asialoglycoprotein receptor targeting moiety conjugate moiety, such as a GalNAc moiety, which may form part of a further region (referred to as region C).

The invention also provides LNA antisense oligonucleotides which are conjugated to an asialoglycoprotein receptor targeting moiety. In some embodiments, the conjugate moiety (such as the third region or region C) comprises an asialoglycoprotein receptor targeting moiety, such as galactose, galactosamine, N-formyl-galactosamine, N-acetylgalactosamine, N-propionyl-galactosamine, N-n-butanoyl-galactosamine, and N-isobutanoylgalactos-amine. In some embodiments the conjugate comprises a galactose cluster, such as N-acetylgalactosamine trimer. In some embodiments, the conjugate moiety comprises an GalNAc (N-acetylgalactosamine), such as a mono-valent, di-valent, tri-valent of tetra-valent GalNAc. Trivalent GalNAc conjugates may be used to target the compound to the liver. GalNAc conjugates have been used with methylphosphonate and PNA antisense oligonucleotides (e.g. U.S. Pat. No. 5,994,517 and Hangeland et al., Bioconjug Chem. 1995 November-December; 6(6):695-701) and siRNAs (e.g. WO2009/126933, WO2012/089352 & WO2012/083046). The GalNAc references and the specific conjugates used therein are hereby incorporated by reference. WO2012/083046 discloses siRNAs with GalNAc conjugate moieties which comprise cleavable pharmacokinetic modulators, which are suitable for use in the present invention, the preferred pharmacokinetic modulators are C16 hydrophobic groups such as palmitoyl, hexadec-8-enoyl, oleyl, (9E, 12E)-octadeca-9,12-dienoyl, dioctanoyl, and C16-C20 acyl. The '046 cleavable pharmacokinetic modulators may also be cholesterol.

The 'targeting moieties (conjugate moieties) may be selected from the group consisting of: galactose, galactosamine, N-formyl-galactosamine, N-acetylgalactosamine, N-propionyl-galactosamine, N-n-butanoyl-galactosamine, N-iso-butanoylgalactos-amine, galactose cluster, and N-acetylgalactosamine trimer and may have a pharmacokinetic modulator selected from the group consisting of: hydrophobic group having 16 or more carbon atoms, hydrophobic group having 16-20 carbon atoms, palmitoyl, hexadec-8-enoyl, oleyl, (9E,12E)-octadeca-9,12dienoyl, dioctanoyl, and C16-C20 acyl, and cholesterol. Certain GalNAc clusters disclosed in '046 include: (E)-hexadec-8-enoyl (C16), oleyl (C18), (9,E,12E)-octadeca-9,12-dienoyl (C18), octanoyl (C8), dodececanoyl (C12), C-20 acyl, C24 acyl, dioctanoyl (2×C8). The targeting moiety-pharmacokinetic modulator targeting moiety may be linked to the polynucleotide via a physiologically labile bond or, e.g. a disulfide bond, or a PEG linker. The invention also relates to the use of phospodiester linkers between the oligomer and the conjugate group (these are referred to as region B herein, and suitably are positioned between the LNA oligomer and the carbohydrate conjugate group).

For targeting hepatocytes in liver, a preferred targeting ligand is a galactose cluster.

A galactose cluster comprises a molecule having e.g. comprising two to four terminal galactose derivatives. As used herein, the term galactose derivative includes both galactose and derivatives of galactose having affinity for the asialoglycoprotein receptor equal to or greater than that of galactose. A terminal galactose derivative is attached to a molecule through its C—I carbon. The asialoglycoprotein receptor (ASGPr) is primarily expressed on hepatocytes and binds branched galactose-terminal glycoproteins. A preferred galactose cluster has three terminal galactosamines or galactosamine derivatives each having affinity for the asialoglycoprotein receptor. A more preferred galactose cluster has three terminal N-acetyl-galactosamines. Other terms common in the art include tri-antennary galactose, tri-valent galactose and galactose trimer. It is known that tri-antennary galactose derivative clusters are bound to the ASGPr with greater affinity than bi-antennary or mono-antennary galactose derivative structures (Baenziger and Fiete, 1980, Cell, 22, 611-620; Connolly et al., 1982, 1. Biol. Chem., 257, 939-945). Multivalency is required to achieve nM affinity. According to WO 2012/083046 the attachment of a single galactose derivative having affinity for the asialoglycoprotein receptor does not enable functional delivery of the RNAi polynucleotide to hepatocytes in vivo when co-administered with the delivery polymer.

A galactose cluster may comprise two or preferably three galactose derivatives each linked to a central branch point. The galactose derivatives are attached to the central branch point through the C—I carbons of the saccharides. The galactose derivative is preferably linked to the branch point via linkers or spacers. A preferred spacer is a flexible hydrophilic spacer (U.S. Pat. No. 5,885,968; Biessen et al. J. Med. Chern. 1995 Vol. 39 p. 1538-1546). A preferred flexible hydrophilic spacer is a PEG spacer. A preferred PEG spacer is a PEG3 spacer. The branch point can be any small molecule which permits attachment of the three galactose derivatives and further permits attachment of the branch point to the oligomer. An exemplary branch point group is a di-lysine. A di-lysine molecule contains three amine groups through which three galactose derivatives may be attached and a carboxyl reactive group through which the di lysine may be attached to the oligomer. Attachment of the branch point to oligomer may occur through a linker or spacer. A preferred spacer is a flexible hydrophilic spacer. A preferred flexible hydrophilic spacer is a PEG spacer. A preferred PEG spacer is a PEG3 spacer (three ethylene units). The galactose cluster may be attached to the 3' or 5' end of the oligomer using methods known in the art.

A preferred galactose derivative is an N-acetyl-galactosamine (GalNAc). Other saccharides having affinity for the asialoglycoprotein receptor may be selected from the list comprising: galactosamine, N-n-butanoylgalactosamine, and N-iso-butanoylgalactosamine. The affinities of numerous galactose derivatives for the asialoglycoprotein receptor have been studied (see for example: Jobst, S. T. and Drickamer, K. JB.C. 1996, 271, 6686) or are readily determined using methods typical in the art.

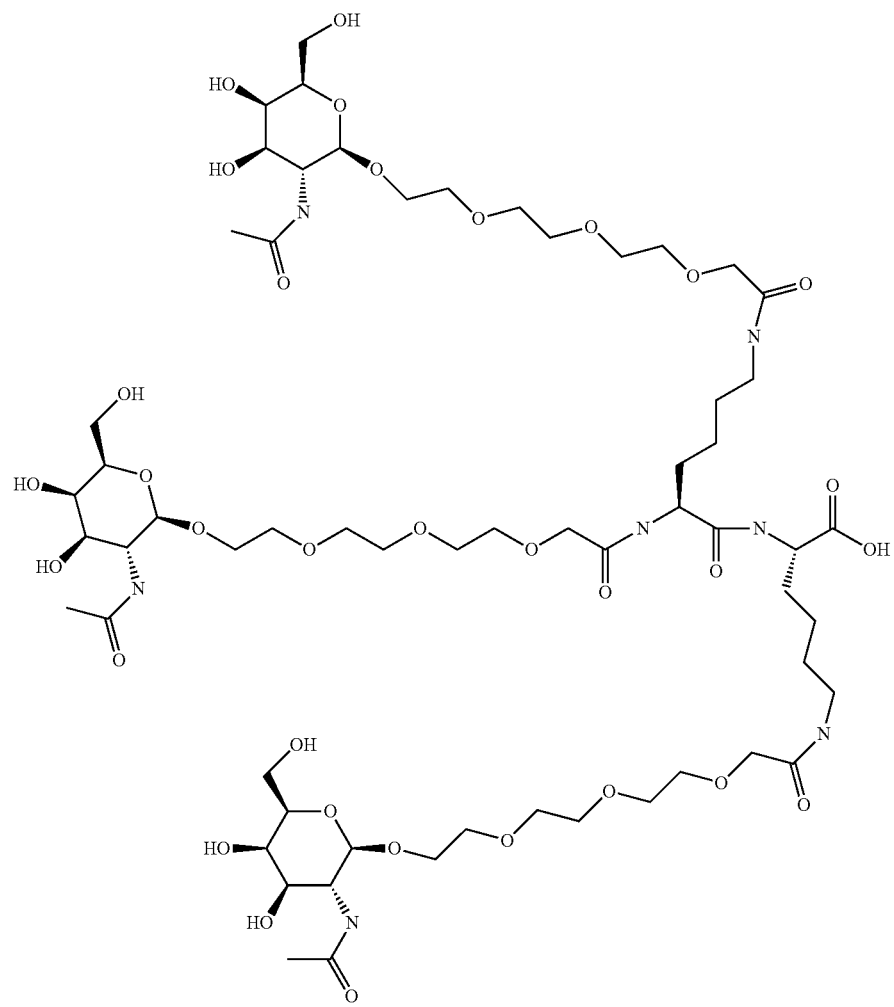 [SMILES: CC(=O)N[C@H]1[C@H](OCCOCCOCCOCC(=O)NCCCC[C@H](NC(=O)[C@H](CCCCNC(=O)COCCOCCOCCO[C@@H]2O[C@H](CO)[C@H](O)[C@H](O)[C@H]2NC(C)=O)NC(=O)COCCOCCOCCO[C@@H]2O[C@H](CO)[C@H](O)[C@H](O)[C@H]2NC(C)=O)C(=O)O)O[C@H](CO)[C@H](O)[C@@H]1O]

One embodiment of a Galactose cluster
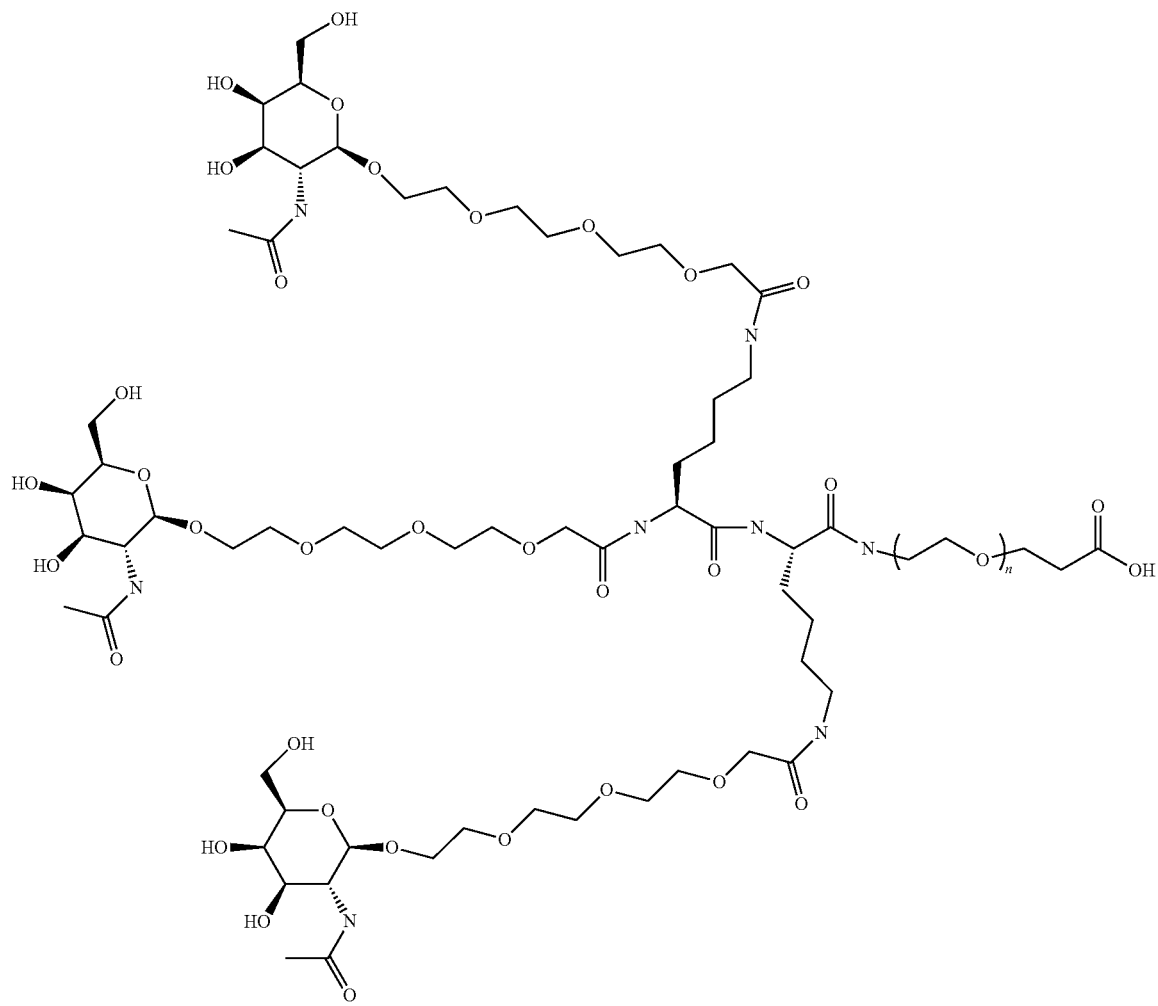
Galactose cluster with PEG spacer between branch point and nucleic acid
Further Examples of the conjugate of the invention are illustrated below:
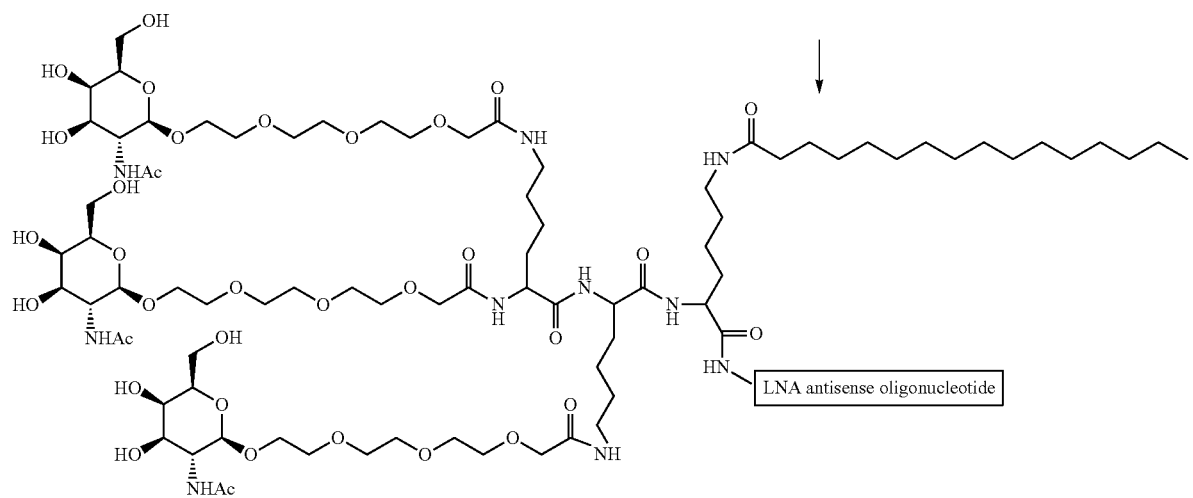

-continued
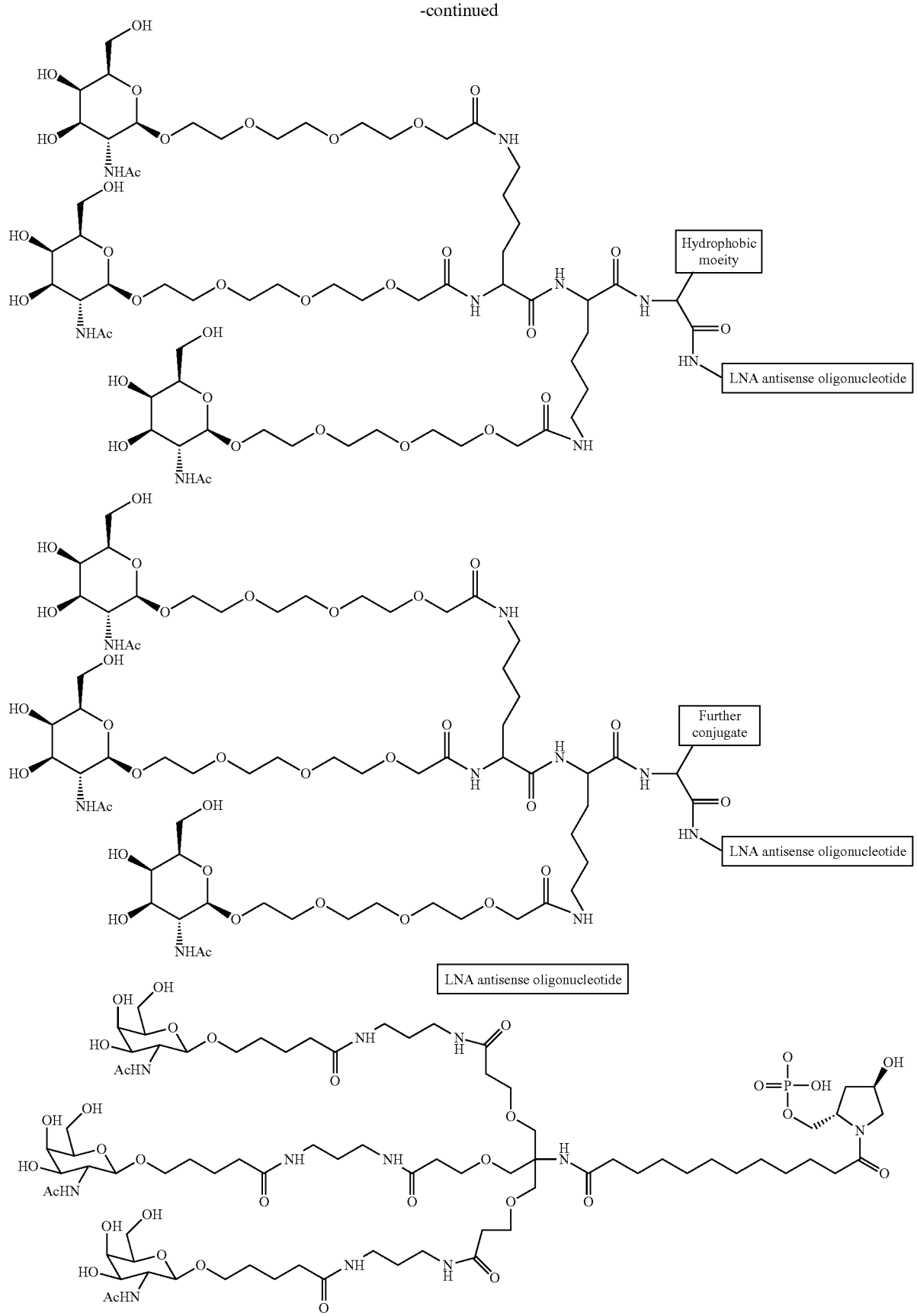

Where at the hydrophobic or lipophilic (or further conjugate) moiety (i.e. pharmacokinetic modulator) in the above GalNAc cluster conjugates is, when using LNA oligomers, such as LNA antisense oligonucleotides, optional.

See the figures for specific GalNAc clusters used in the present study, Conj 1, 2, 3, 4 and Conj1a, 2a, 3a and 4a (which are shown with an optional C6 linker which joins the GalNAc cluster to the oligomer).

In a preferred embodiment of the invention the conjugate moiety of the antisense oligonucleotide conjugate comprises or consists of Conj 1, 2, 3, 4 and Conj1a, 2a, 3a and 4a. Most preferably the conjugate moiety comprises or consists of Conj 2a.

In another preferred embodiment the antisense oligonucleotide conjugate is selected from the group consisting of SEQ ID NO 17, 18, 19, 20, 21, 22, 23, and 24.

Each carbohydrate moiety of a GalNAc cluster (e.g. GalNAc) may therefore be joined to the oligomer via a spacer, such as (poly)ethylene glycol linker (PEG), such as a di, tri, tetra, penta, hexa-ethylene glycol linker. As is shown above the PEG moiety forms a spacer between the galctose sugar moiety and a peptide (trilysine is shown) linker.

In some embodiments, the GalNAc cluster comprises a peptide linker, e.g. a Tyr-Asp(Asp) tripeptide or Asp(Asp) dipeptide, which is attached to the oligomer (or to region Y or region B) via a biradical linker, for example the GalNAc cluster may comprise the following biradical linkers:

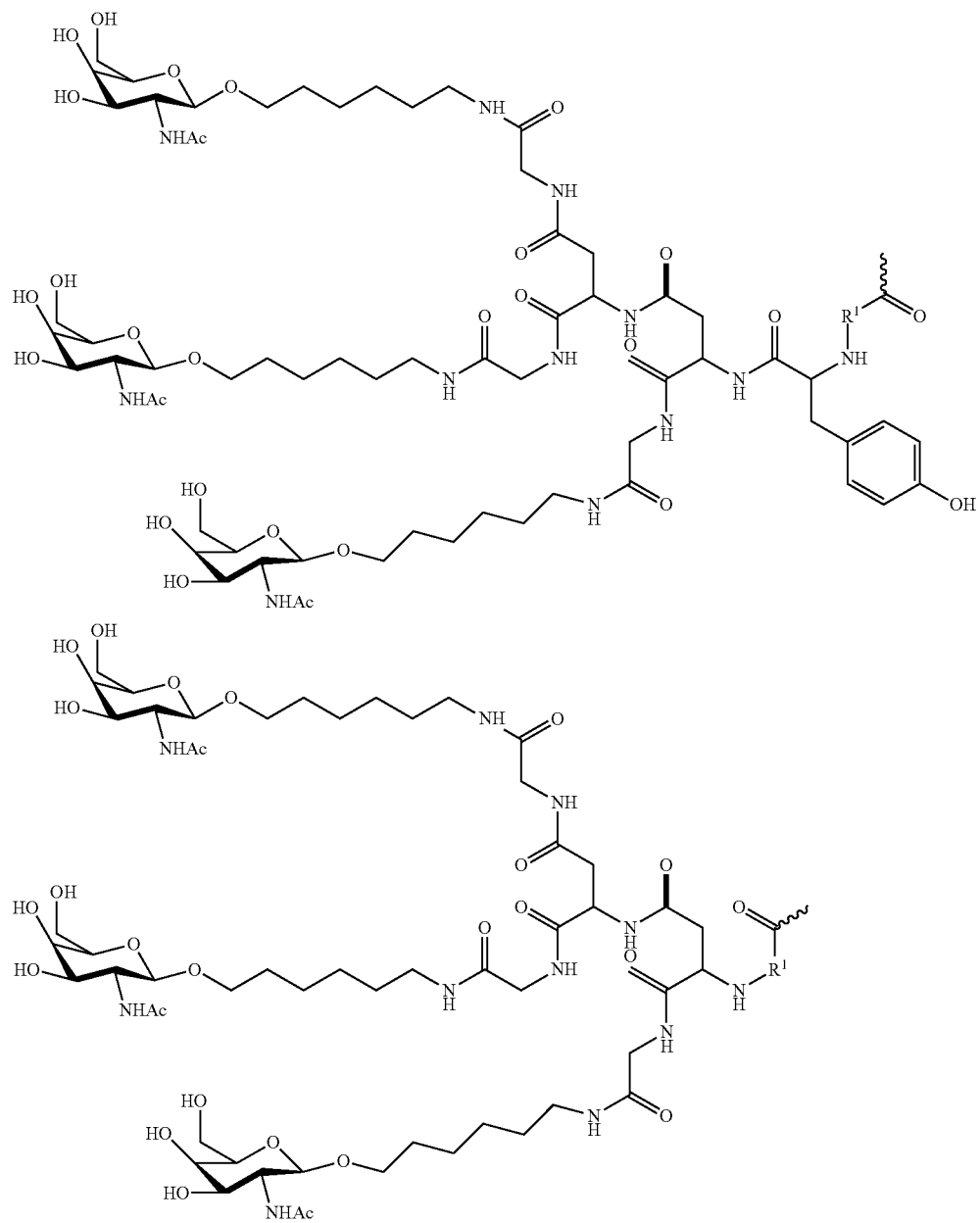

$R^1$ is a biradical preferably selected from —$C_2H_4$—, —$C_3H_6$—, —$C_4H_8$—, —$C_5H_{10}$—, —$C_6H_{12}$—, 1,4-cyclohexyl (—C6H10-), 1,4-phenyl (—$C_6H_4$—), —$C_2H_4OC_2H_4$—, —$C_2H_4(OC_2H_4)_2$— or —$C_2H_4(OC_2H_4)_3$—, $C(O)CH_2$—, —$C(O)C_2H_4$—, —$C(O)C_3H_6$—, —$C(O)C_4H_8$—, —$C(O)C_5H_{10}$—, —$C(O)C_6H_{12}$—, 1,4-cyclohexyl (—$C(O)C_6H_{10}$—), 1,4-phenyl (—$C(O)C_6H_4$—), —$C(O)C_2H_4OC_2H_4$—, —$C(O)C_2H_4(OC_2H_4)_2$— or —$C(O)C_2H_4(OC_2H_4)_3$—.

In some embodiments, $R^1$ is a biradical preferably selected from —$C_2H_4$—, —$C_3H_6$—, —$C_4H_8$—, —$C_5H_{10}$—, —$C_6H_{12}$—, 1,4-cyclohexyl (—C6H10-), 1,4-phenyl (—$C_6H_4$—), —$C_2H_4OC_2H_4$—, —$C_2H_4(OC_2H_4)_2$— or —$C_2H_4(OC_2H_4)_3$—.

The carbohydrate conjugate(e.g. GalNAc), or carbohydrate-linker moiety (e.g. carbohydrate-PEG moiety) may be covalently joined (linked) to the oligomer via a branch point group such as, an amino acid, or peptide, which suitably comprises two or more amino groups (such as 3, 4, or 5), such as lysine, di-lysine or tri-lysine or tetra-lysine. A tri-lysine molecule contains four amine groups through which three carbohydrate conjugate groups, such as galactose & derivatives (e.g. GalNAc) and a further conjugate such as a hydrophobic or lipophilic moiety/group may be attached and a carboxyl reactive group through which the tri-lysine may be attached to the oligomer. The further conjugate, such as lipophilic/hyrodphobic moiety may be attached to the lysine residue that is attached to the oligomer.

Surprisingly, the present inventors have found that GalNAc conjugates for use with LNA oligomers do not require a pharmacokinetic modulator (as described below), and as such, in some embodiments, the GalNAc conjugate is not covalently linked to a lipophilic or hydrophobic moiety, such as those described here in, e.g. do not comprise a C8-C36 fatty acid or a sterol. The invention therefore also provides for LNA oligomer GalNAc conjugates which do not comprise a lipophilic or hydrophobic pharmacokinetic modulator or conjugate moiety/group.

Pharmacokinetic Modulators

The compound of the invention may further comprise one or more additional conjugate moieties, of which lipophilic or hydrophobic moieties are particularly interesting, such as when the conjugate group is a carbohydrate moiety. Such lipophilic or hydrophobic moieties may act as pharmacokinetic modulators, and may be covalently linked to either the carbohydrate conjugate, a linker linking the carbohydrate conjugate to the oligomer or a linker linking multiple carbohydrate conjugates (multi-valent) conjugates, or to the oligomer, optionally via a linker, such as a bio cleavable linker.

The oligomer or conjugate moiety may therefore comprise a pharmacokinetic modulator, such as a lipophilic or hydrophobic moieties. Such moieties are disclosed within the context of siRNA conjugates in WO2012/082046. The hydrophobic moiety may comprise a C8-C36 fatty acid, which may be saturated or un-saturated. In some embodiments, C10, C12, C14, C16, C18, C20, C22, C24, C26, C28, C30, C32 and C34 fatty acids may be used. The hydrophobic group may have 16 or more carbon atoms. Exemplary suitable hydrophobic groups may be selected from the group comprising: sterol, cholesterol, palmitoyl, hexadec-8-enoyl, oleyl, (9E, 12E)-octadeca-9,12-dienoyl, dioctanoyl, and C16-C20 acyl. According to WO'346, hydrophobic groups having fewer than 16 carbon atoms are less effective in enhancing polynucleotide targeting, but they may be used in multiple copies (e.g. 2×, such as 2×C8 or C10, C12 or C14) to enhance efficacy. Pharmacokinetic modulators useful as polynucleotide targeting moieties may be selected from the group consisting of: cholesterol, alkyl group, alkenyl group, alkynyl group, aryl group, aralkyl group, aralkenyl group, and aralkynyl group, each of which may be linear, branched, or cyclic. Pharmacokinetic modulators are preferably hydrocarbons, containing only carbon and hydrogen atoms. However, substitutions or heteroatoms which maintain hydrophobicity, for example fluorine, may be permitted.

Lipophilic Conjugates

In some embodiments, the conjugate group is or may comprise a lipophilic moiety, such as a sterol (for example, cholesterol, cholesteryl, cholestanol, stigmasterol, cholanic acid and ergosterol). In some embodiments the conjugate is or comprises tocopherol (exemplified as Conj 6 and Conj 6a in FIG. 2). In some embodiments, the conjugate is or may comprise cholesterol (exemplified as Conj 5 and Conj 5a in FIG. 2).

In some embodiments, the conjugate is, or may comprise a lipid, a phospholipid or a lipophilic alcohol, such as a cationic lipid, a neutral lipid, sphingolipid, and fatty acid such as stearic, oleic, elaidic, linoleic, linoleaidic, linolenic, and myristic acid. In some embodiments the fatty acid comprises a C4-C30 saturated or unsaturated alkyl chain. The alkyl chain may be linear or branched.

Lipophilic conjugate moieties can be used, for example, to counter the hydrophilic nature of an oligomeric compound and enhance cellular penetration.

Lipophilic moieties include, for example, sterols stanols, and steroids and related compounds such as cholesterol (U.S. Pat. No. 4,958,013 and Letsinger et al., Proc. Natl. Acad. Sci. USA, 1989, 86, 6553), thiocholesterol (Oberhauser et al, Nucl Acids Res., 1992, 20, 533), lanosterol, coprostanol, stigmasterol, ergosterol, calciferol, cholic acid, deoxycholic acid, estrone, estradiol, estratriol, progesterone, stilbestrol, testosterone, androsterone, deoxycorticosterone, cortisone, 17-hydroxycorticosterone, their derivatives, and the like. In some embodiments, the conjugate may be selected from the group consisting of cholesterol, thiocholesterol, lanosterol, coprostanol, stigmasterol, ergosterol, calciferol, cholic acid, deoxycholic acid, estrone, estradiol, estratriol, progesterone, stilbestrol, testosterone, androsterone, deoxycorticosterone, cortisone, and 17-hydroxycorticosterone. Other lipophilic conjugate moieties include aliphatic groups, such as, for example, straight chain, branched, and cyclic alkyls, alkenyls, and alkynyls. The aliphatic groups can have, for example, 5 to about 50, 6 to about 50, 8 to about 50, or 10 to about 50 carbon atoms. Example aliphatic groups include undecyl, dodecyl, hexadecyl, heptadecyl, octadecyl, nonadecyl, terpenes, bornyl, adamantyl, derivatives thereof and the like. In some embodiments, one or more carbon atoms in the aliphatic group can be replaced by a heteroatom such as O, S, or N (e.g., geranyloxyhexyl). Further suitable lipophilic conjugate moieties include aliphatic derivatives of glycerols such as alkylglycerols, bis(alkyl)glycerols, tris(alkyl)glycerols, monoglycerides, diglycerides, and triglycerides. In some embodiments, the lipophilic conjugate is di-hexyldecyl-rac-glycerol or 1,2-di-O-hexyldecyl-rac-glycerol (Manoharan et al., Tetrahedron Lett., 1995, 36, 3651; Shea, et al., Nuc. Acids Res., 1990, 18, 3777) or phosphonates thereof. Saturated and unsaturated fatty functionalities, such as, for example, fatty acids, fatty alcohols, fatty esters, and fatty amines, can also serve as lipophilic conjugate moieties. In some embodiments, the fatty functionalities can contain from about 6 carbons to about 30 or about 8 to about 22 carbons. Example fatty acids include, capric, caprylic, lauric, palmitic, myristic, stearic, oleic, linoleic, linolenic, arachidonic, eicosenoic acids and the like.

In further embodiments, lipophilic conjugate groups can be polycyclic aromatic groups having from 6 to about 50, 10 to about 50, or 14 to about 40 carbon atoms. Example polycyclic aromatic groups include pyrenes, purines, acridines, xanthenes, fluorenes, phenanthrenes, anthracenes, quinolines, isoquinolines, naphthalenes, derivatives thereof and the like. Other suitable lipophilic conjugate moieties include menthols, trityls (e.g., dimethoxytrityl (DMT)), phenoxazines, lipoic acid, phospholipids, ethers, thioethers (e.g., hexyl-S-tritylthiol), derivatives thereof and the like. Preparation of lipophilic conjugates of oligomeric compounds are well-described in the art, such as in, for example, Saison-Behmoaras et al, EMBO J., 1991, 10, 1111; Kabanov et al., FEBSLett., 1990, 259, 327; Svinarchuk et al, Biochimie, 1993, 75, 49; (Mishra et al., Biochim. Biophys. Acta, 1995, 1264, 229, and Manoharan et al., Tetrahedron Lett., 1995, 36, 3651.

Oligomeric compounds containing conjugate moieties with affinity for low density lipoprotein (LDL) can help provide an effective targeted delivery system. High expression levels of receptors for LDL on tumor cells makes LDL an attractive carrier for selective delivery of drugs to these cells (Rump, et al., Bioconjugate Chem., 1998, 9, 341; Firestone, Bioconjugate Chem., 1994, 5, 105; Mishra, et al., Biochim. Biophys. Acta, 1995, 1264, 229). Moieties having affinity for LDL include many lipophilic groups such as steroids (e.g., cholesterol), fatty acids, derivatives thereof and combinations thereof. In some embodiments, conjugate moieties having LDL affinity can be dioleyl esters of cholic acids such as chenodeoxycholic acid and lithocholic acid.

In some embodiments, the lipophilic conjugates may be or may comprise biotin. In some embodiments, the lipophilic conjugate may be or may comprise a glyceride or glyceride ester.

Lipophillic conjugates, such as sterols, stanols, and stains, such as cholesterol or as disclosed herein, may be used to enhance delivery of the oligonucleotide to, for example, the liver (typically hepatocytes).

In a preferred embodiment of the invention the conjugate moiety of the antisense oligonucleotide conjugate comprises or consists of Conj 5, 5a, 6 or 6a. Most preferably the conjugate moiety comprises or consists of Conj 5a.

In another preferred embodiment the antisense oligonucleotide conjugate is selected from the group consisting of SEQ ID NO 9, 10, 11, 12, 13, 14, 15, 16, 41, 42 and 43.

The following references also refer to the use of lipophilic conjugates: Kobylanska et al., Acta Biochim Pol. (1999); 46(3): 679-91. Felber et al., Biomaterials (2012) 33(25): 599-65); Grijalvo et al., J Org Chem (2010) 75(20): 6806-13. Koufaki et al., Curr Med Chem (2009) 16(35): 4728-42. Godeau et al J. Med. Chem. (2008) 51(15): 4374-6.

Linkers (e.g. Region B or Y)

A linkage or linker is a connection between two atoms that links one chemical group or segment of interest to another chemical group or segment of interest via one or more covalent bonds. Conjugate moieties (or targeting or blocking moieties) can be attached to the oligomeric compound directly or through a linking moiety (linker or tether)—a linker. Linkers are bifunctional moieties that serve to covalently connect a third region, e.g. a conjugate moiety, to an oligomeric compound (such as to region A). In some embodiments, the linker comprises a chain structure or an oligomer of repeating units such as ethylene glyol or amino acid units. The linker can have at least two functionalities, one for attaching to the oligomeric compound and the other for attaching to the conjugate moiety. Example linker functionalities can be electrophilic for reacting with nucleophilic groups on the oligomer or conjugate moiety, or nucleophilic for reacting with electrophilic groups. In some embodiments, linker functionalities include amino, hydroxyl, carboxylic acid, thiol, phosphoramidate, phosphorothioate, phosphate, phosphite, unsaturations (e.g., double or triple bonds), and the like. Some example linkers include 8-amino-3,6-dioxaoctanoic acid (ADO), succinimidyl 4-(N-maleimidomethyl)cyclohexane-1-carboxylate (SMCC), 6-aminohexanoic acid (AHEX or AHA), 6-aminohexyloxy, 4-aminobutyric acid, 4-aminocyclohexylcarboxylic acid, succinimidyl 4-(N-maleimidomethyl)cyclohexane-1-carboxy-(6-amido-caproate) (LCSMCC), succinimidyl m-maleimido-benzoylate (MBS), succinimidyl N-e-maleimidocaproylate (EMCS), succinimidyl 6-(beta-maleimidopropionamido) hexanoate (SMPH), succinimidyl N-(a-maleimido acetate) (AMAS), succinimidyl 4-(p-maleimidophenyl)butyrate (SMPB), beta-alanine (beta-ALA), phenylglycine (PHG), 4-aminocyclohexanoic acid (ACHC), beta-(cyclopropyl) alanine (beta-CYPR), amino dodecanoic acid (ADC), alylene diols, polyethylene glycols, amino acids, and the like.

A wide variety of further linker groups are known in the art that can be useful in the attachment of conjugate moieties to oligomeric compounds. A review of many of the useful linker groups can be found in, for example, Antisense Research and Applications, S. T. Crooke and B. Lebleu, Eds., CRC Press, Boca Raton, Fla., 1993, p. 303-350. A disulfide linkage has been used to link the 3' terminus of an oligonucleotide to a peptide (Corey, et al., Science 1987, 238, 1401; Zuckermann, et al, J Am. Chem. Soc. 1988, 110, 1614; and Corey, et al., J Am. Chem. Soc. 1989, 111, 8524). Nelson, et al., Nuc. Acids Res. 1989, 17, 7187 describe a linking reagent for attaching biotin to the 3'-terminus of an oligonucleotide. This reagent, N-Fmoc-O-DMT-3-amino-1, 2-propanediol is commercially available from Clontech Laboratories (Palo Alto, Calif.) under the name 3'-Amine. It is also commercially available under the name 3'-Amino-Modifier reagent from Glen Research Corporation (Sterling, Va.). This reagent was also utilized to link a peptide to an oligonucleotide as reported by Judy, et al., Tetrahedron Letters 1991, 32, 879. A similar commercial reagent for linking to the 5'-terminus of an oligonucleotide is 5'-Amino-Modifier C6. These reagents are available from Glen Research Corporation (Sterling, Va.). These compounds or similar ones were utilized by Krieg, et al, Antisense Research and Development 1991, 1, 161 to link fluorescein to the 5'-terminus of an oligonucleotide. Other compounds such as acridine have been attached to the 3'-terminal phosphate group of an oligonucleotide via a polymethylene linkage (Asseline, et al., Proc. Natl. Acad. Sci. USA 1984, 81, 3297). [0074] Any of the above groups can be used as a single linker or in combination with one or more further linkers.

Linkers and their use in preparation of conjugates of oligomeric compounds are provided throughout the art such as in WO 96/11205 and WO 98/52614 and U.S. Pat. Nos. 4,948,882; 5,525,465; 5,541,313; 5,545,730; 5,552,538; 5,580,731; 5,486,603; 5,608,046; 4,587,044; 4,667,025; 5,254,469; 5,245,022; 5,112,963; 5,391,723; 5,510,475; 5,512,667; 5,574,142; 5,684,142; 5,770,716; 6,096,875; 6,335,432; and 6,335,437, Wo2012/083046 each of which is incorporated by reference in its entirety.

As used herein, a physiologically labile bond is a labile bond that is cleavable under conditions normally encountered or analogous to those encountered within a mammalian body (also referred to as a cleavable linker, illustrated as region B in FIGS. 12 and 13). Physiologically labile linkage groups are selected such that they undergo a chemical transformation (e.g., cleavage) when present in certain physiological conditions. Mammalian intracellular conditions include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic or hydrolytic enzymes. In some embodiments, the cleavable linker is susceptible to nuclease(s) which may for example, be expressed in the target cell—and as such, as detailed herein, the linker may be a short region (e.g. 1-10) phosphodiester linked nucleosides, such as DNA nucleosides.

Chemical transformation (cleavage of the labile bond) may be initiated by the addition of a pharmaceutically acceptable agent to the cell or may occur spontaneously when a molecule containing the labile bond reaches an appropriate intra- and/or extra-cellular environment. For example, a pH labile bond may be cleaved when the molecule enters an acidified endosome. Thus, a pH labile bond may be considered to be an endosomal cleavable bond. Enzyme cleavable bonds may be cleaved when exposed to enzymes such as those present in an endosome or lysosome or in the cytoplasm. A disulfide bond may be cleaved when the molecule enters the more reducing environment of the cell cytoplasm. Thus, a disulfide may be considered to be a cytoplasmic cleavable bond. As used herein, a pH-labile bond is a labile bond that is selectively broken under acidic conditions (pH<7). Such bonds may also be termed endosomally labile bonds, since cell endosomes and lysosomes have a pH less than 7.

Oligomer Linked Biocleavable Conjugates

The oligomeric compound may optionally, comprise a second region (region B) which is positioned between the oligomer (referred to as region A) and the conjugate (referred to as region C) See FIGS. 12 and 13 for illustrations). Region B may be a linker such as a cleavable linker (also referred to as a physiologically labile linkage). Nuclease Susceptible Physiological Labile Linkages: In some embodiments, the oligomer (also referred to as oligomeric compound) of the invention (or conjugate) comprises three regions:

i) a first region (region A), which comprises 10-18 contiguous nucleotides;

ii) a second region (region B) which comprises a biocleavable linker iii) a third region (C) which comprises a conjugate moiety, a targeting moiety, an activation moiety, wherein the third region is covalent linked to the second region.

In some embodiments, region B may be a phosphate nucleotide linker. For example such linkers may be used when the conjugate is a lipophilic conjugate, such as a lipid, a fatty acid, sterol, such as cholesterol or tocopherol. Phosphate nucleotide linkers may also be used for other conjugates, for example carbohydrate conjugates, such as GalNAc.

Peptide Linkers

In some embodiments, the biocleable linker (region B) is a peptide, such as a trilysine peptide linker which may be used in a polyGalNAc conjugate, such a a triGalNAc conjugate.

See also the peptide biradicals mentioned herein.

Other linkers known in the art which may be used, include disulfide linkers.

Phosphate Nucleotide Linkers

In some embodiments, region B comprises between 1-6 nucleotides, which is covalently linked to the 5' or 3' nucleotide of the first region, such as via a internucleoside linkage group such as a phosphodiester linkage, wherein either a. the internucleoside linkage between the first and second region is a phosphodiester linkage and the nucleoside of the second region [such as immediately] adjacent to the first region is either DNA or RNA; and/or b. at least 1 nucleoside of the second region is a phosphodiester linked DNA or RNA nucleoside;

In some embodiments, region A and region B form a single contiguous nucleotide sequence of 12-22 nucleotides in length.

In some aspects the internucleoside linkage between the first and second regions may be considered part of the second region.

In some embodiments, there is a phosphorus containing linkage group between the second and third region. The phosphorus linkage group, may, for example, be a phosphate (phosphodiester), a phosphorothioate, a phosphorodithioate or a boranophosphate group. In some embodiments, this phosphorus containing linkage group is positioned between the second region and a linker region which is attached to the third region. In some embodiments, the phosphate group is a phosphodiester.

Therefore, in some aspects the oligomeric compound comprises at least two phosphodiester groups, wherein at least one is as according to the above statement of invention, and the other is positioned between the second and third regions, optionally between a linker group and the second region.

In some embodiments, the third region is an activation group, such as an activation group for use in conjugation. In this respect, the invention also provides activated oligomers comprising region A and B and a activation group, e.g an intermediate which is suitable for subsequent linking to the third region, such as suitable for conjugation.

In some embodiments, the third region is a reactive group, such as a reactive group for use in conjugation. In this respect, the invention also provides oligomers comprising region A and B and a reactive group, e.g an intermediate which is suitable for subsequent linking to the third region, such as suitable for conjugation. The reactive group may, in some embodiments comprise an amine of alcohol group, such as an amine group.

In some embodiments region A comprises at least one, such as 2, 3, 4, 5, 6, 7, 8, 9, 10, 11, 12, 13, 14, 15, 16, 17, 18, 19, 20, or 21 internucleoside linkages other than phosphodiester, such as internucleoside linkages which are (optionally independently] selected from the group consisting of phosphorothioate, phosphorodithioate, and boranophosphate, and methylphosphonate, such as phosphorothioate. In some embodiments region A comprises at least one phosphorothioate linkage. In some embodiments at least 50%, such as at least 75%, such as at least 90% of the internucleoside linkages, such as all the internucleoside linkages within region A are other than phosphodiester, for example are phosphorothioate linkages. In some embodiments, all the internucleoside linkages in region A are other than phosphodiester.

In some embodiments, the oligomeric compound comprises an antisense oligonucleotide, such as an antisense oligonucleotide conjugate. The antisense oligonucleotide may be or may comprise the first region, and optionally the second region. In this respect, in some embodiments, region B may form part of a contiguous nucleobase sequence which is complementary to the (nucleic acid) target. In other embodiments, region B may lack complementarity to the target.

Alternatively stated, in some embodiments, the invention provides a non-phosphodieser linked, such as a phosphorothioate linked, oligonucleotide (e.g. an antisense oligonucleotide) which has at least one terminal (5' and/or 3') DNA or RNA nucleoside linked to the adjacent nucleoside of the oligonucleotide via a phosphodiester linkage, wherein the terminal DNA or RNA nucleoside is further covalently linked to a conjugate moiety, a targeting moiety or a blocking moiety, optionally via a linker moiety.

In some embodiments, the oligomeric compound comprises an antisense oligonucleotide, such as an antisense oligonucleotide conjugate. The antisense oligonucleotide may be or may comprise the first region, and optionally the second region. In this respect, in some embodiments, region B may form part of a contiguous nucleobase sequence which is complementary to the (nucleic acid) target. In other embodiments, region B may lack complementarity to the target.

In some embodiments, at least two consecutive nucleosides of the second region are DNA nucleosides (such as at least 3 or 4 or 5 consecutive DNA nucleotides).

In such an embodiment, the oligonucleotide of the invention may be described according to the following formula:

5'-A-PO-B[Y)X-3' or 3'-A-PO-B[Y)X-5' wherein A is region A, PO is a phosphodiester linkage, B is region B, Y is an optional linkage group, and X is a conjugate, a targeting, a blocking group or a reactive or activation group.

In some embodiments, region B comprises 3'-5' or 5'-3': i) a phosphodiester linkage to the 5' or 3' nucleoside of region A, ii) a DNA or RNA nucleoside, such as a DNA nucleoside, and iii) a further phosphodiester linkage 5'-A-PO-B-PO-3' or 3'-A-PO-B-PO-5'

The further phosphodiester linkage link the region B nucleoside with one or more further nucleoside, such as one or more DNA or RNA nucleosides, or may link to X (is a conjugate, a targeting or a blocking group or a reactive or activation group) optionally via a linkage group (Y).

In some embodiments, region B comprises 3'-5' or 5'-3': i) a phosphodiester linkage to the 5' or 3' nucleoside of region A, ii) between 2-10 DNA or RNA phosphodiester linked nucleosides, such as a DNA nucleoside, and optionally iii) a further phosphodiester linkage:

5'-A-[PO-B]n-[Y]-X 3' or 3'-A-[PO-B]n-[Y]-X 5'

5'-A-[PO-B]n-PO-[Y]-X 3' or 3'-A-[PO-B]n-PO-[Y]-X 5'

Wherein A represent region A, [PO-B]n represents region B, wherein n is 1-10, such as 1, 2, 3, 4, 5, 6, 7, 8, 9 or 10, PO is an optional phosphodiester linkage group between region B and X (or Y if present).

In some embodiments the invention provides compounds according to (or comprising) one of the following formula:

5' [Region A]-PO-[region B] 3'-Y-X

5' [Region A]-PO-[region B]-PO 3'-Y-X

5' [Region A]-PO-[region B] 3'-X

5' [Region A]-PO-[region B]-PO 3'-X

3' [Region A]-PO-[region B] 5'-Y-X

3' [Region A]-PO-[region B]-PO 5'-Y-X

3' [Region A]-PO-[region B] 5'-X

3' [Region A]-PO-[region B]-PO 5'-X

Region B, may for example comprise or consist of:

5' DNA3'

3' DNA 5'

5' DNA-PO-DNA-3'

3' DNA-PO-DNA-5'

5' DNA-PO-DNA-PO-DNA 3'

3' DNA-PO-DNA-PO-DNA 5'

5' DNA-PO-DNA-PO-DNA-PO-DNA 3'

3' DNA-PO-DNA-PO-DNA-PO-DNA 5'

5' DNA-PO-DNA-PO-DNA-PO-DNA-PO-DNA 3'

3' DNA-PO-DNA-PO-DNA-PO-DNA-PO-DNA 5'

It should be recognized that phosphate linked biocleavable linkers may employ nucleosides other than DNA and RNA. Biocleavable nucleotide linkers can be identified using the assays in example 6.

In some embodiments, the compound of the invention comprises a biocleavable linker (also referred to as the physiologically labile linker, Nuclease Susceptible Physiological Labile Linkages, or nuclease susceptible linker), for example the phosphate nucleotide linker (such as region B) or a peptide linker, which joins the oligomer (or contiguous nucleotide sequence or region A), to a conjugate moiety (or region C).

The susceptibility to cleavage in the assays shown in Example 6 can be used to determine whether a linker is biocleavable or physiologically labile.

Biocleavable linkers according to the present invention refers to linkers which are susceptible to cleavage in a target tissue (i.e. physiologically labile), for example liver and/or kidney. It is preferred that the cleavage rate seen in the target tissue is greater than that found in blood serum. Suitable methods for determining the level (%) of cleavage in tissue (e.g. liver or kidney) and in serum are found in example 6. In some embodiments, the biocleavable linker (also referred to as the physiologically labile linker, or nuclease susceptible linker), such as region B, in a compound of the invention, are at least about 20% cleaved, such as at least about 30% cleaved, such as at least about 40% cleaved, such as at least about 50% cleaved, such as at least about 60% cleaved, such as at least about 70% cleaved, such as at least about 75% cleaved, in the liver or kidney homogenate assay of Example 6. In some embodiments, the cleavage (%) in serum, as used in the assay in Example 6, is less than about 30%, is less than about 20%, such as less than about 10%, such as less than 5%, such as less than about 1%.

In some embodiments, which may be the same of different, the biocleavable linker (also referred to as the physiologically labile linker, or nuclease susceptible linker), such as region B, in a compound of the invention, are susceptible to S1 nuclease cleavage. Susceptibility to S1 cleavage may be evaluated using the S1 nuclease assay shown in Example 6. In some embodiments, the biocleavable linker (also referred to as the physiologically labile linker, or nuclease susceptible linker), such as region B, in a compound of the invention, are at least about 30% cleaved, such as at least about 40% cleaved, such as at least about 50% cleaved, such as at least about 60% cleaved, such as at least about 70% cleaved, such as at least about 80% cleaved, such as at least about 90% cleaved, such as at least 95% cleaved after 120 min incubation with S1 nuclease according to the assay used in Example 6.

Sequence Selection in the Second Region:

In some embodiments, region B does not form a complementary sequence when the oligonucleotide region A and B is aligned to the complementary target sequence.

In some embodiments, region B does form a complementary sequence when the oligonucleotide region A and B is aligned to the complementary target sequence. In this respect region A and B together may form a single contiguous sequence which is complementary to the target sequence.

In some embodiments, the sequence of bases in region B is selected to provide an optimal endonuclease cleavage site, based upon the predominant endonuclease cleavage enzymes present in the target tissue or cell or sub-cellular compartment. In this respect, by isolating cell extracts from target tissues and non-target tissues, endonuclease cleavage sequences for use in region B may be selected based upon a preferential cleavage activity in the desired target cell (e.g. liver/hepatocytes) as compared to a non-target cell (e.g. kidney). In this respect, the potency of the compound for target down-regulation may be optimized for the desired tissue/cell.

In some embodiments region B comprises a dinucleotide of sequence AA, AT, AC, AG, TA, TT, TC, TG, CA, CT, CC, CG, GA, GT, GC, or GG, wherein C may be 5-methylcytosine, and/or T may be replaced with U. In some embodiments region B comprises a trinucleotide of sequence AAA, AAT, AAC, AAG, ATA, ATT, ATC, ATG, ACA, ACT, ACC, ACG, AGA, AGT, AGC, AGG, TAA, TAT, TAC, TAG, TTA, TTT, TTC, TAG, TCA, TCT, TCC, TCG, TGA, TGT, TGC, TGG, CAA, CAT, CAC, CAG, CTA, CTG, CTC, CTT, CCA, CCT, CCC, CCG, CGA, CGT, CGC, CGG, GAA, GAT, GAC, CAG, GTA, GTT, GTC, GTG, GCA, GCT, GCC, GCG, GGA, GGT, GGC, and GGG wherein C may be 5-methylcytosine and/or T may be replaced with U. In some embodiments region B comprises a trinucleotide of sequence AAAX, AATX, AACX, AAGX, ATAX, ATTX, ATCX, ATGX, ACAX, ACTX, ACCX, ACGX, AGAX, AGTX, AGCX, AGGX, TAAX, TATX, TACX, TAGX, TTAX, TTTX, TTCX, TAGX, TCAX, TCTX, TCCX, TCGX, TGAX, TGTX, TGCX, TGGX, CAAX, CATX, CACX, CAGX, CTAX, CTGX, CTCX, CTTX, CCAX, CCTX, CCCX, CCGX, CGAX, CGTX, CGCX, CGGX, GAAX, GATX, GACX, CAGX, GTAX, GTTX, GTCX, GTGX, GCAX, GCTX, GCCX, GCGX, GGAX, GGTX, GGCX, and GGGX, wherein X may be selected from the group consisting of A, T, U, G, C and analogues thereof, wherein C may be 5-methylcytosine and/or T may be replaced with U. It will be recognized that when referring to (naturally occurring) nucleobases A, T, U, G, C, these may be substituted with nucleobase analogues which function as the equivalent natural nucleobase (e.g. base pair with the complementary nucleoside). In some embodiments region B does not comprise a T or U.

Amino Alkyl Intermediates

The invention further provides for the LNA oligomer intermediates which comprise an antisense LNA oligomer which comprises an (e.g. terminal, 5' or 3') amino alkyl linker, such as a C2-C36 amino alkyl group, for example a C6 to C12 amino alkyl group, including for example C6 and C12 amino alkyl groups. The amino alkyl group may be added to the LNA oligomer as part of standard oligonucleotide synthesis, for example using a (e.g. protected) amino alkyl phosphoramidite. The linkage group between the amino alkyl and the LNA oligomer may for example be a phosphorothioate or a phosphodiester, or one of the other nucleoside linkage groups referred to herein, for example. The amino alkyl group may be covalently linked to, for example, the 5' or 3' of the LNA oligomer, such as by the nucleoside linkage group, such as phosphorothioate or phosphodiester linkage.

The invention also provides a method of synthesis of the LNA oligomer comprising the sequential synthesis of the LNA oligomer, such as solid phase oligonucleotide synthesis, comprising the step of adding a amino alkyl group to the oligomer, such as e.g. during the first or last round of oligonucleotide synthesis. The method of synthesis may further comprise the step of reacting the a conjugate to the amino alkyl-LNA oligomer (the conjugation step). The a conjugate may comprise suitable linkers and/or branch point groups, and optionally further conjugate groups, such as hydrophobic or lipophilic groups, as described herein. The conjugation step may be performed whilst the oligomer is bound to the solid support (e.g. after oligonucleotide synthesis, but prior to elution of the oligomer from the solid support), or subsequently (i.e. after elution). The invention provides for the use of an amino alkyl linker in the synthesis of the oligomer of the invention.

Method of Manufacture/Synthesis

The invention provides for a method of synthesizing (or manufacture) of an oligomeric compound, such as the oligomeric compound of the invention, said method comprising either:

a) a step of providing a [solid phase] oligonucleotide synthesis support to which one of the following is attached [third region]:
  i) a linker group (—Y—)
  ii) a group selected from the group consisting of a conjugate, a targeting group, a blocking group, a reactive group [e.g. an amine or an alcohol] or an activation group(X—)
  iii) an —Y—X group
and
b) a step of [sequential] oligonucleotide synthesis of region B followed by region A, and/or:
c) a step of [sequential] oligonucleotide synthesis of a first region (A) and a second region (B), wherein the synthesis step is followed by
d) a step of adding a third region [phosphoramidite comprising]
  i) a linker group (—Y—)
  ii) a group selected from the group consisting of a conjugate, a targeting group, a blocking group, a reactive group [e.g. an amine or an alcohol] or an activation group (X—)
  iii) an —Y—X group
followed by
e) the cleavage of the oligomeric compound from the [solid phase] support wherein, optionally said method further comprises a further step selected from:
f) wherein the third group is an activation group, the step of activating the activation group to produce a reactive group, followed by adding a conjugate, a blocking, or targeting group to the reactive group, optionally via a linker group (Y);

g) wherein the third region is a reactive group, the step of adding a conjugate, a blocking, or targeting group to the reactive group, optionally via a linker group (Y).

h) wherein the third region is a linker group (Y), the step of adding a conjugate, a blocking, or targeting group to the linker group (Y)

wherein steps f), g) or h) are performed either prior to or subsequent to cleavage of the oligomeric compound from the oligonucleotide synthesis support. In some embodiments, the method may be performed using standard phosphoramidite chemistry, and as such the region X and/or region X or region X and Y may be provided, prior to incorporation into the oligomer, as a phosphoramidite. Please see FIGS. 5-10 which illustrate non-limiting aspects of the method of the invention.

The invention provides for a method of synthesizing (or manufacture) of an oligomeric compound, such as the oligomeric compound of the invention, said method comprising a step of sequential oligonucleotide synthesis of a first region (A) and a second region (B), wherein the synthesis step is followed by a step of adding a third region phosphoramidite comprising region X (also referred to as region C) or Y, such as a region comprising a group selected from the group consisting of a conjugate, a targeting group, a blocking group, a functional group, a reactive group (e.g. an amine or an alcohol) or an activation group (X), or an —Y—X group followed by the cleavage of the oligomeric compound from the [solid phase] support.

It is however recognized that the region X or X—Y may be added after the cleavage from the solid support. Alternatively, the method of synthesis may comprise the steps of synthesizing a first (A), and optionally second region (B), followed by the cleavage of the oligomer from the support, with a subsequent step of adding a third region, such as X or X—Y group to the oligomer. The addition of the third region may be achieved, by example, by adding an amino phosphoramidite unit in the final step of oligomer synthesis (on the support), which can, after cleavage from the support, be used to join to the X or X—Y group, optionally via an activation group on the X or Y (when present) group. In the embodiments where the cleavable linker is not a nucleotide region, region B may be a non-nucleotide cleavable linker for example a peptide linker, which may form part of region X (also referred to as region C) or be region Y (or part thereof).

In some embodiments of the method, region X (such as C) or (X-Y), such as the conjugate (e.g. a GalNAc conjugate) comprises an activation group, (an activated functional group) and in the method of synthesis the activated conjugate (or region x, or X-Y) is added to the first and second regions, such as an amino linked oligomer. The amino group may be added to the oligomer by standard phosphoramidite chemistry, for example as the final step of oligomer synthesis (which typically will result in amino group at the 5' end of the oligomer). For example during the last step of the oligonucleotide synthesis a protected amino-alkyl phosphoramidite is used, for example a TFA-aminoC6 phosphoramidite (6-(Trifluoroacetylamino)-hexyl-(2-cyanoethyl)-(N,N-diisopropyl)-phosphoramidite).

Region X (or region C as referred to herein), such as the conjugate (e.g. a GalNAc conjugate) may be activated via NHS ester method and then the aminolinked oligomer is added. For example a N-hydroxysuccinimide (NHS) may be used as activating group for region X (or region C, such as a conjugate, such as a GalNAc conjugate moiety).

The invention provides an oligomer prepared by the method of the invention.

In some embodiments, region X and/or region X or region X and Y may be covalently joined (linked) to region B via a phosphate nucleoside linkage, such as those described herein, including phosphodiester or phosphorothioate, or via an alternative group, such as a triazol group.

In some embodiments, the internucleoside linkage between the first and second region is a phosphodiester linked to the first (or only) DNA or RNA nucleoside of the second region, or region B comprises at least one phosphodiester linked DNA or RNA nucleoside.

The second region may, in some embodiments, comprise further DNA or RNA nucleosides which may be phosphodester linked. The second region is further covalently linked to a third region which may, for example, be a conjugate, a targeting group a reactive group, and/or a blocking group.

In some aspects, the present invention is based upon the provision of a labile region, the second region, linking the first region, e.g. an antisense oligonucleotide, and a conjugate or functional group, e.g. a targeting or blocking group. The labile region comprises at least one phosphodiester linked nucleoside, such as a DNA or RNA nucleoside, such as 1, 2, 3, 4, 5, 6, 7, 8, 9 or 10 phosphodiester linked nucleosides, such as DNA or RNA. In some embodiments, the oligomeric compound comprises a cleavable (labile) linker. In this respect the cleavable linker is preferably present in region B (or in some embodiments, between region A and B).

Alternatively stated, in some embodiments, the invention provides a non-phosphodiester linked, such as a phosphorothioate linked, oligonucleotide (e.g. an antisense oligonucleotide) which has at least one terminal (5' and/or 3') DNA or RNA nucleoside linked to the adjacent nucleoside of the oligonucleotide via a phosphodiester linkage, wherein the terminal DNA or RNA nucleoside is further covalently linked to a conjugate moiety, a targeting moiety or a blocking moiety, optionally via a linker moiety.

Compositions

The oligomer or oligomer conjugates of the invention may be used in pharmaceutical formulations and compositions. Suitably, such compositions comprise a pharmaceutically acceptable diluent, carrier, salt or adjuvant. WO2007/031091 provides suitable and preferred pharmaceutically acceptable diluent, carrier and adjuvants—which are hereby incorporated by reference. Suitable dosages, formulations, administration routes, compositions, dosage forms, combinations with other therapeutic agents, pro-drug formulations are also provided in WO2007/031091-which are also hereby incorporated by reference.

Applications

The oligomers or oligomer conjugates of the invention may be utilized as research reagents for, for example, diagnostics, therapeutics and prophylaxis.

In research, such oligomers may be used to specifically inhibit the synthesis of PCSK9 protein (typically by degrading or inhibiting the mRNA and thereby prevent protein formation) in cells and experimental animals thereby facilitating functional analysis of the target or an appraisal of its usefulness as a target for therapeutic intervention.

In diagnostics the oligomers may be used to detect and quantitate PCSK9 expression in cell and tissues by northern blotting, in-situ hybridisation or similar techniques.

For therapeutics, an animal or a human, suspected of having a disease or disorder, which can be treated by modulating the expression of PCSK9 is treated by administering oligomeric compounds in accordance with this invention. Further provided are methods of treating a mammal, such as treating a human, suspected of having or being prone to a disease or condition, associated with expression of PCSK9 by administering a therapeutically or prophylactically effective amount of one or more of the oligomers or compositions of the invention. The oligomer, a conjugate or a pharmaceutical composition according to the invention is typically administered in an effective amount.

The invention also provides for the use of the compound or conjugate of the invention as described for the manufacture of a medicament for the treatment of a disorder as referred to herein, or for a method of the treatment of as a disorder as referred to herein.

The invention also provides for a method for treating a disorder as referred to herein said method comprising administering a compound according to the invention as herein described, and/or a conjugate according to the invention, and/or a pharmaceutical composition according to the invention to a patient in need thereof.

Medical Indications

The oligomers, oligomer conjugates and other compositions according to the invention can be used for the treatment of conditions associated with over expression or expression of mutated version of the PCSK9.

The invention further provides use of a compound of the invention in the manufacture of a medicament for the treatment of a disease, disorder or condition as referred to herein.

Generally stated, one aspect of the invention is directed to a method of treating a mammal suffering from or susceptible to conditions associated with abnormal levels and/or activity of PCSK9, comprising administering to the mammal and therapeutically effective amount of an oligomer or oligomer conjugate targeted to PCSK9 that comprises one or more LNA units. The oligomer, a conjugate or a pharmaceutical composition according to the invention is typically administered in an effective amount.

The disease or disorder, as referred to herein, may, in some embodiments be associated with a mutation in the PCSK9 gene or a gene whose protein product is associated with or interacts with PCSK9. Therefore, in some embodiments, the target mRNA is a mutated form of the PCSK9 sequence.

An interesting aspect of the invention is directed to the use of an oligomer (compound) as defined herein or a conjugate as defined herein for the preparation of a medicament for the treatment of a disease, disorder or condition as referred to herein.

The methods of the invention are preferably employed for treatment or prophylaxis against diseases caused by abnormal levels and/or activity of PCSK9.

Alternatively stated, In some embodiments, the invention is furthermore directed to a method for treating abnormal levels and/or activity of PCSK9, said method comprising administering a oligomer of the invention, or a conjugate of the invention or a pharmaceutical composition of the invention to a patient in need thereof.

The invention also relates to an oligomer, a composition or a conjugate as defined herein for use as a medicament.

The invention further relates to use of a compound, composition, or a conjugate as defined herein for the manufacture of a medicament for the treatment of abnormal levels and/or activity of PCSK9 or expression of mutant forms of PCSK9 (such as allelic variants, such as those associated with one of the diseases referred to herein).

Moreover, the invention relates to a method of treating a subject suffering from a disease or condition such as those referred to herein.

A patient who is in need of treatment is a patient suffering from or likely to suffer from the disease or disorder.

In some embodiments, the term 'treatment' as used herein refers to both treatment of an existing disease (e.g. a disease or disorder as herein referred to), or prevention of a disease, i.e. prophylaxis. It will therefore be recognised that treatment as referred to herein may, In some embodiments, be prophylactic.

In one embodiment, the invention relates to compounds or compositions comprising compounds for treatment of hypercholesterolemia and related disorders, or methods of treatment using such compounds or compositions for treating hypercholesterolemia and related disorders, wherein the term "related disorders" when referring to hypercholesterolemia refers to one or more of the conditions selected from the group consisting of: atherosclerosis, hyperlipidemia, hypercholesterolemia, familiar hypercholesterolemia e.g. gain of function mutations in PCSK9, HDL/LDL cholesterol imbalance, dyslipidemias, e.g., familial hyperlipidemia (FCHL) or familial hypercholesterolemia(FHC), acquired hyperlipidemia, statin-resistant hypercholesterolemia, coronary artery disease (CAD), and coronary heart disease (CHD).

Combination Treatments

In some embodiments the compound of the invention is for use in a combination treatment with another therapeutic agent. E.g. inhibitors of HMG CoA reductase, such as statins for example are widely used in the treatment of metabolic disease (see WO2009/043354, hereby incorporated by reference for examples of combination treatments). Combination treatments may be other cholesterol lowering compounds, such as a compound selected from the group consisting of bile salt sequestering resins (e.g., cholestyramine, colestipol, and colesevelam hydrochloride), HMGCoA-reductase inhibitors (e.g., lovastatin, cerivastatin, pravastatin, atorvastatin, simvastatin, rosuvastatin, and fluvastatin), nicotinic acid, fibric acid derivatives (e.g., clofibrate, gemfibrozil, fenofibrate, bezafibrate, and ciprofibrate), probucol, neomycin, dextrothyroxine, plant-stanol esters, cholesterol absorption inhibitors (e.g., ezetimibe), implitapide, inhibitors of bile acid transporters (apical sodium-dependent bile acid transporters), regulators of hepatic CYP7a, estrogen replacement therapeutics (e.g., tamoxifen), and anti-inflammatories (e.g., glucocorticoids). Combinations with statins may be particularly preferred.

Specific Embodiments of the Invention

1. An antisense oligonucleotide conjugate comprising
   a. an antisense oligomer (A) of between 12-22 nucleotides in length, which comprises a contiguous sequence of 10-16 nucleotides which are complementary to a corresponding length of SEQ ID NO 30 or 31 or 32 or 33 or 34 or 45, and
   b. at least one non-nucleotide or non-polynucleotide conjugate moiety (C) covalently attached to said oligomer (A).
2. The oligonucleotide conjugate according to embodiment 1, wherein the antisense oligomer comprises a contiguous sequence selected from the group consisting of SEQ ID NO 25, 26, 27, 28, 29 and 44.
3. The oligonucleotide conjugate according any one of embodiments 1 or 2, wherein the antisense oligomer targets PCSK9.

4. The oligonucleotide conjugate according to any one of 1 to 3, wherein the antisense oligomer comprises affinity enhancing nucleotide analogues.
5. The oligonucleotide conjugate according to embodiment 4, wherein the nucleotide analogues are sugar modified nucleotides, such as sugar modified nucleotides independently or dependently selected from the group consisting of: Locked Nucleic Acid (LNA) units; 2'-O-alkyl-RNA units, 2'-OMe-RNA units, 2'-amino-DNA units, and 2'-fluoro-DNA units.
6. The oligonucleotide conjugate according to embodiment 4 or 5, wherein the nucleotide analogues comprise or are Locked Nucleic Acid (LNA) units.
7. The oligonucleotide conjugate according to any one of embodiments 1 to 6, wherein the antisense oligomer is a gapmer.
8. The oligonucleotide conjugate according to embodiment 7, wherein the gapmer comprise a wing on each side (5' and 3') of 2 to 4 nucleotide analogues, preferably LNA analogues.
9. The oligonucleotide conjugate according to embodiment 7 or 8, wherein the gapmer design is selected from the group consisting of 2-8-2, 3-8-3, 2-8-3, 3-8-2, 4-8-2, 2-8-4, 2-9-2, 2-9-3, 3-9-2, 3-9-3, 3-9-4, 4-9-3, 2-10-2, 2-10-3, 3-10-2, 3-10-3, 3-10-4, 4-10-3, 2-11-2, 2-11-3, 3-11-2, 3-11-3, 3-11-4, 4-11-3 and 4-11-4.
10. The oligonucleotide conjugate according to any one of the embodiments 7 to 9, wherein the gapmer design is selected from the group consisting of 2-8-3, 3-8-3, 3-9-4, 3-10-3, 2-11-2, 2-11-3 and 3-11-2.
11. The oligonucleotide conjugate according to any one of the embodiments 1 to 10, wherein the oligomer comprises a contiguous sequence of 13, 14, 15 or 16 nucleotides.
12. The oligonucleotide conjugate according to any one of the embodiments 1 to 11, wherein the oligomer comprises one or more nucleoside linkages selected from the group consisting of phosphorothioate, phosphorodithioate and boranophosphate.
13. The oligonucleotide conjugate according to any one of embodiments 1 to 12, wherein the oligomer comprises or consist of phosphorothioate nucleoside linkages.
14. The oligonucleotide conjugate according to any one of the embodiments 1 to 12, wherein the oligomer comprises a contiguous sequence selected from the group consisting of SEQ ID NO 1, 2, 3, 4, 5, 6, 7, and 8.
15. The oligonucleotide conjugate according to any one of the embodiments 1 to 14, wherein the conjugate moiety (C) is selected from the group consisting of or a carbohydrate, such as GalNAc or a GalNAc cluster; a lipophilic group, such as a lipid, a fatty acid; a sterol, such as cholesterol or tocopherol; or a statin.
16. The antisense oligonucleotide conjugate according to any one of embodiments 1 to 15, wherein the conjugate moiety (C) enhances delivery and/or uptake to liver cells.
17. The antisense oligonucleotide conjugate according to any one of embodiments 1 to 16, wherein the conjugate moiety (C) comprises a sterol such as tocophorol, cholesterol, such as those shown as Conj 5, Conj 5, Conj 6 or Conj 6a.
18. The antisense oligonucleotide conjugate according to embodiment 1 to 16, wherein the conjugate moiety (C) comprises a carbohydrate such as GalNAc or trivalent GalNAc, such as those shown as Conj 1, 2, 3 or 4, or 1a, 2a, 3a or 4a.
19. The antisense oligonucleotide conjugate according to embodiment 18, wherein the conjugate moiety (C) comprises Conj 2a.
20. The antisense oligonucleotide conjugate according to any one of embodiments 1 to 19, which is selected from the group consisting of SEQ ID NO 9, 10, 11, 12, 13, 14, 15, 16, 17, 18, 19, 20, 21, 22, 23, and 24.
21. The antisense oligonucleotide conjugate according to any one of embodiments 1 to 20, wherein the antisense oligomer (A) is conjugated to the conjugate moiety (C) via a linker region positioned between the contiguous sequence of the oligomer and the conjugate moiety (B and/or Y).
22. The antisense oligonucleotide conjugate according to embodiment 21, wherein the linker is selected from the group consisting of amino alkyl linkers, phosphate nucleotide linkers and peptide linkers.
23. The antisense oligonucleotide conjugate according to embodiment 21 or 22, wherein the linker is selected from a C6 to C12 amino alkyl groups.
24. The antisense oligonucleotide conjugate according to embodiment 21 or 22, wherein the linker is a bioclevable phosphate nucleotide linker comprising between 1 to 6 nucleotides.
25. The antisense oligonucleotide conjugate according to any of embodiments 21 to 24, wherein the linker (B) is a phosphodiester nucleotide linkage comprising one or more contiguous DNA phosphodiester nucleotides, such as 1, 2, 3, 4, 5, or 6 DNA phosphodiester nucleotides which are contiguous with the 5' or 3' end of the contiguous sequence of the oligomer, and which may or may not form complementary base pairing with the PCSK9 target sequence.
26. The antisense oligonucleotide conjugate according to embodiment 24 or 25, wherein the phosphodiester nucleotide linkage (or biocleavable linker) comprises 1, 2 or 3 DNA phosphodiester nucleotides, such as two DNA phosphodiester nucleotides, such as a 5' CA 3' dinucleotide.
27. A oligomer of between 12-22 nucleotides in length, which either comprises
  a. a contiguous sequence of 16 nucleotides which are complementary to a corresponding length of SEQ ID NO 31, or
  b. a contiguous sequence of 10-16 nucleotides which are complementary to a corresponding length of SEQ ID NO 33 or 34 or 45.
28. The oligomer according to embodiment 27, which comprises a contiguous sequence selected from the group consisting of SEQ ID NO 26, 27, 28, 29 and 44.
29. The oligomer according any one of embodiments 27 or 28, wherein the oligomer targets PCSK9.
30. The oligomer according to any one of embodiments 27 to 29 wherein the contiguous sequence comprises affinity enhancing nucleotide analogues.
31. The oligomer according to embodiment 30, wherein the nucleotide analogues are sugar modified nucleotides, such as sugar modified nucleotides independently or dependently selected from the group consisting of: Locked Nucleic Acid (LNA) units; 2'-O-alkyl-RNA units, 2'-OMe-RNA units, 2'-amino-DNA units, and 2'-fluoro-DNA units.
32. The oligomer according to embodiment 30 or 31, wherein the nucleotide analogues comprise or are Locked Nucleic Acid (LNA) units.
33. The oligomer according to any one of embodiments 27 to 32, which is a gapmer, such as a Locked Nucleic Acid gapmer oligonucleotide.

34. The oligonucleotide conjugate according to embodiment 33, wherein the gapmer comprise a wing on each side (5' and 3') of 2 to 4 nucleotide analogues, preferably LNA analogues.
35. The oligonucleotide conjugate according to embodiment 33 or 34, wherein the gapmer design is selected from the group consisting of 2-8-2, 3-8-3, 2-8-3, 3-8-2, 4-8-2, 2-8-4, 2-9-2, 2-9-3, 3-9-2, 3-9-3, 3-9-4, 4-9-3, 2-10-2, 2-10-3, 3-10-2, 3-10-3, 3-10-4, 4-10-3, 2-11-2, 2-11-3, 3-11-2, 3-11-3, 3-11-4, 4-11-3 and 4-11-4.
36. The oligonucleotide conjugate according to any one of the embodiments 33 to 35, wherein the gapmer design is selected from the group consisting of 2-8-3, 3-8-3, 3-9-4, 3-10-3, 2-11-2, 2-11-3 and 3-11-2.
37. The oligomer according to any one of embodiments 27 to 36, wherein the oligomer comprises a contiguous sequence of 13, 14, 15 or 16 nucleotides.
38. The oligomer according to any one of embodiments 27 to 37, wherein the oligomer comprises one or more nucleoside linkages selected from the group consisting of phosphorothioate, phosphorodithioate and boranophosphate.
39. The oligomer according to any one of embodiments 27 to 38, wherein the oligomer comprises or consist of phosphorothioate nucleoside linkages.
40. Then oligomer according to any one of embodiments 27 to 38, which comprises a contiguous sequence selected from the group consisting of SEQ ID NO 2, 3, 4, 5, 6, 7, and 8.
41. A pharmaceutical composition comprising the oligomer or antisense oligonucleotide conjugate according to any one of embodiments 1 to 40 and a pharmaceutically acceptable diluent, carrier, salt or adjuvant.
42. The oligomer or antisense oligonucleotide conjugate or pharmaceutical composition according to any one of embodiments 1 to 41, for use as a medicament, such as for the treatment of hypercholesterolemia or related disorder, such as a disorder selected from the group consisting of atherosclerosis, hyperlipidemia, hypercholesterolemia, familiar hypercholesterolemia e.g. gain of function mutations in PCSK9, HDL/LDL cholesterol imbalance, dyslipidemias, e.g., familial hyperlipidemia (FCHL) or familial hypercholesterolemia (FHC), acquired hyperlipidemia, statin-resistant hypercholesterolemia, coronary artery disease (CAD), and coronary heart disease (CHD).
43. The use of an oligomer or antisense oligonucleotide conjugate or pharmaceutical composition according to any one of the embodiments 1 to 41, for the manufacture of a medicament for the treatment of hypercholesterolemia or a related disorder, such as a disorder selected from the group consisting of atherosclerosis, hyperlipidemia, hypercholesterolemia, familiar hypercholesterolemia e.g. gain of function mutations in PCSK9, HDL/LDL cholesterol imbalance, dyslipidemias, e.g., familial hyperlipidemia (FCHL) or familial hypercholesterolemia (FHC), acquired hyperlipidemia, statin-resistant hypercholesterolemia, coronary artery disease (CAD), and coronary heart disease (CHD).
44. A method of treating hypercholesterolemia or a related disorder, such as a disorder selected from the group consisting atherosclerosis, hyperlipidemia, hypercholesterolemia, familiar hypercholesterolemia e.g. gain of function mutations in PCSK9, HDL/LDL cholesterol imbalance, dyslipidemias, e.g., familial hypercholesterolemia(FHC), acquired hyperlipidemia, statin-resistant hypercholesterolemia, coronary artery disease (CAD), and coronary heart disease (CHD), said method comprising administering an effective amount of an oligomer or antisense oligonucleotide conjugate or pharmaceutical composition according to any one of the embodiments 1 to 41, to a patient suffering from, or likely to suffer from hypercholesterolemia or a related disorder.
45. A in vivo or in vitro method for the inhibition of PCSK9 in a cell which is expressing PCSK9, said method comprising administering an oligomer or antisense oligonucleotide conjugate or pharmaceutical composition according to any one of the embodiments 1 to 41, to said cell so as to inhibit PCSK9 in said cell.

EXAMPLES

Oligonucleotides were synthesized on uridine universal supports using the phosphoramidite approach on an Expedite 8900/MOSS synthesizer (Multiple Oligonucleotide Synthesis System) or Oligomaker 48 at 4 or 1 µmol scale, respectively. At the end of the synthesis, the oligonucleotides were cleaved from the solid support using aqueous ammonia for 5-16 hours at 60° C. The oligonucleotides were purified by reverse phase HPLC (RP-HPLC) or by solid phase extractions and characterized by UPLC, and the molecular mass was further confirmed by ESI-MS. See below for more details.

Elongation of the Oligonucleotide

The coupling of β-cyanoethyl-phosphoramidites (DNA-A(Bz), DNA-G(ibu), DNA-C(Bz), DNA-T, LNA-5-methyl-C(Bz), LNA-A(Bz), LNA-G(dmf), LNA-T or C6-S-S-C6 linker) is performed by using a solution of 0.1 M of the 5'-O-DMT-protected amidite in acetonitrile and DCI (4,5-dicyanoimidazole) in acetonitrile (0.25 M) as activator. For the final cycle a commercially available C6-linked cholesterol phosphoramidite was used at 0.1 M in DCM. Thiolation for introduction of phosphorthioate linkages is carried out by using xanthane hydride (0.01 M in acetonitrile/pyridine 9:1). Phosphordiester linkages are introduced using 0.02 M iodine in THF/Pyridine/water 7:2:1. The rest of the reagents are the ones typically used for oligonucleotide synthesis. For post solid phase synthesis conjugation a commercially available C6 aminolinker phorphoramidite was used in the last cycle of the solid phase synthesis and after deprotection and cleavage from the solid support the aminolinked deprotected oligonucleotide was isolated. The conjugates was introduced via activation of the functional group using standard synthesis methods.

Purification by RP-HPLC:

The crude compounds were purified by preparative RP-HPLC on a Phenomenex Jupiter C18 10µ 150×10 mm column. 0.1 M ammonium acetate pH 8 and acetonitrile was used as buffers at a flow rate of 5 mL/min. The collected fractions were lyophilized to give the purified compound typically as a white solid.

Abbreviations

DCI: 4,5-Dicyanoimidazole
DCM: Dichloromethane
DMF: Dimethylformamide
DMT: 4,4'-Dimethoxytrityl
THF: Tetrahydrofurane
Bz: Benzoyl
Ibu: Isobutyryl
RP-HPLC: Reverse phase high performance liquid chromatography The compounds synthesized are shown in Table 1 and are also illustrated in the Figures.

Example 1 New PCSK9 Target Motif Discovery 521 anti-PCSK9 antisense oligonucleotides—all with three locked nucleic acids flanking ten DNAs, i.e with 16-mer LNA gap-mer design—specific for human and primate PCSK9 were designed and synthesized. The human cell line 15PC3 was incubated for three days with either mock or the locked nucleic acid-modified oligonucleotides targeted to human PCSK9 at concentration 0.3 µM. Each anti-PCSK9 oligonucleotide was tested in three independent experiments. PCSK9 mRNA levels were quantitated from extracted RNA using real-time PCR as described, and presented normalized to 1-actin mRNA and relative to average levels in twelve mock treated samples in FIG. 8, with a close-up of a sub-set of the most potent molecules in FIG. 9.

Example 2 In Vitro mRNA Knockdown

The human cell line 15PC3 was incubated for 3 days with either mock or locked nucleic acid modified oligonucleotides with SEQ IDs 1 to 8 targeted to human PCSK9 at concentrations 0.0012, 0.06, 0.3 and 1.5 µM. PCSK9 mRNA levels were quantitated from extracted RNA using real-time PCR as described, and presented relative to average levels in four mock treated samples in FIG. 10. For each oligonucleotide, potency, quantified as half maximal effective concentration (EC50), was determined by least squares fitting of the Hill equation in two-parameter logistic form with lower limit fixed at 0% and upper limit fixed at 100%, as EC50=estimate±standard deviation.

Example 3—In Vivo ALT Levels

Figure 11:
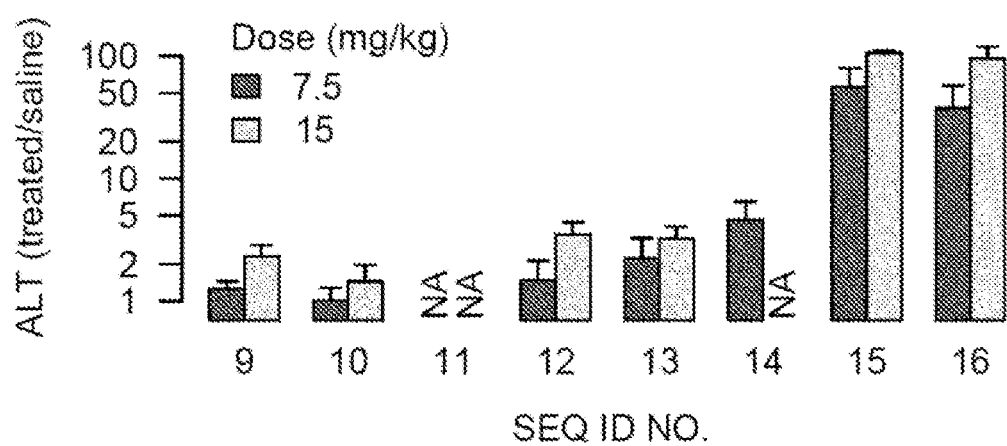
FIG. 11: In vivo ALT data for selected anti-PCSK9 conjugates.

Four week old female NMRI mice (Taconic, Denmark), weighing approximately 20 g at arrival, were injected intravenously once with either saline or locked nucleic acid-modified, cholesterol-conjugated, oligonucleotides with SEQ IDs 9 to 16 targeted to human PCSK9 at doses 7.5 and 15 mg/kg. The mice were sacrificed 7 days following administration and serum levels of alanine aminotransferase (ALT) determined using an enzymatic assay (Horiba ABX Diagnostics). For each treatment group of five mice, mean and standard deviations were calculated and presented in FIG. 11 relative to mean levels in saline treated mice. ALT rises were noted at both concentrations for some, but not all, cholesterol conjugated molecules. Several of the compounds, such as SEQ ID NO 9 and 10, did not enhance ALT in mice in a clinically meaningful manner even when cholesterol was used as a conjugate to enhance the uptake of compounds in the liver.

Example 4: Non-Human Primate Study

The primary objective for this study was to investigate selected lipid markers over 7 weeks after a single slow bolus injection of anti-PCSK9 LNA compounds to cynomolgus monkeys and assess the potential toxicity of compounds in monkey. The compounds used in this study were SEQ ID NOs 10 13, 18, 19, 20 & 21, prepared in sterile saline (0.9%) at an initial concentration of 0.625 and 2.5 mg/ml).

Male monkeys of at least 24 months old were used, and given free access to tap water and 180 g of MWM(E) SQC SHORT expanded diet (Dietex France, SDS, Saint Gratien, France) was distributed daily per animal. The total quantity of food distributed in each cage will be calculated according to the number of animals in the cage on that day. In addition, fruit or vegetables was given daily to each animal. The animals were acclimated to the study conditions for a period of at least 14 days before the beginning of the treatment period. During this period, pre-treatment investigations were performed. The animals were dosed i.v. at a single dose of 0.25, 1.0 or 2.5 mg/kg (SEQ ID NO 10, 13, 18, and 21) or at a single dose of 1.0 or 2.5 mg/kg (SEQ ID NO 19 and 20). The dose volume was 0.4 mL/kg. 2 animals were used per group.

The dose formulations were administered once on Day 1. Animals were observed for a period of 7 weeks following treatment, and were released from the study on Day 51. Day 1 corresponds to the first day of the treatment period. Clinical observations and body weight and food intake (per group) will be recorded prior to and during the study.

Blood was sampled and analyses performed at the following time points:

| Study Day | Parameters |
| --- | --- |
| −8 | RCP, L, Apo-B, PCSK9*, OA |
| −1 | L, Apo-B, PCSK9*, PK, OA |
| 1 | Dosing |
| 4 | LSB, L, Apo-B, PCSK9*, OA |
| 8 | LSB, L, Apo-B, PCSK9*, PK, OA |
| 15 | RCP, L, Apo-B, PCSK9* PK, OA |
| 22 | LSB, L, Apo-B, PCSK9* PK, OA |
| 29 | L, Apo-B, PCSK9* PK, OA |
| 36 | LSB, L, Apo-B, PCSK9* PK, OA |
| 43 | L, PK, Apo-B, PCSK9* PK, OA |
| 50 | RCP, L, Apo-B, PCSK9* PK, OA |

RCP 0 routine clinical pathology,
LSB = liver safety biochemistry,
PK = pharmacokinetics,
OA = other analysis,
L = Lipids.

The following parameters were determined for all surviving animals at the occasions indicated below:
  biochemistry panel (complete list below)—on Days −8, 15 and 50,
  liver Safety (ASAT, ALP, ALAT, TBIL and GGT only)— on Days 4, 8, 22 and 36,
  lipid profile (Total cholesterol, HDL-C, LDL-C and Triglycerides) and Apo-B only—on Days −1, 4, 8, 22, 29, 36, and 43.

Blood (approximately 1.0 mL) was taken into lithium heparin tubes (using the ADVIA 1650 blood biochemistry analyzer): Apo-B, sodium, potassium, chloride, calcium, inorganic phosphorus, glucose, HDL-C, LDL-C, urea, creatinine, total bilirubin (TBIL), total cholesterol, triglycerides, alkaline phosphatase (ALP), alanine aminotransferase (ALAT), aspartate aminotransferase (ASAT), creatine kinase, gamma-glutamyl transferase (GGT), lactate dehydrogenase, total protein, albumin, albumin/globulin ratio.

Analysis of PCSK9 in blood: Blood samples for PCSK9 analysis were collected from on Days −8, −1, 4, 8, 15, 22, 29, 36, 43 and 50. Venous blood (approximately 2 mL) was collected from an appropriate vein in each animal into a Serum Separating Tube (SST) and allowed to clot for at least 60±30 minutes at room temperature. Blood was centrifuged at 1000 g for 10 minutes under refrigerated conditions (set to maintain +4° C.). The serum will be transferred into 3 individual tubes and stored at −80° C. until analyzed at CitoxLAB France using an ELISA method (Circulex Human PCSK9 ELISA kit, CY-8079, validated for samples from cynomolgus monkey).

Other Analysis: WO2011009697 provides the methods for the following analysis: qPCR, PCSK9 mRNA analysis. Other analysis includes PCSK9 protein ELISA, serum Lp(a) analysis with ELISA (Mercodia No. 10-1106-01), tissue and plasma oligonucleotide analysis (drug content), Extraction of samples, standard- and QC-samples, Oligonucleotide content determination by ELISA.

The data for the PCSK9 targeting compounds is shown in the following table:

| Values for 2.5 mg/kg dose Compound SEQ ID | PCSK9 protein day 4 (percent of pre-dose) | PCSK9 protein day 29 (percent of pre-dose) | Max PCSK9 effect (data represent percent of pre-dose) | Max LDL-C effect (data represent percent of pre-dose) |
|---|---|---|---|---|
| 10 | 86 | 71.5 | 69% (d15) | 87% (d29) |
| 13 | 81 | 71 | 71% (d29) | 84% (d22) |
| 18 | 57 | 42 | 42% (d29) | 71% (d15) |
| 21 | 80.5 | 56 | 55% (d29) | 84% (d15) |
| 20 | 51 | 53 | 48% (d4) | 94% (D8) |
| 19 | 55 | 60 | 55% (d4) | 89% (D4) |

There was no indication of hepatotoxicity or nephrotoxicity with the PCSK9 targeting compounds. Notably, the PCSK9-GalNAc compounds gave a rapid and highly effective down regulation of PCSK9 which was maintained over an extensive time period (entire length of the study), illustrating that the GalNAc conjugated compounds are more effective, both in terms of a rapid initial knock-down, and long duration, indicating that they may be dosed comparatively infrequently and at a lower dosage, as compared to both the unconjugated parent compounds, and compounds using alternative conjugation technology, such as cholesterol conjugation. SEQ ID NO 18 gave rapid and consistent down regulation of PCSK9 and LDL-C throughout the duration of the study (seen at day 34 at 2.5 mg/kg dose, with notable PCSK9 down-regulation seen 48 days after the administration of the single 2.5 mg/kg dose where plasma PCSK9 protein level was 71% of pre-dose).

Example 5: Liver and Kidney Toxicity Assessment in Rat

Figure 15:
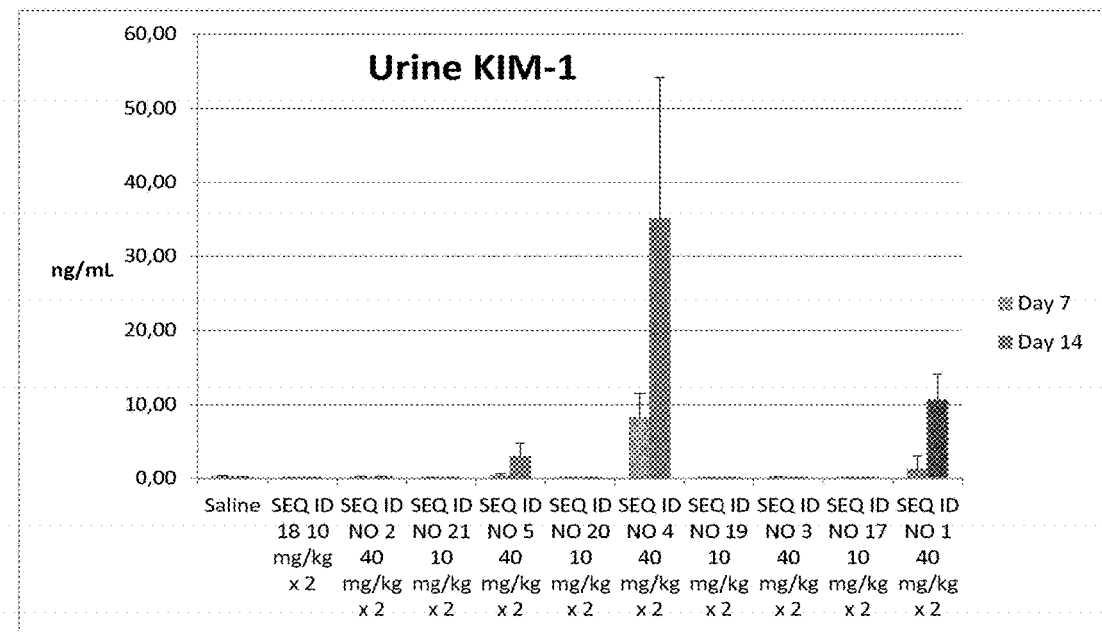
FIG. 15. Kim-1 expression from rat safety study (see Example 5).

Compounds of the invention can be evaluated for their toxicity profile in rodents, such as in mice or rats. The following protocol may be used: Wistar Han Crl:WI(Han) were used at an age of approximately 8 weeks old. At this age, the males weighed approximately 250 g. All animals had free access to SSNIFF R/M-H pelleted maintenance diet (SSNIFF Spezialdiaten GmbH, Soest, Germany) and to tap water (filtered with a 0.22 μm filter) contained in bottles. The dose level of 10 and 40 mg/kg/dose was used (sub-cutaneous administration) and dosed on days 1 and 8. The animals were euthanized on Day 15. Urine and blood samples were collected on day 7 and 14. A clinical pathology assessment was made on day 14. Body weight is determined prior to the study, on the first day of administration, and 1 week prior to necropsy. Food consumption per group was assessed daily. Blood samples were taken via the tail vein after 6 hours of fasting. The following blood serum analysis ws performed: erythrocyte count, mean cell volume packed cell volume, hemoglobin, mean cell hemoglobin concentration, thrombocyte count, leucocyte count, differential white cell count with cell morphology, reticulocyte count, sodium, potassium, chloride, calcium, inorganic phosphorus, glucose, urea, creatinine, total bilirubin, total cholesterol, triglycerides, alkaline phosphatase, alanine aminotransferase, aspartate aminotransferase, total protein, albumin, albumin/globulin ratio. Urinalysis was performed: α-GST, β-2 Microglobulin, Calbindin, Clusterin, Cystatin C, KIM-1, Osteopontin, TIMP-1, VEGF, and NGAL. Seven analytes (Calbindin, Clusterin, GST-α, KIM-1, Osteopontin, TIMP-1, VEGF) were quantified under Panel 1 (MILLIPLEX® MAP Rat Kidney Toxicity Magnetic Bead Panel 1, RKTX1MAG-37K). Three analytes (β-2 Microglobulin, Cystatin C, Lipocalin-2/NGAL) were quantified under Panel 2 (MILLIPLEX® MAP Rat Kidney Toxicity Magnetic Bead Panel 2, RKTX2MAG-37K). The assay for the determination of these biomarkers' concentration in rat urines was based on the Luminex xMAP® technology. Microspheres coated with anti-α-GST/β-2 microglobulin/calbindin/clusterin/cystacin C/KIM-1/osteopontin/TIMP-1/VEGF/NGAL antibodies were color-coded with two different fluorescent dyes. The following parameters were determined (Urine using the ADVIA 1650): Urine protein, urine creatinine. Quantitative parameters: volume, pH (using 10-Multistix SG test strips/Clinitek 500 urine analyzer), specific gravity (using a refractometer). Semi-quantitative parameters (using 10-Multistix SG test strips/Clinitek 500 urine analyzer): proteins, glucose, ketones, bilirubin, nitrites, blood, urobilinogen, cytology of sediment (by microscopic examination). Qualitative parameters: Appearance, color. After sacrifice, the body weight and kidney, liver and spleen weight are determined and organ to body weight ratio calculated. Kidney and liver samples was taken and either frozen or stored in formalin. Microscopic analysis was performed. The data for Kim-1 expression are shown in FIG. 15, where it is demonstrated that all molecules except SEQ ID NO 4 had a lower urinary kim-1 signal than SEQ ID NO 1, demonstrating improved kidney safety vs. the original and previously characterized unconjugated molecule.

Example 6 Analysis of Cleavable Linkers

FAM-labelled antisense oligomers (ASOs) with different DNA/PO-linkers were subjected to in vitro cleavage either in S1 nuclease extract (table below), Liver or kidney homogenates or Serum.

| SEQ ID NO | Seq (5'-3') | Cleavable linker (B) | Conjugate (C) |
|---|---|---|---|
| 35 | GCattggtatTCA | 3PO-DNA (5'tca3') | FAM |
| 36 | GCattggtatTCA | 2PO-DNA (5'ca3') | FAM |
| 37 | GCattggtatTCA | 1PO-DNA (5'a3') | FAM |
| 38 | GCattggtatTCA | 3PO-DNA (5'gac3') | FAM |
| 39 | GCattggtatTCA | no | FAM |

Figure 6:
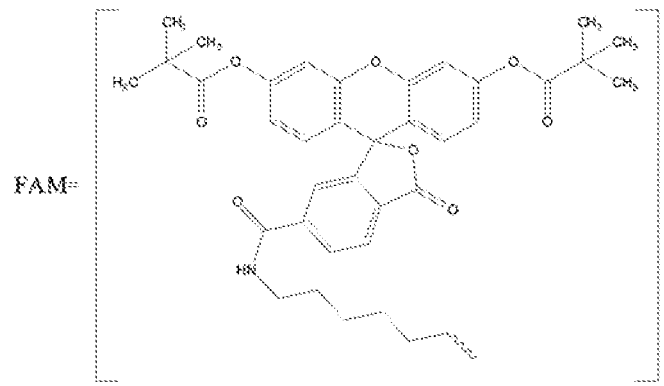
FIG. 6: Example of FAM conjugate group.
Figure 7:
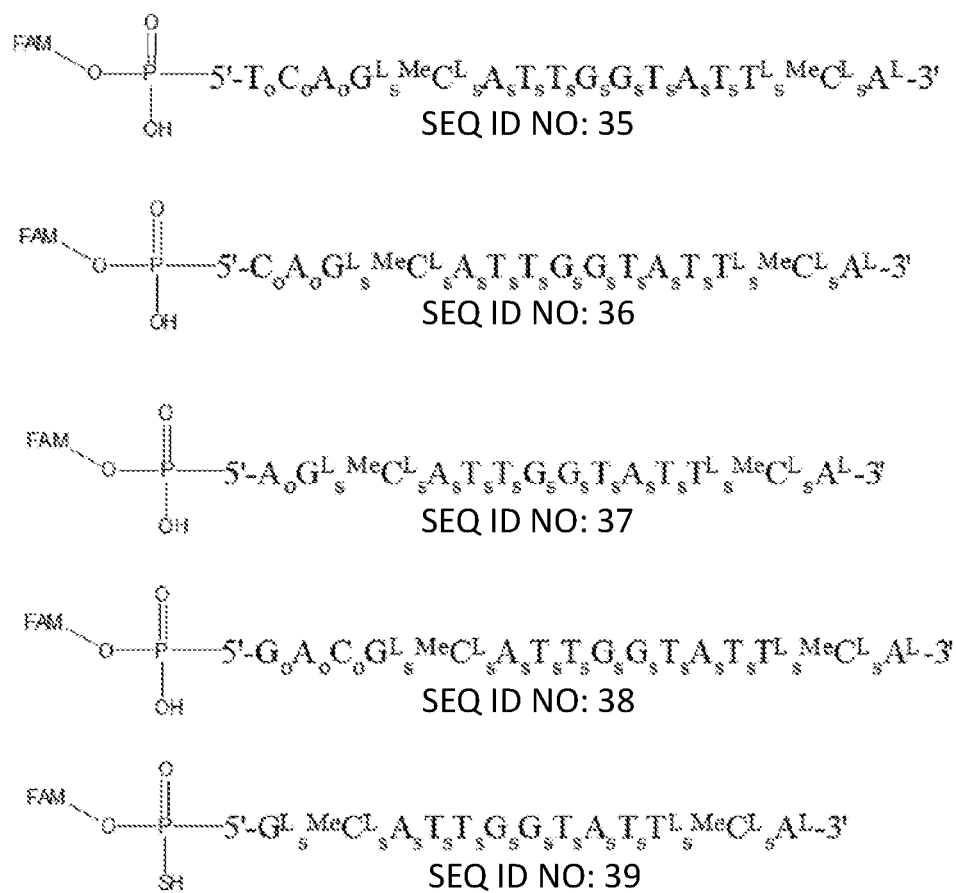
FIG. 7: LNA-FAM conjugates with and without cleavable phophodiester linkages. Beta-D-oxy LNA are identified by a superscript $^L$ after the letter, subscript $_s$ represents a phosphorothioate linkage, $_o$ subscript represents a phosphodiester linkage, superscript $^{Me}$ preceding a capital C represents 5-methyl cytosine LNA, non LNA nucleotides are DNA nucleotides (no superscript L).
Figure 8:
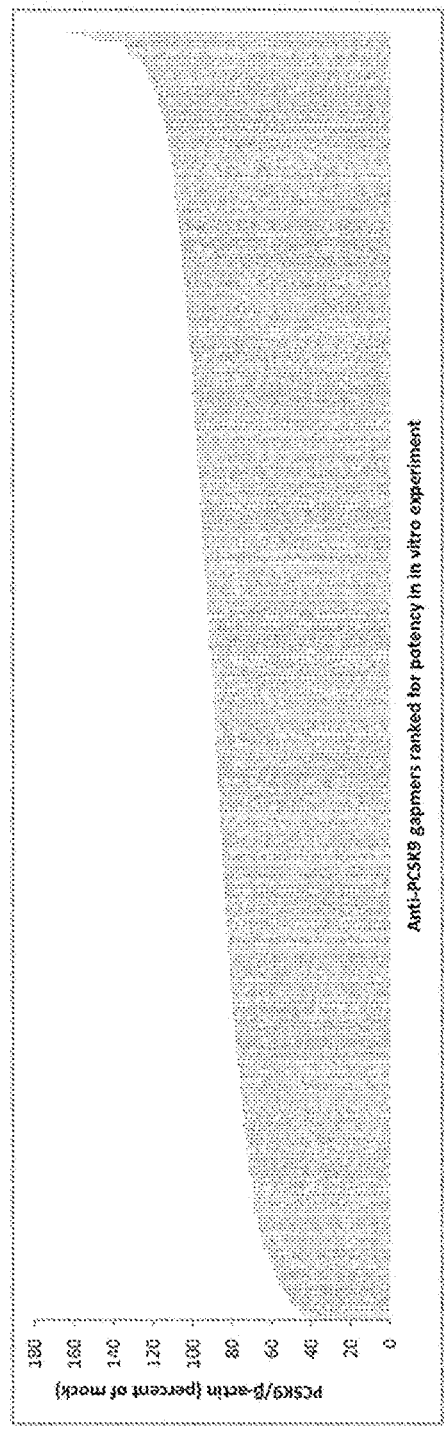
FIG. 8: Anti-PCSK9 gapmers ranked for potency in vitro.
Figure 9:
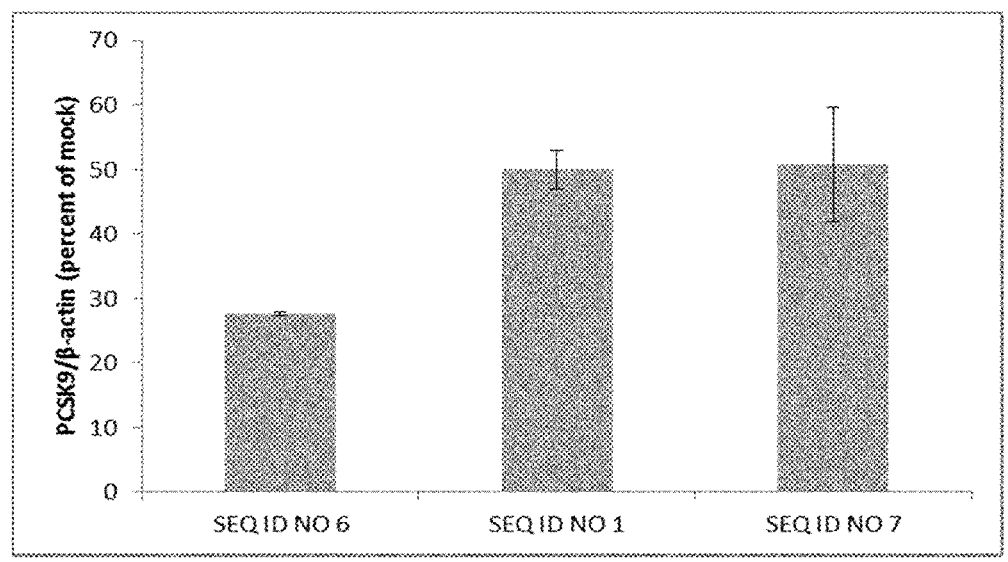
FIG. 9: Selected anti-PCSK9 gapmers ranked for potency in vitro.
Figure 10:
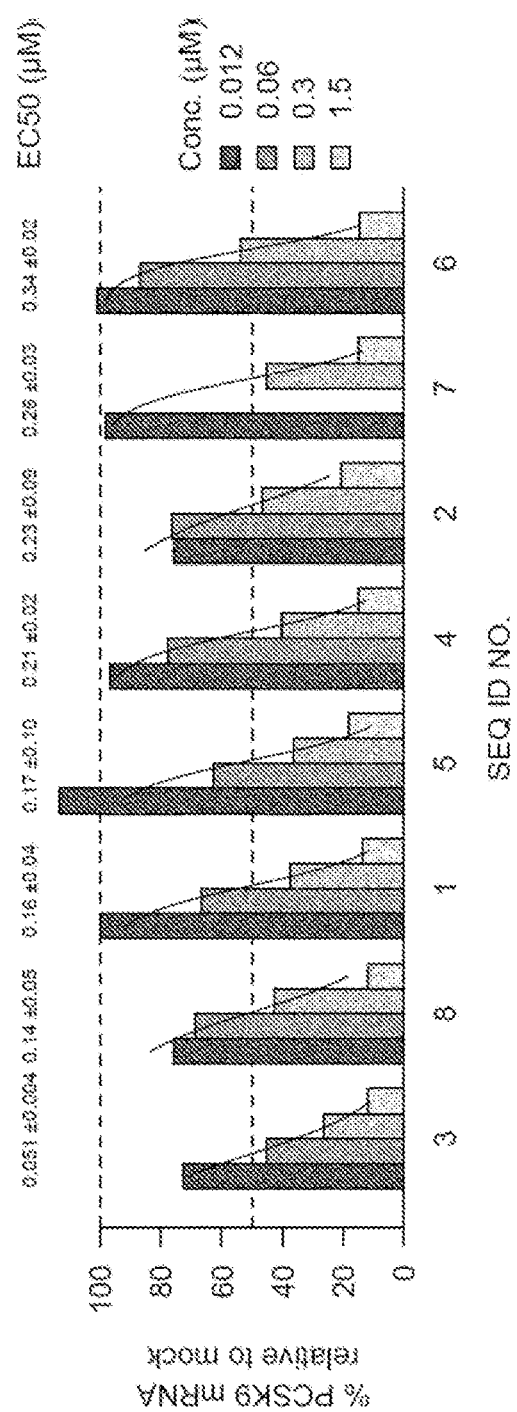
FIG. 10: In vitro potency of selected anti-PCSK9 compounds and IC50 calculations.

Capital letters are LNA nucleosides (such as beta-D-oxy LNA), lower case letters are DNA nucleosides. Subscript s represents a phosphorothioate internucleoside linkages. LNA cytosines are optionally 5-methyl cytosine. The FAM conjugate moiety is shown in FIG. 6 and the molecules are shown in FIG. 7.

FAM-labelled ASOs 100 μM with different DNA/PO-linkers were subjected to in vitro cleavage by S1 nuclease in nuclease buffer (60 U pr. 100 μL) for 20 and 120 minutes (A). The enzymatic activity was stopped by adding EDTA to the buffer solution. The solutions were then subjected to AIE HPLC analyses on a Dionex Ultimate 3000 using an Dionex DNApac p-100 column and a gradient ranging from 10 mM-1 M sodium perchlorate at pH 7.5. The content of cleaved and non-cleaved oligonucleotide were determined against a standard using both a fluorosensce detector at 615 nm and a uv detector at 260 nm.

| SEQ ID NO | Linker sequence | % cleaved after 20 min S1 | % cleaved after 120 min S1 |
|---|---|---|---|
| 39 | — | 2 | 5 |
| 37 | a | 29.1 | 100 |
| 36 | ca | 40.8 | 100 |
| 35 | tca | 74.2 | 100 |
| 38 | gac | 22.9 | n.d |

Conclusion

The PO linkers (or region B as referred to herein) results in cleavage of the conjugate (or group C), and both the length and/or the sequence composition of the linker can be used to modulate susceptibility to nucleolytic cleavage of region B. The Sequence of DNA/PO-linkers can modulate the cleavage rate as seen after 20 min in Nuclease S1 extract Sequence selection for region B (e.g. for the DNA/PO-linker) can therefore also be used to modulate the level of cleavage in serum and in cells of target tissues.

Liver and kidney homogenates and Serum were spiked with compound SEQ ID NO 35 to concentrations of 200 μg/g tissue. Liver and kidney samples collected from NMRI mice were homogenized in a homogenisation buffer (0.5% Igepal CA-630, 25 mM Tris pH 8.0, 100 mM NaCl, pH 8.0 (adjusted with 1 N NaOH). The homogenates were incubated for 24 hours at 37° C. and thereafter the homogenates were extracted with phenol-chloroform. The content of cleaved and non cleaved oligo in the extract from liver and kidney and from the serum were determined against a standard using the above HPLC method:

| Seq ID | Linker Sequence | % cleaved after 24 hrs liver homogenate | % cleaved afte 24 hrs kidney homogenate | % cleaved after 24 hours in serum |
|---|---|---|---|---|
| 35 | tca | 83 | 95 | 0 |

Conclusion

The PO linkers (or region B as referred to herein) results in the conjugate (or group C) being cleaved off, in liver or kidney homogenate, but not in serum. The susceptibility to cleavage in the assays shown in Example 6 may be used to determine whether a linker is biocleavable or physiologically labile. Note that cleavage in the above assays refers to the cleavage of the cleavable linker, the oligomer or region A should remain functionally intact.

Example 7: Knock Down of PCSK9 mRNA with Cholesterol Conjugates In Vivo PCSK9—Mouse Specific Compounds

| SEQ ID NO | Seq (5'-3') (A) | Cleavable Linker (B) | Conjugate (C) |
|---|---|---|---|
| 40 | GTctgtggaaGCG | no | no |
| 41 | GTctgtggaaGCG | no | Cholesterol |
| 42 | GTctgtggaaGCG | 2PO-DNA (5'ca3') | Cholesterol |
| 43 | GTctgtggaaGCG | 2PO-DNA (5'ct3') | Cholesterol |

NMRI mice were injected with a single dose saline or 10 mg/kg unconjugated LNA-antisense oligonucleotide (SEQ ID 40) or equimolar amounts of LNA antisense oligonucleotides conjugated to Cholesterol with different linkers and sacrificed at days 1-10 according to Tab. 5.

RNA was isolated from liver and kidney and subjected to qPCR with PCSK9 specific primers and probe to analyze for PCSK9 mRNA knockdown. The results are shown in FIG. 14.

Conclusions

Cholesterol conjugated to an PCSK9 LNA antisense oligonucleotide with a linker composed of 2 DNA with Phophodiester-backbone (SEQ ID NO 42 and SEQ ID NO 43) showed an enhanced liver knock down of PCSK9 (FIG. 14) compared to the unconjugated compound (SEQ ID NO 40), as well as compared to Cholesterol conjugates with stable linker (SEQ ID NO 41).

Materials and Methods:

Experimental Design:

| Part | Group no. | Animal id no. | No. of Animals | Animal strain/ gender/feed | Compound Dose level per day | Conc. at dose vol. 10 ml/kg | Adm. Route | Dosing day | Body weight day | Sacrifice day |
|---|---|---|---|---|---|---|---|---|---|---|
| A | 1 | 1-3 | 3 | NMRI/♀/Chow | Saline | — | iv | 0 | 0, 1 | 1 |
| | 2 | 4-6 | 3 | NMRI/♀/Chow | SEQ ID NO 40 10 mg/kg | 1 mg/ml | iv | 0 | 0, 1 | 1 |
| | 3 | 7-9 | 3 | NMRI/♀/Chow | SEQ ID NO 41 equimolar 11.3 mg/kg | 1.13 mg/ml | iv | 0 | 0, 1 | 1 |
| | 5 | 13-15 | 3 | NMRI/♀/Chow | SEQ ID NO 42 equimolar 12.7 mg/kg | 1.27 mg/ml | iv | 0 | 0, 1 | 1 |
| | 6 | 16-18 | 3 | NMRI/♀/Chow | SEQ ID NO 43 equimolar 12.7 mg/kg | 1.27 mg/ml | iv | 0 | 0, 1 | 1 |

-continued

| Part | Group no. | Animal id no. | No. of Animals | Animal strain/ gender/feed | Compound Dose level per day | Conc. at dose vol. 10 ml/kg | Adm. Route | Dosing day | Body weight day | Sacrifice day |
|---|---|---|---|---|---|---|---|---|---|---|
| B | 7 | 19-21 | 3 | NMRI/♀/Chow | Saline | — | iv | 0 | 0, 3 | 3 |
|  | 8 | 22-24 | 3 | NMRI/♀/Chow | SEQ ID NO 40 10 mg/kg | 1 mg/ml | iv | 0 | 0, 3 | 3 |
|  | 9 | 25-27 | 3 | NMRI/♀/Chow | SEQ ID NO 41 equimolar 11.3 mg/kg | 1.13 mg/ml | iv | 0 | 0, 3 | 3 |
|  | 11 | 31-33 | 3 | NMRI/♀/Chow | SEQ ID NO 42 equimolar 12.7 mg/kg | 1.27 mg/ml | iv | 0 | 0, 3 | 3 |
|  | 12 | 34-36 | 3 | NMRI/♀/Chow | SEQ ID NO 43 equimolar 12.7 mg/kg | 1.27 mg/ml | iv | 0 | 0, 3 | 3 |
| C | 13 | 37-39 | 3 | NMRI/♀/Chow | Saline | — | iv | 0 | 0, 7 | 7 |
|  | 14 | 40-42 | 3 | NMRI/♀/Chow | SEQ ID NO 40 10 mg/kg | 1 mg/ml | iv | 0 | 0, 7 | 7 |
|  | 15 | 43-45 | 3 | NMRI/♀/Chow | SEQ ID NO 41 equimolar 11.3 mg/kg | 1.13 mg/ml | iv | 0 | 0, 7 | 7 |
|  | 17 | 49-51 | 3 | NMRI/♀/Chow | SEQ ID NO 42 equimolar 12.7 mg/kg | 1.27 mg/ml | iv | 0 | 0, 7 | 7 |
|  | 18 | 52-54 | 3 | NMRI/♀/Chow | SEQ ID NO 43 equimolar 12.7 mg/kg | 1.27 mg/ml | iv | 0 | 0, 7 | 7 |
| D | 19 | 55-57 | 3 | NMRI/♀/Chow | Saline | — | iv | 0 | 0, 7, 10 | 10 |
|  | 20 | 58-60 | 3 | NMRI/♀/Chow | SEQ ID NO 40 10 mg/kg | 1 mg/ml | iv | 0 | 0, 7, 10 | 10 |
|  | 21 | 61-63 | 3 | NMRI/♀/Chow | SEQ ID NO 41 equimolar 11.3 mg/kg | 1.13 mg/ml | iv | 0 | 0, 7, 10 | 10 |
|  | 24 | 70-72 | 3 | NMRI/♀/Chow | SEQ ID NO 42 equimolar 12.7 mg/kg | 1.27 mg/ml | iv | 0 | 0, 7, 10 | 10 |
| A | 25 | 73-75 | 3 | NMRI/♀/Chow | Saline | — | iv | 0 | 0, 1 | 1 |

Dose administration. NMRI female animals, app. 20 g at arrival, were dosed with 10 ml per kg BW (according to day 0 bodyweight) i.v. of the compound formulated in saline or saline alone according to according to the table above.

Sampling of Liver and Kidney Tissue. The animals were anaesthetized with 70% $CO_2$-30% $O_2$ and sacrificed by cervical dislocation according to Table 4. One half of the large liver lobe and one kidney were minced and submerged in RNAlater.

Total RNA was extracted from maximum 10 mg of tissue homogenized by bead-milling in the presence of MagNA Pure LC RNA Isolation Tissue buffer (Roche cat.no 03 604 721 001) using the MagNa Pure 96 Cellular RNA Large Volume Kit (Roche cat no. 5467535001), according to the manufacturer's instructions. First strand synthesis was performed using Reverse Transcriptase reagents from Ambion according to the manufacturer's instructions.

For each sample 0.5 µg total RNA was adjusted to (10.8 µl) with RNase free $H_2O$ and mixed with 2 µl random decamers (50 µM) and 4 µl dNTP mix (2.5 mM each dNTP) and heated to 70° C. for 3 min after which the samples were rapidly cooled on ice. 2 µl 10× Buffer RT, 1 µl MMLV Reverse Transcriptase (100 U/µl) and 0.25 µl RNase inhibitor (10 U/µl) were added to each sample, followed by incubation at 42° C. for 60 min, heat inactivation of the enzyme at 95° C. for 10 min and then the sample was cooled to 4° C. cDNA samples were diluted 1:5 and subjected to RT-QPCR using Taqman Fast Universal PCR Master Mix 2× (Applied Biosystems Cat #4364103) and Taqman gene expression assay (mPCSK9, Mn00463738_m1 and mActin #4352341 E) following the manufacturers protocol and processed in an Applied Biosystems RT-qPCR instrument (7500/7900 or ViiA7) in fast mode.

Example 8: Non-Human Primate Study; Multiple Injections s.c

The objective of this non-human primate study was to assess efficacy and safety of the anti-PCSK9 compounds in a repeat administration setting, when compounds were administered by subcutaneous injection (s.c.). The compounds used in this study were SEQ ID NOs 2, 3, 18, and 19, prepared in sterile saline (0.9%) at an initial concentration of 0.625 and 2.5 mg/ml.

Female cynomolgus monkeys of at least 24 months old were used, and given free access to tap water and 180 g of OWM(E) SQC SHORT expanded diet (Dietex France, SDS, Saint Gratien, France) was distributed daily per animal. In addition, fruit or vegetables were given daily to each animal. The animals were acclimated to the study conditions for a period of at least 14 days before the beginning of the treatment period. During this period, pre-treatment investigations were performed. The animals were dosed s.c. once per week for four weeks at a dose of 0.5 mg/kg (SEQ ID NO 2, 3, 18, and 19) or 1.5 mg/kg/injection (SEQ ID NO 18 and 19), with four injections total over a period of four weeks. The dose volume was 0.4 mL/kg/injection. Six animals were used per group. After the fourth and final dose animals were observed for a week after which half the animals were sacrificed in order to study liver apoB transcript regulation, lipid parameters, liver and kidney histology, and liver and kidney tissue distribution. Day 1 corresponds to the first day of the treatment period. Clinical observations and body weight and food intake (per group) was recorded prior to and during the study.

Blood and tissues were sampled and analysed at the following time points:

| Study Day | Parameters |
|---|---|
| −10 | L, Apo-B, OA |
| −5 | LSB, L, Apo-B, OA |
| −1 | RCP,L, Apo-B, PK, OA |
| 1 | Dosing |
| 8 pre-dose | LSB, L, Apo-B, PK, OA |
| 8 | Dosing |
| 15 pre-dose | LSB, L, Apo-B, PK, OA |
| 15 | Dosing |
| 22 pre-dose | LSB, L, Apo-B, PK, OA |
| 22 | Dosing |
| 29 | RCP, PK, OA + necropsy main |
| 36 (recovery animals) | LSB, L, Apo-B, PK, OA |
| 43 (recovery animals) | RCP, PK, Apo-B, PK, OA |
| 50 (recovery animals) | LSB, L, Apo-B, PK, OA |
| 57 (recovery animals) | LSB, L, Apo-B, PK, OA |
| 64 (recovery animals) | LSB, L, Apo-B, PK, OA |
| 71 (recovery animals) | LSB, L, Apo-B, PK, OA |
| 78 (recovery animals) | RCP, L, Apo-B, PK, OA + necropsy recovery |

RCP: routine clinical pathology, LSB: liver safety biochemistry, PK: pharmacokinetics, OA: other analyses, L: lipids Blood (approximately 1.0 mL) was taken into lithium heparin tubes (using the ADVIA 1650 blood biochemistry analyser) analyzing sodium, potassium, chloride, calcium, inorganic phosphorus, glucose, HDL-C, LDL-C, urea, creatinine, total bilirubin (TBIL), total cholesterol, triglycerides, alkaline phosphatase (ALP), alanine aminotransferase (ALAT), aspartate aminotransferase (ASAT), creatine kinase, gamma-glutamyl transferase (GGT), lactate dehydrogenase, total protein, albumin, albumin/globulin ratio.

Analysis of blood: Blood samples for ApoB analysis was collected from Group 1-16 animals only (i.e. animals treated with anti-ApoB compounds) on Days −8, −1, 4, 8, 15, 22, 29, 36, 43 and 50. Venous blood (approximately 2 mL) was collected from an appropriate vein in each animal into a Serum Separating Tube (SST) and allowed to clot for at least 60±30 minutes at room temperature. Blood was centrifuged at 1000 g for 10 minutes under refrigerated conditions (set to maintain +4° C.). The serum was transferred into 3 individual tubes and stored at −80° C. until analysis of ApoB protein by ELISA.

Other Analysis: WO2010142805 provides the methods for the following analysis: qPCR, ApoB mRNA analysis. Other analysis includes, serum Lp(a) analysis with ELISA (Mercodia No. 10-1106-01), tissue and serum oligonucleotide analysis (drug content), Extraction of samples, standard- and QC-samples, Oligonucleotide content determination by ELISA.

Figure 16:
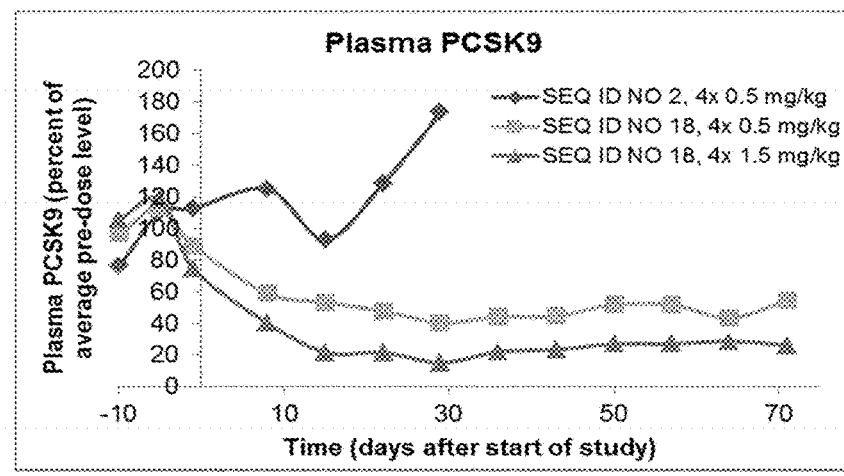
FIG. 16: Serum PCSK9 and LDL cholesterol in samples from cynomolgus monkeys injected four times (one injection/week) with 0.5 or 1.5 mg/kg/week of SEQ ID 2 and 18.

The intended pharmacology for an anti-PCSK9 oligonucleotide is reduction in LDL cholesterol by a reduction of PCSK9 protein in circulation ("serum PCSK9"). The GalNAc conjugated molecules demonstrated enhanced efficacy compared to unconjugated molecules when studying both serum PCSK9 and LDL cholesterol (FIG. 16 and FIG. 17). FIG. 16 illustrates that four weekly injections of 0.5 mg/kg/ injection of the unconjugated SEQ ID NO 2 had only minor effects on serum PCSK9 and LDL cholesterol, whereas the GalNAc conjugate of the same LNA gap-mer (SEQ ID 18) had a potent reducing effect on both serum PCSK9 and LDL cholesterol. The same relation was noted when comparing data for multiple injections of SEQ ID NO 3 and SEQ ID NO 19 (FIG. 17): only minor effects of the unconjugated molecule and potent down-regulation of serum PCSK9 and LDL cholesterol by the corresponding GalNAc conjugate (SEQ ID NO 19). It should be noted that effects of SEQ ID 18 and 19 on serum PCSK9 and LDL cholesterol were dose dependent and with long duration of action, with serum PCSK9 and LDL cholesterol lower than average baseline levels for at least seven weeks after the last injection (last injection day 22, data illustrated for the recovery period up to day 71).

Liver and kidney oligonucleotide content was analysed one week after last injection, i.e. day 29 of the study. Oligonucleotide content was analysed using hybridization ELISA (essentially as described in Lindholm et al, Mol Ther. 2012 February; 20(2):376-81), using SEQ ID NO 2 to prepare a standard curve for samples from animals treated with SEQ ID NO 2 and SEQ ID NO 18, after having controlled that there was no change in result if the (conjugated) SEQ ID NO 18 was used for preparation of standard curve. In the same manner, SEQ ID NO 3 was used for preparation of standard curve for SEQ ID NO 3 and SEQ ID NO 19 after controlling that there was no difference in result if SEQ ID NO 19 was used for preparation of standard curve for ELISA analysis of those samples.

| Oligonucleotide content in tissues one week after last injection | | | | | |
|---|---|---|---|---|---|
| | Liver (µg oligonucleotide/ g wet tissue) | | Kidney (µg oligonucleotide/ g wet tissue) | | Liver/ kidney |
| | Average | SD | Average | SD | ratio |
| SEQ ID NO 2, 4x0,5 mg/kg | 0.260 | 0.14 | 30.3 | 4.8 | 0.008 |
| SEQ ID NO 18, 4x0,5 mg/kg | 3.57 | 0.61 | 11.5 | 2.5 | 0.310 |
| SEQ ID NO 18, 4x1,5 mg/kg | 18.8 | 1.7 | 26.8 | 6.6 | 0.701 |
| SEQ ID NO 3, 4x0,5 mg/kg | 0.149 | 0.059 | 38.2 | 0.72 | 0.004 |
| SEQ ID NO 19, 4x0,5 mg/kg | 2.72 | 0.69 | 16.3 | 1.5 | 0.167 |
| SEQ ID NO 19, 4x1,5 mg/kg | 12.2 | 3.44 | 41.2 | 6.5 | 0.296 |

As illustrated in the table above, conjugation of SEQ ID NO 2 and SEQ ID NO 3 resulted in higher liver/kidney ratios for the conjugated molecules (SEQ ID NO 18 and SEQ ID 19) than for the corresponding unconjugated molecules one week after last injection when animals were injected s.c. once/week for four weeks. Given that signs of tubulotoxicity has been demonstrated with other unconjugated anti-PCSK9 molecules (such as SEQ ID NO 1, as illustrated in FIG. 15), and given that liver is the target organ for anti-PCSK9 treatment, a shift to a higher liver/kidney ratio is expected to result in increased safety with the conjugated SEQ ID NO 18 and 19 compared to the unconjugated SEQ ID NO 2 and 3.

As illustrated in FIG. 16 and FIG. 17, SEQ ID NO 18 and 19 were dosed at pharmacology relevant levels. Clinical chemistry profiles of the same animals during the treatment period and the recovery phase demonstrated no clinically relevant increases in liver or kidney safety parameters.

The invention claimed is:

1. A method of reducing cholesterol levels in a subject in need thereof comprising administering to said subject an effective amount of a compound consisting of
  an antisense oligomer that is 16 contiguous nucleotides in length, wherein the sequence of the antisense oligomer is 100% complementary to the sequence of SEQ ID NO: 31, wherein the antisense oligomer is a gapmer comprising at least one LNA unit; and
  wherein the antisense oligomer targets mRNA encoding PCSK9.

2. The method of claim 1, wherein the cholesterol is serum LDL cholesterol.

3. The method of claim 1, further comprising the administration of a second therapeutic agent.

4. The method of claim 3, wherein the second therapeutic agent is a statin.

5. The method of claim 4, wherein the statin is selected from the group consisting of lovastatin, cerivastatin, pravastatin, atorvastatin, simvastatin, rosuvastatin, and fluvastatin.

6. The method of claim 4, wherein the second therapeutic agent is a bile sequestering resin, nicotinic acid, a fibric acid derivative, probucol, neomycin, dextrothyroxine, a plant stanol ester, a cholesterol absorption inhibitor, implitapide, an inhibitor of bile acid transporters, a regulator of hepatic CYP7a, an estrogen replacement therapeutic, or an anti-inflammatory.

7. The method of claim 1, wherein the compound is administered intravenously or subcutaneously.

8. The method of claim 1, wherein the compound is administered as a single dose or as multiple doses.

9. The method of claim 1, wherein the sequence of the antisense oligomer is SEQ ID NO: 26.

10. The method of claim 1, wherein the LNA is oxy-LNA, thio-LNA, amino-5 LNA, 5'-methyl-LNA, ENA, cET, cMOE or a combination thereof.

11. The method of claim 1, wherein the LNA is an stereoisomer in the beta-D-configuration or the alpha-L configuration.

12. The method of claim 1, wherein the antisense oligomer comprises at least one cET unit.

13. The method of claim 1, wherein the antisense oligomer comprises six or seven LNA units.

14. The method of claim 13, wherein every LNA unit in the antisense oligomer is a beta-D-oxy LNA unit.

15. The method of claim 13, wherein every LNA unit in the antisense oligomer is a stereoisomer in the same configuration.

16. The method of claim 15, wherein every the LNA unit in the antisense oligomer is an stereoisomer in the R configuration.

17. The method of claim 15, wherein every the LNA unit in the antisense oligomer is an stereoisomer in the S configuration.

18. The method of claim 15, wherein every the LNA unit in the antisense oligomer is an stereoisomer in the D configuration.

19. The method of claim 15, wherein every the LNA unit in the antisense oligomer is an stereoisomer in the L configuration.

20. The method of claim 1, wherein the LNA is an (R,S) racemic mixture.

21. The method of claim 1, wherein the sequence of the antisense oligomer comprises at least one phosphorothioate internucleoside linkage.

22. The method of claim 1, wherein the sequence of the antisense oligomer is SEQ ID NO: 2.

23. The method of claim 1, wherein the sequence of the antisense oligomer is SEQ ID NO: 3.

24. The method of claim 1, wherein the compound and an oligomer of SEQ ID NO:31 can form a duplex with increased thermal stability with respect to a corresponding duplex comprising the corresponding antisense oligomer without LNA.

25. A method of reducing cholesterol levels in a subject in need thereof comprising administering to said subject an effective amount of an antisense oligonucleotide conjugate comprising:
  an antisense oligomer that is 16 contiguous nucleotides in length, wherein the sequence of the antisense oligomer is 100% complementary to the sequence of SEQ ID NO: 31, and wherein the antisense oligomer is a gapmer comprising at least one LNA unit; and at least one non-nucleotide or non-polynucleotide moiety covalently attached to said antisense oligomer directly or via a linker positioned between the contiguous oligomer sequence and the non-nucleotide or non-polynucleotide moiety, wherein the antisense oligomer targets mRNA encoding PCSK9.

26. The method of claim 25, wherein the non-nucleotide or non-polynucleotide moiety is a liver targeting moiety that is attached to the 5'-end or to the 3'-end of the antisense oligomer.

27. The method of claim 26, wherein the liver targeting moiety is linked to the antisense oligomer via a linker.

28. The method of claim 27, wherein the linker is a biocleavable linker.

36. The method of claim 35, wherein the asialoglycoprotein receptor targeting conjugate moiety comprises a GalNAc cluster.

37. The method of claim 35, wherein the asialoglycoprotein receptor targeting conjugate moiety comprises a monovalent, divalent, trivalent, or tetravalent GalNAc cluster.

38. The method of claim 36, wherein the GalNAc cluster is a trivalent GalNAc cluster.

39. The method of claim 38, wherein each GalNAc in the trivalent GalNAc cluster is attached to a branch point group via a spacer.

40. The method of claim 39, wherein the branch point group comprises di-lysine.

41. The method of claim 39, wherein the spacer comprises a PEG spacer.

42. The method of claim 27, wherein the linker comprises a C6 to C12 amino alkyl group or a biocleavable phosphate nucleotide linker comprising between 1 to 6 nucleotides.

43. The method of claim 38, wherein the trivalent GalNAc cluster comprises Conj 2a:

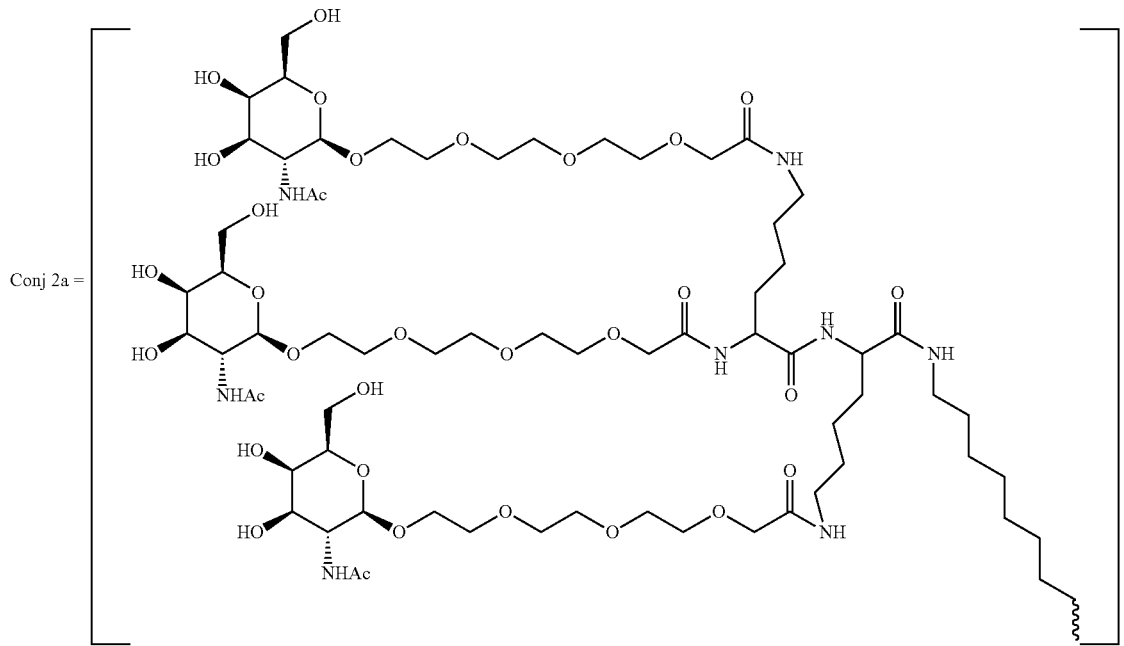

29. The method of claim 26, wherein the liver targeting moiety comprises a carbohydrate conjugate moiety comprising a carbohydrate or a carbohydrate group.

30. The method of claim 29, wherein the carbohydrate is selected from the group consisting of galactose, lactose, N-acetylgalactosamine (GalNAc), mannose, mannose-6-phosphate, and combinations thereof.

31. The method of claim 29, wherein the carbohydrate conjugate moiety is not a linear carbohydrate polymer.

32. The method of claim 29, wherein the carbohydrate conjugate moiety is a carbohydrate group comprising 1 2, 3, or 4 carbohydrate moieties.

33. The method of claim 32, wherein the carbohydrate moieties are identical or non-identical.

34. The method of claim 32, wherein the carbohydrate moieties are non-identical.

35. The method of claim 29, wherein the carbohydrate conjugate moiety comprises at least one asialoglycoprotein receptor targeting conjugate moiety.

44. The method of claim 25, wherein the non-nucleotide or non-polynucleotide moiety is covalently attached to the antisense oligomer via a covalent bond.

45. The method of claim 25, wherein the antisense oligonucleotide conjugate is SEQ ID NO: 18.

46. The method of claim 25, wherein the antisense oligonucleotide conjugate is SEQ ID NO: 19.

47. The method of claim 25, wherein the cholesterol is serum LDL cholesterol.

48. The method of claim 25, further comprising the administration of a second therapeutic agent.

49. The method of claim 48, wherein the second therapeutic agent is a statin.

50. The method of claim 49, wherein the statin is selected from the group consisting of lovastatin, cerivastatin, pravastatin, atorvastatin, simvastatin, rosuvastatin, and fluvastatin.

51. The method of claim 48, wherein the second therapeutic agent is a bile sequestering resin, nicotinic acid, a fibric acid derivative, probucol, neomycin, dextrothyroxine, a plant stanol ester, a cholesterol absorption inhibitor, implitapide, an inhibitor of bile acid transporters, a regulator of hepatic CYP7a, an estrogen replacement therapeutic, or an anti-inflammatory.

52. The method of claim 25, wherein the antisense oligonucleotide conjugate is administered intravenously or subcutaneously.

53. The method of claim 25, wherein the antisense oligonucleotide conjugate is administered as a single dose or as multiple doses.

54. A method of reducing cholesterol levels in a subject in need thereof comprising administering to said subject an effective amount of an antisense oligonucleotide conjugate of SEQ ID NO: 18

SEQ ID NO: 18

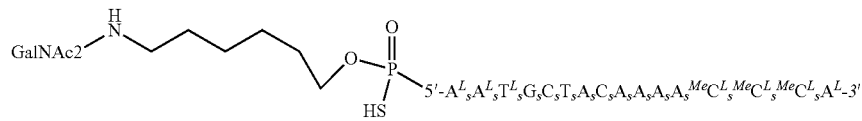

wherein
   a superscript $^L$ identifies a beta-D-oxy LNA unit,
   a $^{Me}$C identifies a 5-methylcytosine unit,
   a subscript $_s$ identifies a phosphorothioate internucleoside linkage,
and wherein

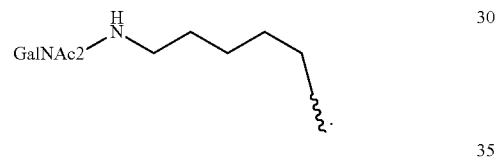

is a Conj 2a asialoglycoprotein receptor targeting conjugate moiety

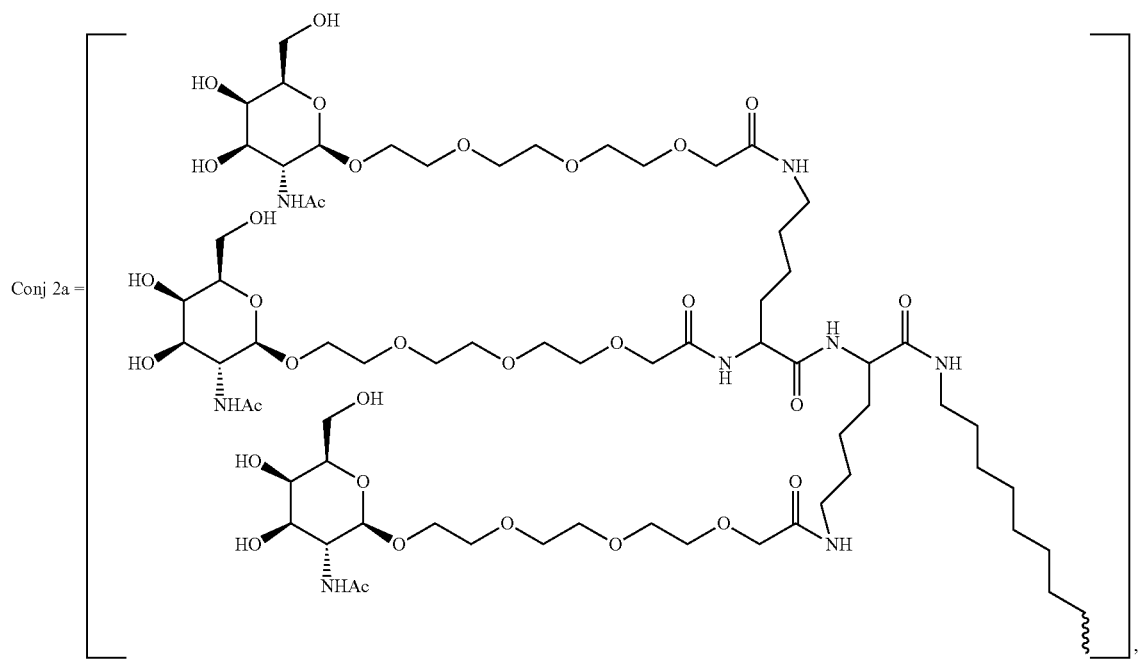

and wherein the antisense oligonucleotide conjugate targets mRNA encoding PCSK9.

55. A method of reducing cholesterol levels in a subject in need thereof comprising administering to said subject an effective amount of an antisense oligonucleotide conjugate of SEQ ID NO: 19

SEQ ID NO: 19

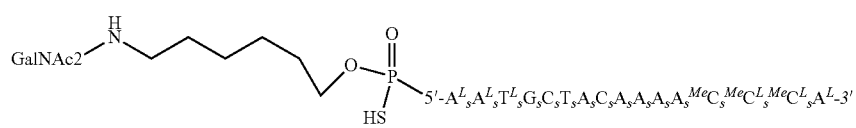

wherein
a superscript $^L$ identifies a beta-D-oxy LNA unit,
a $^{Me}C$ identifies a 5-methylcytosine unit,
a subscript $_s$ identifies a phosphorothioate internucleoside linkage,
and wherein

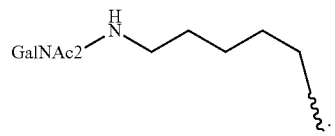

is a Conj 2a asialoglycoprotein receptor targeting conjugate moiety

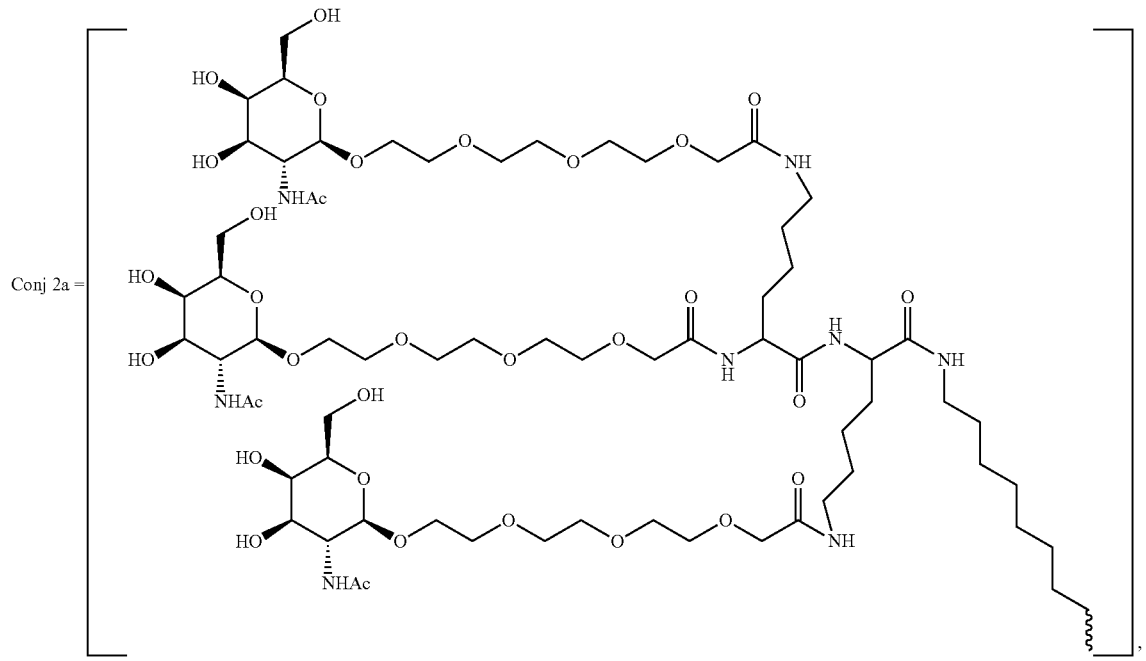

and wherein the antisense oligonucleotide conjugate targets mRNA encoding PCSK9.

56. The method of claim 25, wherein the antisense oligomer comprises six or seven LNA units.

57. The method of claim 56, wherein every LNA unit in the antisense oligomer is a beta-D-oxy LNA unit.

58. The method of claim 56, wherein every LNA unit in the antisense oligomer is a stereoisomer in the same configuration.

59. The method of claim 58, wherein every the LNA unit in the antisense oligomer is an stereoisomer in the R configuration.

60. The method of claim 58, wherein every the LNA unit in the antisense oligomer is an stereoisomer in the S configuration.

61. The method of claim 58, wherein every the LNA unit in the antisense oligomer is an stereoisomer in the D configuration.

62. The method of claim 58, wherein every the LNA unit in the antisense oligomer is an stereoisomer in the L configuration.

63. The method of claim 25, wherein the LNA is an (R,S) racemic mixture.

* * * * *

UNITED STATES PATENT AND TRADEMARK OFFICE
CERTIFICATE OF CORRECTION

PATENT NO. : 10,385,342 B2
APPLICATION NO. : 15/971970
DATED : August 20, 2019
INVENTOR(S) : Albaek et al.

It is certified that error appears in the above-identified patent and that said Letters Patent is hereby corrected as shown below:

In the Claims

In Column 103, Line 27, delete the text beginning with "1. A method of" to and ending in "racemic mixture." in Column 110, Line 65, and insert the following claims:
-- 1. A method of reducing cholesterol levels in a subject in need thereof comprising administering to said subject an effective amount of a compound consisting of an antisense oligomer that is 16 contiguous nucleotides in length, wherein the sequence of the antisense oligomer is 100% complementary to the sequence of SEQ ID NO: 31, wherein the antisense oligomer is a gapmer comprising at least one LNA unit; and wherein the antisense oligomer targets mRNA encoding PCSK9.
2. The method of claim 1, wherein the cholesterol is serum LDL cholesterol.
3. The method of claim 1, further comprising the administration of a second therapeutic agent.
4. The method of claim 3, wherein the second therapeutic agent is a statin.
5. The method of claim 4, wherein the statin is selected from the group consisting of lovastatin, cerivastatin, pravastatin, atorvastatin, simvastatin, rosuvastatin, and fluvastatin.
6. The method of claim 4, wherein the second therapeutic agent is a bile sequestering resin, nicotinic acid, a fibric acid derivative, probucol, neomycin, dextrothyroxine, a plant stanol ester, a cholesterol absorption inhibitor, implitapide, an inhibitor of bile acid transporters, a regulator of hepatic CYP7a, an estrogen replacement therapeutic, or an antiinflammatory.
7. The method of claim 1, wherein the compound is administered intravenously or subcutaneously.
8. The method of claim 1, wherein the compound is administered as a single dose or as multiple doses.
9. The method of claim 1, wherein the sequence of the antisense oligomer is SEQ ID NO: 26.
10. The method of claim 1, wherein the LNA is oxy-LNA, thio-LNA, amino-5 LNA, 5'-methyl-LNA, ENA, cET, cMOE or a combination thereof.
11. The method of claim 1, wherein the LNA is a stereoisomer in the beta-D-configuration or the alpha-L configuration.

Signed and Sealed this
Twenty-ninth Day of October, 2019

Andrei Iancu
*Director of the United States Patent and Trademark Office*

12. The method of claim 1, wherein the antisense oligomer comprises at least one cET unit.
13. The method of claim 1, wherein the antisense oligomer comprises six or seven LNA units.
14. The method of claim 13, wherein every LNA unit in the antisense oligomer is a beta-D-oxy LNA unit or every LNA unit in the antisense oligomer is an alpha-L-oxy-LNA unit.
15. The method of claim 13, wherein every LNA unit in the antisense oligomer is a stereoisomer in the same configuration.
16. The method of claim 1, wherein the sequence of the antisense oligomer comprises at least one phosphorothioate, phosphorodithioate, or boranophosphate internucleoside linkage.
17. The method of claim 16, wherein all the internucleoside linkages are phosphorothioate.
18. The method of claim 16, wherein one or more of the internucleoside linkages comprises a chiral center in the R conformation and/or in the S conformation.
19. The method of claim 1, wherein the sequence of the antisense oligomer is SEQ ID NO: 2.
20. The method of claim 1, wherein the sequence of the antisense oligomer is SEQ ID NO: 3.
21. The method of claim 1, wherein the compound and an oligomer of SEQ ID NO: 31 can form a duplex with increased thermal stability with respect to a corresponding duplex comprising the corresponding antisense oligomer without LNA.
22. A method of reducing cholesterol levels in a subject in need thereof comprising administering to said subject an effective amount of an antisense oligonucleotide conjugate comprising:

an antisense oligomer that is 16 contiguous nucleotides in length, wherein the sequence of the antisense oligomer is 100% complementary to the sequence of SEQ ID NO: 31, and wherein the antisense oligomer is a gapmer comprising at least one LNA unit; and at least one non-nucleotide or non-polynucleotide moiety covalently attached to said antisense oligomer directly or via a linker positioned between the contiguous oligomer sequence and the non-nucleotide or non-polynucleotide moiety,
wherein the antisense oligomer targets mRNA encoding PCSK9.
23. The method of claim 22, wherein the non-nucleotide or non-polynucleotide moiety is a liver targeting moiety that is attached to the 5'-end or to the 3'-end of the antisense oligomer.
24. The method of claim 23, wherein the liver targeting moiety is linked to the antisense oligomer via a linker.
25. The method of claim 24, wherein the linker is a biocleavable linker.
26. The method of claim 23, wherein the liver targeting moiety comprises a carbohydrate conjugate moiety comprising a carbohydrate or a carbohydrate group.
27. The method of claim 26, wherein the carbohydrate is selected from the group consisting of galactose, lactose, N-acetylgalactosamine (GalNAc), mannose, mannose-6-phosphate, and combinations thereof.
28. The method of claim 26, wherein the carbohydrate conjugate moiety is not a linear carbohydrate polymer.
29. The method of claim 26, wherein the carbohydrate conjugate moiety is a carbohydrate group comprising 1 2, 3, or 4 carbohydrate moieties.
30. The method of claim 29, wherein the carbohydrate moieties are identical or non-identical.
31. The method of claim 29, wherein the carbohydrate moieties are non-identical.
32. The method of claim 26, wherein the carbohydrate conjugate moiety comprises at least one asialoglycoprotein receptor targeting conjugate moiety.

33. The method of claim 32, wherein the asialoglycoprotein receptor targeting conjugate moiety comprises a GalNAc cluster.
34. The method of claim 32, wherein the asialoglycoprotein receptor targeting conjugate moiety comprises a monovalent, divalent, trivalent, or tetravalent GalNAc cluster.
35. The method of claim 33, wherein the GalNAc cluster is a trivalent GalNAc cluster.
36. The method of claim 35, wherein each GalNAc in the trivalent GalNAc cluster is attached to a branch point group via a spacer.
37. The method of claim 36, wherein the branch point group comprises di-lysine.
38. The method of claim 36, wherein the spacer comprises a PEG spacer.
39. The method of claim 24, wherein the linker comprises a C6 to C12 amino alkyl group or a biocleavable phosphate nucleotide linker comprising between 1 to 6 nucleotides.
40. The method of claim 35, wherein the trivalent GalNAc cluster comprises Conj 2a:

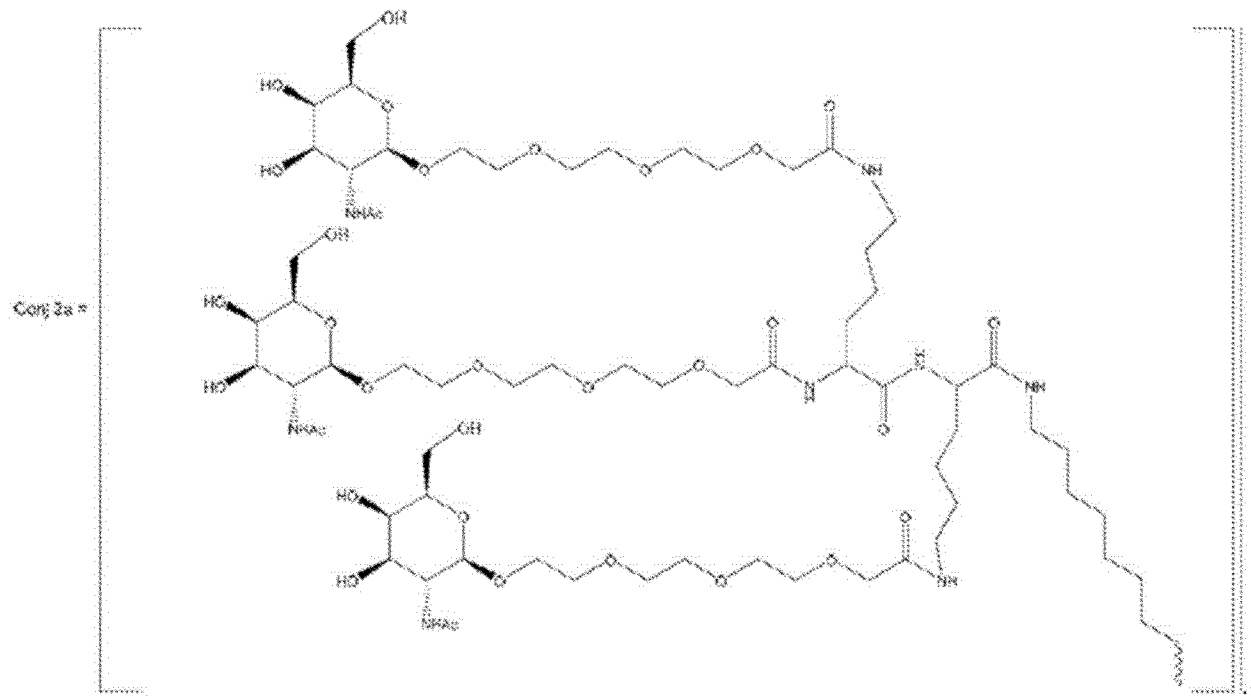

41. The method of claim 22, wherein the non-nucleotide or non-polynucleotide moiety is covalently attached to the antisense oligomer via a covalent bond.
42. The method of claim 22, wherein the antisense oligonucleotide conjugate is SEQ ID NO: 18.
43. The method of claim 22, wherein the antisense oligonucleotide conjugate is SEQ ID NO: 19.
44. The method of claim 22, wherein the cholesterol is serum LDL cholesterol.
45. The method of claim 22, further comprising the administration of a second therapeutic agent.
46. The method of claim 45, wherein the second therapeutic agent is a statin.
47. The method of claim 46, wherein the statin is selected from the group consisting of lovastatin, cerivastatin, pravastatin, atorvastatin, simvastatin, rosuvastatin, and fluvastatin.
48. The method of claim 45, wherein the second therapeutic agent is a bile sequestering resin, nicotinic acid, a fibric acid derivative, probucol, neomycin, dextrothyroxine, a plant stanol ester, a cholesterol absorption inhibitor, implitapide, an inhibitor of bile acid transporters, a regulator of hepatic CYP7a, an estrogen replacement therapeutic, or an anti-inflammatory.

49. The method of claim 22, wherein the antisense oligonucleotide conjugate is administered intravenously or subcutaneously.
50. The method of claim 22, wherein the antisense oligonucleotide conjugate is administered as a single dose or as multiple doses.
51. A method of reducing cholesterol levels in a subject in need thereof comprising administering to said subject an effective amount of an antisense oligonucleotide conjugate of SEQ ID NO: 18

SEQ ID NO: 18 wherein
- a superscript $^L$ identifies a beta-D-oxy LNA unit,
- a $^{Me}C$ identifies a 5-methylcytosine unit,
- a subscript $_s$ identifies a phosphorothioate internucleoside linkage, and wherein

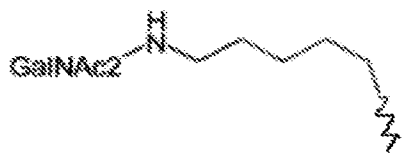

is a Conj 2a asialoglycoprotein receptor targeting conjugate moiety

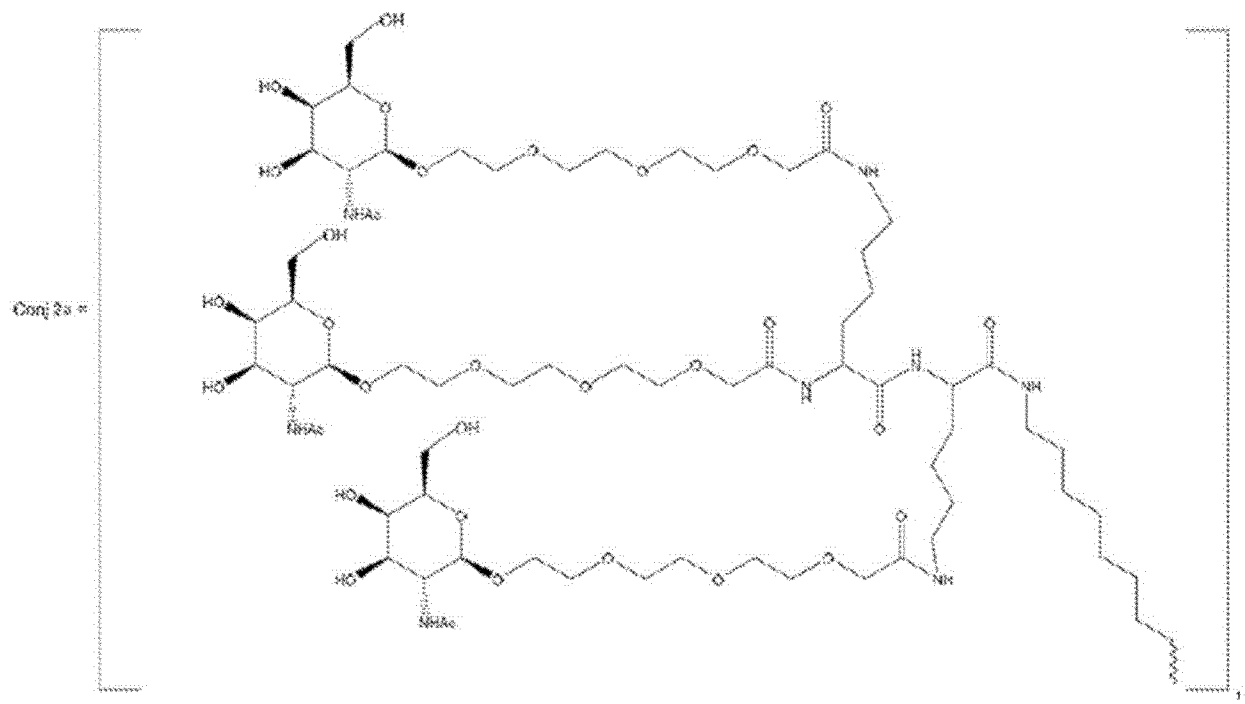

and wherein the antisense oligonucleotide conjugate targets mRNA encoding PCSK9.

52. A method of reducing cholesterol levels in a subject in need thereof comprising administering to said subject an effective amount of an anti sense oligonucleotide conjugate of SEQ ID NO: 19

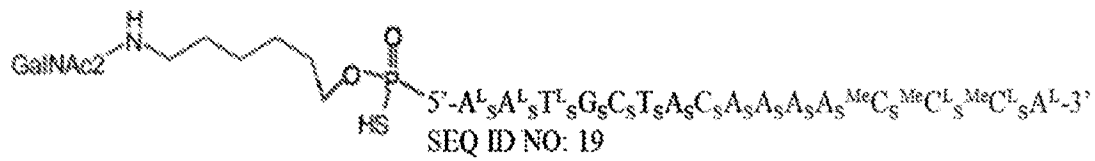

SEQ ID NO: 19 wherein
    a superscript $^L$ identifies a beta-D-oxy LNA unit,
    a $^{Me}C$ identifies a 5-methylcytosine unit,
    a subscript $_s$ identifies a phosphorothioate internucleoside linkage,
    and wherein

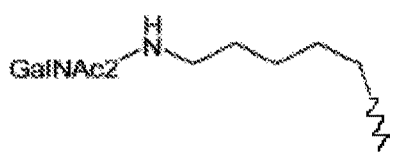

is a Conj 2a asialoglycoprotein receptor targeting conjugate moiety

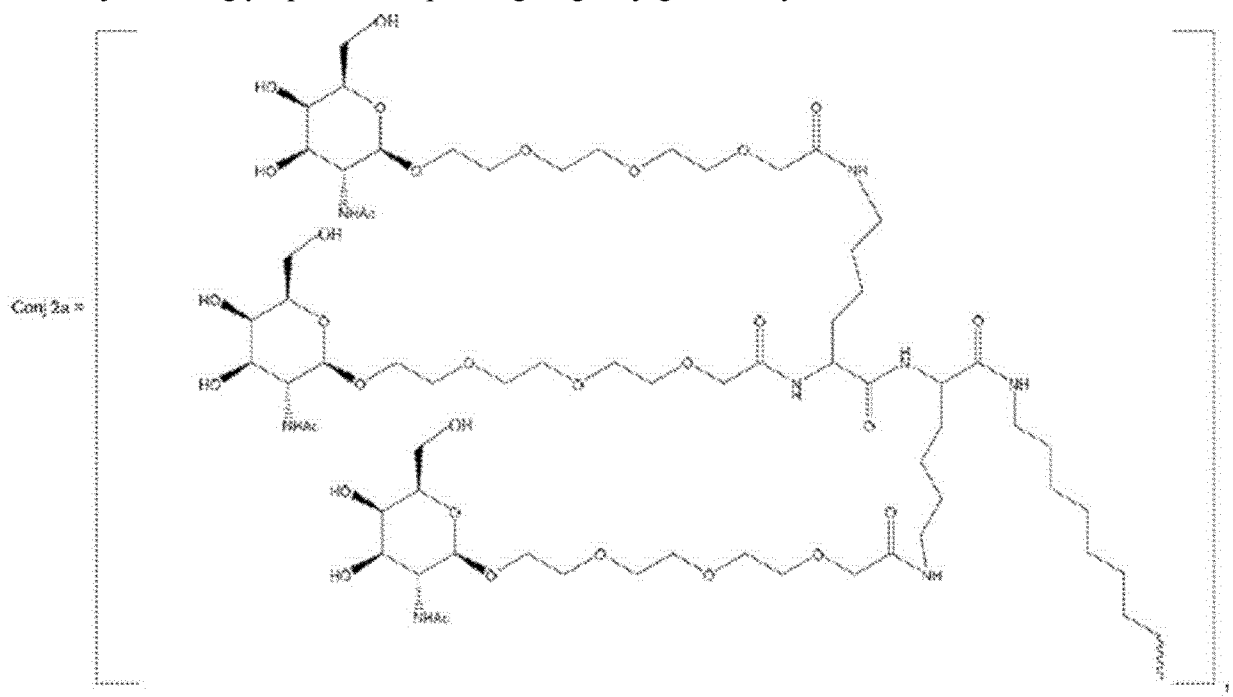

and wherein the antisense oligonucleotide conjugate targets mRNA encoding PCSK9.
53. The method of claim 22, wherein the antisense oligomer comprises six or seven LNA units.
54. The method of claim 53, wherein every LNA unit in the antisense oligomer is a beta-D-oxy LNA unit or every LNA unit in the antisense oligomer is an alpha-L-oxy-LNA unit.
55. The method of claim 53, wherein every LNA unit in the antisense oligomer is a stereoisomer in the same configuration.
56. The method of claim 22, wherein the sequence of the antisense oligomer comprises at least one phosphorothioate, phosphorodithioate, or boranophosphate internucleoside linkage.
57. The method of claim 56, wherein all the internucleoside linkages are phosphorothioate.

58. The method of claim 56, wherein one or more of the internucleoside linkages comprises a chiral center in the R conformation and/or in the S conformation. --